(12) United States Patent
Ikeda et al.

(10) Patent No.: US 10,047,346 B2
(45) Date of Patent: Aug. 14, 2018

(54) METHOD OF TREATING HEART TISSUE USING INDUCED PLURIPOTENT STEM CELLS

(75) Inventors: Yasuhiro Ikeda, Rochester, MN (US); Andre Terzic, Rochester, MN (US); Timothy J. Nelson, Rochester, MN (US); Amber A. Mael, Madison, WI (US); Almudena J. Martinez Fernandez, Rochester, MN (US); Satsuki Yamada, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 267 days.

(21) Appl. No.: 13/058,154

(22) PCT Filed: Aug. 10, 2009

(86) PCT No.: PCT/US2009/053314
§ 371 (c)(1),
(2), (4) Date: Apr. 27, 2011

(87) PCT Pub. No.: WO2010/017562
PCT Pub. Date: Feb. 11, 2010

(65) Prior Publication Data
US 2011/0200568 A1  Aug. 18, 2011

Related U.S. Application Data

(60) Provisional application No. 61/273,654, filed on Aug. 5, 2009, provisional application No. 61/271,341, filed on Jul. 20, 2009, provisional application No. 61/087,492, filed on Aug. 8, 2008.

(51) Int. Cl.
| | |
|---|---|
| *A01N 63/00* | (2006.01) |
| *A61K 48/00* | (2006.01) |
| *C12N 5/074* | (2010.01) |
| *A61K 35/12* | (2015.01) |

(52) U.S. Cl.
CPC ........... *C12N 5/0696* (2013.01); *A61K 35/12* (2013.01); *C12N 2500/90* (2013.01); *C12N 2500/98* (2013.01); *C12N 2501/602* (2013.01); *C12N 2501/603* (2013.01); *C12N 2501/604* (2013.01); *C12N 2501/605* (2013.01); *C12N 2501/606* (2013.01); *C12N 2501/608* (2013.01); *C12N 2510/00* (2013.01); *C12N 2740/16043* (2013.01)

(58) Field of Classification Search
USPC ............. 435/455, 325; 424/93.21, 93.1, 93.2
See application file for complete search history.

(56) References Cited

U.S. PATENT DOCUMENTS

| | | | |
|---|---|---|---|
| 8,048,999 B2 * | 11/2011 | Yamanaka et al. .......... 536/23.5 |
| 8,058,065 B2 * | 11/2011 | Yamanaka et al. ........... 435/377 |
| 8,129,187 B2 * | 3/2012 | Yamanaka et al. ........... 435/377 |
| 8,173,118 B2 * | 5/2012 | Terzic et al. ................. 424/85.2 |
| 8,278,104 B2 * | 10/2012 | Yamanaka et al. ........... 435/377 |
| 2004/0241838 A1 | 12/2004 | Johnson et al. |
| 2006/0084168 A1 | 4/2006 | Thomson et al. |
| 2011/0200568 A1* | 8/2011 | Ikeda ................... C12N 5/0696  424/93.21 |
| 2012/0164731 A1 | 6/2012 | Sakurai et al. |
| 2013/0029416 A1 | 1/2013 | Thatava et al. |
| 2013/0273013 A1 | 10/2013 | Revel et al. |
| 2014/0356951 A1 | 12/2014 | Thatava |
| 2017/0009210 A1 | 1/2017 | Ikeda et al. |

FOREIGN PATENT DOCUMENTS

| | | |
|---|---|---|
| EP | 1 970 446 | 9/2008 |
| WO | WO 2007/054720 | 5/2007 |
| WO | WO 2007/069666 | 6/2007 |
| WO | WO 2008/066630 | 6/2008 |
| WO | WO 2008/088882 | 7/2008 |

OTHER PUBLICATIONS

Jaenisch (Cell, Feb. 22, 2008, vol. 132, p. 567-582).*
Takahashi (Cell, 2006, vol. 126:663-676).*
Okita (Nature, 2007, vol. 448, p. 313-317).*
Yu (Science, 2007, vol. 318, p. 1917-1920).*
Nakagawa (Nat Biotechnol, Jan. 2008, vol. 26: 101-106).*
Okita (Science, Nov. 7, 2008, vol. 322, p. 949-953).*
Feng (Cell Stem Cell, Apr. 3, 2009, vol. 4, p. 301-312).*
Yu (Biochem. & Biophysical Res. Comm., Feb. 13, 2008, vol. 368, p. 942-947).*
Yanez (Nature Med. Mar. 2006, vol. 12, No. 3, p. 348-353).*
Saenz, J. Virol., Mar. 2004, vol. 78, No. 6, p. 2906-2920).*
Philippe (PNAS, Nov. 21, 2006, vol. 103, No. 47, p. 17584-17689.*
Apolonia (Mol. Therapy, Nov. 2007, vol. 15, No. 11, p. 1947-1954).*
Banasik (Gene Therapy, 2010, vol. 17, p. 150-157).*
Stadtfeld (Cell Stem Cell, Mar. 2008, vol. 2, p. 230-240).*
Stadtfeld (Science, Nov. 7, 2008, vol. 322, No. 5903, p. 945-949).*
Fusaki (Proc. Jpn. Acad., Ser. B, 2009, vol. 85, p. 348-362).*
Negri (Mol. Therapy, Sep. 2007, vol. 15, No. 9, p. 1716-1723).*
Nelson ("Repair of acute myocardial infarction by human sternness factors induced pluripotent stem cells", Circulation, Aug. 3, 2009, vol. 120, p. 408-416).*
Hanna (Science, Dec. 2007, vol. 318, p. 1920-1923.*

(Continued)

*Primary Examiner* — Michael C Wilson
(74) *Attorney, Agent, or Firm* — Fish & Richardson P.C.

(57) ABSTRACT

This document provides methods and materials related to induced pluripotent stem cells. For example, induced pluripotent stem cells, compositions containing induced pluripotent stem cells, methods for obtaining induced pluripotent stem cells, and methods for using induced pluripotent stem cells are provided. In addition, methods and materials for using induced pluripotent stem cells to repair tissue (e.g., cardiovascular tissue) in vivo as well as methods and materials for using induced pluripotent stem cells to assess their therapeutic potential in appropriate animal models are provided.

6 Claims, 55 Drawing Sheets

(56) References Cited

OTHER PUBLICATIONS

Wernig (PNAS, Apr. 15, 2008, vol. 105, No. 15, p. 5856-5861.*
Xu (PNAS, Jan. 2009, vol. 106, No. 3, p. 808-813.*
Apolonia et al., "Stable gene transfer to muscle using non-integrating lentiviral vectors," *Mol. Ther.*, 15(11):1947-1954, print Nov. 2007, Epub Aug. 2007.
Behfar et al., "Cardiopoietic programming of embryonic stem cells for tumor-free heart repair," *J. Exp. Med.*, 204(2):405-420, Feb. 2007.
Behfar et al., "Stem cell differentiation requires a paracrine pathway in the heart," *FASEB J.*, 16(12):1558-1566, Oct. 2002.
Borowiak et al., "Small molecules efficiently direct endodermal differentiation of mouse and human embryonic stem cells," *Cell Stem Cell*, 4(4):348-358, Apr. 2009.
Buteau et al., "Glucagon-like peptide 1 induces pancreatic beta-cell proliferation via transactivation of the epidermal growth factor receptor," *Diabetes*, 52:124-132, Jan. 2003.
Chen et al., "A small molecule that directs differentiation of human ESCs into the pancreatic lineage," *Nat. Chem. Biol.*, 5(4):258-265, Apr. 2009.
Chung et al., "Mitochondrial oxidative metabolism is required for the cardiac differentiation of stem cells," *Nat. Clin. Pract. Cardiovasc. Med.*, 4 Suppl 1, S60-67 Feb. 2007.
Daheron et al., "LIF/STAT3 signaling fails to maintain self-renewal of human embryonic stem cells," *Stem Cells*, 22(5):770-778, 2004.
Demaison et al., "High-level transduction and gene expression in hematopoietic repopulating cells using a human immunodeficiency [correction of imunodeficiency] virus type 1-based lentiviral vector containing an internal spleen focus forming virus promoter," *Hum. Gene Ther.*, 13(7):803-813, May 2002.
Evans and Kaufman, "Establishment in culture of pluripotential cells from mouse embryos," *Nature*, 292(5819):154-156, Jul. 1981.
Faustino et al., "Genomic chart guiding embryonic stem cell cardiopoiesis ," *Genome Biol.*, 9(1):R6, Jan. 2008.
Feigner et al., "Enhanced gene delivery and mechanism studies with a novel series of cationic lipid formulations," *J. Biol. Chem.*, 269(4):2550-2561, Jan. 1994.
Finkel and Holbrook, "Oxidants, oxidative stress and the biology of ageing," *Nature*, 408(6809):239-247, Nov. 2000.
Flotte et al., "Stable in vivo expression of the cystic fibrosis transmembrane conductance regulator with an adeno-associated virus vector," *Proc. Natl. Acad. Sci. USA*, 90(22):10613-10617, Nov. 1993.
Fujii and Martin, "Incorporation of teratocarcinoma stem cells into blastocysts by aggregation with cleavage-stage embryos," *Dev. Biol.*, 74(1): 239-244, Jan. 1980.
GenBank® GI No. 109659099, Accession No. BC117435, "*Homo sapiens* POU class 5 homeobox 1, mRNA (cDNA clone MGC:151044 Image:40125986), complete cds," Jul. 17, 2007, 2 pages.
GenBank® GI No. 12652778, Accession No. BC000141, "*Homo sapiens* v-myc myelocytomatosis viral oncogene homolog (avian), mRNA (cDNA clone MGC:5183 Image:2985844), complete cds," Sep. 13, 2007, 3 pages.
GenBank® GI No. 163659904, Accession No. NM_000618, "*Homo sapiens* insulin-like growth factor 1 (somatomedin C) (IGF1), transcript variant 4, mRNA," Jul. 21, 2010, 5 pages.
GenBank® GI No. 188595715, Accession No. NM_001127500, "*Homo sapiens* met proto-oncogene (hepatocyte growth factor receptor) (MET), transcript variant 1, mRNA," Jul. 18, 2010, 7 pages.
GenBank® GI No. 20987475, Accession No. BC029923, "*Homo sapiens* Kruppel-like factor 4 (gut), mRNA (cDNA clone MGC:34918 Image:5111134), complete cds," Jul. 15, 2006, 3 pages.
GenBank® GI No. 255090638, Accession No. GQ351295, "*Homo sapiens* fibroblast growth factor 10 (FGF10) mRNA, complete cds," Aug. 9, 2009, 1 page.
GenBank® GI No. 291190799, Accession No. NM_002054.3, "*Homo sapiens* glucagon (GCG), mRNA," Sep. 26, 2010, 4 pages.
GenBank® GI No. 33869633, Accession No. BC013923, "*Homo sapiens* SRY (sex determining region Y)-box 2, mRNA (cDNA clone MGC:2413 Image:2823424), complete cds," Jul. 15, 2006, 2 pages.
GenBank® GI No. 33872076, Accession No. BC028566, "*Homo sapiens* lin-28 homolog (C. elegans), mRNA (cDNA clone MGC:15037 Image:3841184), complete cds," Jun. 19, 2006, 4 pages.
GenBank® GI No. 71043476, Accession No. BC099704.1, "*Homo sapiens* Nanog homeobox pseudogene 8, mRNA (cDNA clone MGC:119250 Image:40004920), complete cds," Nov. 7, 2006, 3 pages.
Hasegawa et al., "The use of a tropism-modified measles virus in folate receptor-targeted virotherapy of ovarian cancer," *Clin. Cancer Res.*, 12(20 Pt1):6170-6178, Oct. 2006.
Hodgson et al., "Stable benefit of embryonic stem cell therapy in myocardial infarction," *Am. J. Physiol. Heart Circ. Physiol.*, 287(2):H471-479, Aug. 2004.
Huangfu et al., "Induction of pluripotent stem cells from primary human fibroblasts with only Oct4 and Sox2," *Nat Biotechnol.*, 26(11):1269-1275, print Nov. 2008, Epub Oct. 2008.
Ikeda et al., "Continuous high-titer HIV-1 vector production," *Nat. Biotechnol.*, 21(5):569-572, print May 2003, Epub Apr. 2003.
Ikeda et al., "Gene transduction efficiency in cells of different species by HIV and EIAV vectors," *Gene Ther.*, 9(14):932-938, Jul. 2002.
Ikeda et al., "Influence of gag on human immunodeficiency virus type 1 species-specific tropism," *J. Virol.*, 78(21):11816-11822, Nov. 2004.
Kaplitt et al., "Long-term gene expression and phenotypic correction using adeno-associated virus vectors in the mammalian brain," *Nat. Genet.*, 8(2):148-154, Oct. 1994.
Kay et al., "Gene therapy," *Proc. Natl. Acad. Sci. USA*, 94(24):12744-12746, Nov. 1997.
Kootstra et al., "Abrogation of postentry restriction of HIV-1-based lentiviral vector transduction in simian cells," *Proc. Natl. Acad. Sci. USA*, 100(3):1298-1303, print Feb. 2003, Epub Jan. 2003.
Maehr et al., "Generation of pluripotent stem cells from patients with type 1 diabetes," *Proc. Natl. Acad. Sci. USA*, 106(37):15768-15773, Sep. 2009.
Mali et al., "Improved Efficiency and Pace of Generating Induced Pluripotent Stem Cells from Human Adult and Fetal Fibroblasts," *Stem Cells*, 2008, 26:1998-2005.
Martin, "Isolation of a pluripotent cell line from early mouse embryos cultured in medium conditioned by teratocarcinoma stem cells," *Proc. Natl. Acad. Sci. USA*, 78(12):7634-7638, Dec. 1981.
Martinez-Fernandez et al., "c-MYC independent nuclear reprogramming favors cardiogenic potential of induced pluripotent stem cells," *J Cardiovasc Transl Res.*, 3(1):13-23, Feb. 2010.
Martinez-Fernandez et al., "iPS programmed without c-MYC yield proficient cardiogenesis for functional heart chimerism," *Circ Res.*, 105(7):648-656, print Sep. 2009, Epub Aug. 2009.
Nagano and Fraser, "No-nonsense functions for long noncoding RNAs," *Cell*, 145(2):178-181, Apr. 2011.
Nagy et al., "Embryonic stem cells alone are able to support fetal development in the mouse," *Development*, 110(3):815-821, Nov. 1990.
Narazaki et al., "Directed and Systematic Differentiation of Cardiovascular Cells From Mouse Induced Pluripotent Stem Cells," *Circulation*, 118:498-506, 2008.
Negri et al., "Successful immunization with a single injection of non-integrating lentiviral vector," *Mol. Ther.*, 15(9):1716-1723, print Sep. 2007, Epub Jun. 2007.
Nelson et al., "CXCR4+/FLK-1+ biomarkers select a cardiopoietic lineage from embryonic stem cells," *Stem Cells*, 26(6):1464-1474, print Jun. 2008, Epub Mar. 2008.
Nelson et al., "Induced pluripotent reprogramming from promiscuous human stemness-related factors," *Clin Transl Sci.*, 2(2):118-126, Apr. 2009.
Nelson et al., "KCNJ11 knockout morula re-engineered by stem cell diploid aggregation," *Phil. Trans. R. Soc. B.*, 364(1514):269-276, Jan. 2009.

(56) References Cited

OTHER PUBLICATIONS

Nelson et al., "Lineage specification of Flk-1+ progenitors is associated with divergent Sox7 expression in cardiopoiesis," *Differentiation*, 77(3):248-255, Mar. 2009.
Nelson et al., "Repair of acute myocardial infarction by human sternness factors induced pluripotent stem cells," *Circulation*, 120(5):408-416, print, Aug. 2009, Epub Jul. 2009.
Noser et al., "Cyclosporine increases human immunodeficiency virus type 1 vector transduction of primary mouse cells," *J. Virol.*, 80(15):7769-7774, Aug. 2006.
Noser et al., "The RAS/Rafl/MEK/ERK signaling pathway facilitates VSV-mediated oncolysis: implication for the defective interferon response in cancer cells," *Mol. Ther.*, 15(8):1531-1536, print Aug. 2007, Epub May 2007.
Ohmine et al., "Induced pluripotent stem cells from GMP-grade hematopoietic progenitor cells and mononuclear myeloid cells," *Stem Cell Res Ther.*, 2(6):46, doi: 10.1186/scrt87, 12 pages, Nov. 2011.
Ohmine et al., "Reprogrammed keratinocytes from elderly type 2 diabetes patients suppress senescence genes to acquire induced pluripotency," *Aging*, 4(1):60-73, Jan. 2012.
Palmowski et al., "Intravenous injection of a lentiviral vector encoding NY-ESO-1 induces an effective CTL response," *J. Immunol.*, 172(3):1582-1587, Feb. 2004.
Paterson, "Arrhythmia: 100 years on from George Ralph Mines," J Physiol 591(17):4065-4066, Sep. 1, 2013, 2 pages.
Perez-Terzic et al., "Stem cells transform into a cardiac phenotype with remodeling of the nuclear transport machinery," *Nat. Clin. Pract. Cardiovasc. Med.*, 4 Suppl 1, S68-76, Feb. 2007.
Perez-Terzic et al., "Structural adaptation of the nuclear pore complex in stem cell-derived cardiomyocytes," *Circ. Res.*, 92(4):444-452, print Mar. 2003, Epub Jan. 2003.
Philpott et al., "A p5 integration efficiency element mediates Rep-dependent integration into AAVS1 at chromosome 19," *Proc. Natl. Acad. Sci. USA*, 99(19):12381-12385, Sep. 2002.
Philpott et al., "Efficient integration of recombinant adeno-associated virus DNA vectors requires a p5-rep sequence in cis," *J. Virol.*, 76(11):5411-5421, Jun. 2002.
Qi and Pei, "The magic of four: induction of pluripotent stem cells from somatic cells by Oct4, Sox2, Myc and Klf4," *Cell Research*, 17(7):578-580, Jul. 2007.
Rajasingh et al., "Cell-free embryonic stem cell extract-mediated derivation of multipotent stem cells from NIH3T3 fibroblasts for functional and anatomical ischemic tissue repair," *Circ Res.*, 102(11):e107-117 print Jun. 2008, Epub May 2008.
Ramiya et al., "Reversal of insulin-dependent diabetes using islets generated in vitro from pancreatic stem cells," *Nat. Med.*, 6(3):278-282, Mar. 2000.
Relander et al., "Gene transfer to repopulating human CD34+ cells using amphotropic-, GALV-, or RD114-pseudotyped HIV-1-based vectors from stable producer cells," Mol. Ther., 11(3):452-459, Mar. 2005.
Saenz et al., "Unintegrated lentivirus DNA persistence and accessibility to expression in nondividing cells: analysis with class I integrase mutants," *J. Virol.*, 78(6):2906-2290, Mar. 2004.
Sakuma et al., "Characterization of retroviral and lentiviral vectors pseudotyped with xenotropic murine leukemia virus-related virus envelope glycoprotein," *Hum. Gene Ther.*, 21(12):1665-1673, print Dec. 2010, Epub Sep. 2010.
Sakuma et al., "Inhibition of HIV-1 replication by simian restriction factors, TRIM5alpha and APOBEC3G," *Gene Ther.*, 14(2):185-189, print Jan. 2007, Epub Aug. 2006.
Schenke-Layland et al, "Reprogrammed mouse fibroblasts differentiate into cells of the cardiovascular and hematopoietic lineages," *Stem Cells*, 26(6):1537-1546, print Jun. 2008, Epub May 2008.
Softer and Knowles, "Monoclonal antibody defining a stage-specific mouse embryonic antigen (SSEA-1)," *Proc. Natl. Acad. Sci. USA*, 75(11):5565-5569, Nov. 1978.
Stewart, "Aggregation between teratocarcinoma cells and preimplantation mouse embryos," *J. Embryol. Exp. Morphol.*, 58:289-302, Aug. 1980.
Strang et al., "Characterization of HIV-1 vectors with gammaretrovirus envelope glycoproteins produced from stable packaging cells," *Gene Ther.*, 11(7):591-598, Apr. 2004.
Strang et al., "Human immunodeficiency virus type 1 vectors with alphavirus envelope glycoproteins produced from stable packaging cells," *J. Virol.*, 79(3):1765-1771, Feb. 2005.
Takahashi et al., "Induction of Pluripotent Stem Cells from Adult Human Fibroblasts by Defined Factors," *Cell*, 131:861-872, Nov. 2007.
Tateishi et al., "Stemming heart failure with cardiac- or reprogrammed-stem cells," *J Cell Mol Med.*, 12(6A):2217-2232, print Dec. 2008, Epub Aug. 2008.
Tateishi et al., Generation of insulin-secreting islet-like clusters from human skin fibroblasts. *Journal of Biological Chemistry*, 283(4):31600-31607, Nov. 2008.
Thatava et al., "Differentiation of Diabetic Patient-Specific iPS Cells into Insulin-Secreting Cells," *Molecular Therapy*, vol. 19, p. S121, abstract 311, May 2011.
Thatava et al., "Generation of glucose-responsive insulin-secreting cells from Type 1 Diabetes-specific induced pluripotent stem cells," 2011 Meeting on Stem Cell Engineering & Cell-based Therapies: Apr. 7-10, 2011, Cold Spring Harbor Laboratory, 25 pages.
Thatava et al., "Generation of insulin-secreting cells from human induced pluripotent stem cells," *Molecular Therapy*, vol. 18, p. S246, abstract 633, May 2010.
Thatava et al., "Generation of insulin-secreting cells from human induced pluripotent stem cells," *American Society of Gene and Cell Therapy* 13th Annual Meeting, Washington DC USA, May 19-22, 2010, 18 pages.
Thatava et al., "Indolactam V/GLP-1-mediated differentiation of human iPS cells into glucose-responsive insulin-secreting progeny," *Gene Therapy*, 18:283-293, print 2011, Epub Nov. 2010.
Thatava et al., "Pancreatic differentiation of diabetic patient-specific iPS cells," *American Society of Gene and Cell Therapy*,14th Annual Meeting, Seattle, WA, USA, May 18-21, 2011, 20 pages.
Thomson et al., "Embryonic stem cell lines derived from human blastocysts," *Science*, 282(5391):1145-1147, Nov. 1998.
Wernig et al., "c-Myc is dispensable for direct reprogramming of mouse fibroblasts," *Cell Stem Cell*, 2(1):10-12 print Jan. 2008, Epub Dec. 2007.
Wolf and Goff, "TRIM28 mediates primer binding site-targeted silencing of murine leukemia virus in embryonic cells," *Cell*, 131(1):46-57, Oct. 2007.
Wood et al., "Non-injection methods for the production of embryonic stem cell-embryo chimaeras," *Nature*, 365(6441):87-89, Sep. 1993.
Yamada et al., "Embryonic stem cell therapy of heart failure in genetic cardiomyopathy," *Stem Cells*, 26:2644-2653, Oct. 2008.
Yamada et al., "Induced pluripotent stem cell intervention rescues ventricular wall motion disparity, achieving biological cardiac resynchronization post-infarction," J Physiol., 591(17)4335-4349, Epub, Apr. 8, 2013.
Yamanaka, "Pluripotency and nuclear reprogramming," *Philos Trans R Soc Lond B Biol Sci.*, 363(1500):2079-2087, Jun. 2008.
Yu et al., "Induced pluripotent stem cell lines derived from human somatic cells," *Science*, 318(5858):1917-1920, print Dec. 2007, Epub Nov. 2007.
Yuasa and Fukuda, "Recent advances in cardiovascular regenerative medicine: the induced pluripotent stem cell era," *Expert Rev Cardiovasc Ther.*, 6(6):803-810, Jul. 2008.
Zufferey et al., "Multiply attenuated lentiviral vector achieves efficient gene delivery in vivo," Nat. Biotechnol., 15(9):871-875, Sep. 1997.
European Search Report for Application No. 09805666.6, dated Jun. 22, 2012, 11 pages.
International Preliminary Report on Patentability for PCT/US2009/053314, dated Feb. 8, 2011, 6 pages.
International Search Report and Written Opinion in International Application No. PCT/US2009/053314, dated Mar. 3, 2010, 15 pages.

(56) References Cited

OTHER PUBLICATIONS

Office Action in U.S. Appl. No. 13/553,064, dated Jul. 25, 2013, 6 pages.
Chen et al., "A small molecule that directs differentiation of human ESCs into the pancreatic lineage," Nat Chem Biol., 5(4):258-265, Epub Mar. 15, 2009 with 20 pages Supplementary Material.
Zawalich and Zawalich, "Effects of glucose, exogenous insulin, and carbachol on C-peptide and insulin secretion from isolated perifused rat islets," J Biol Chem., 277(29):26233-26237, Epub May 13, 2002.
Office Action in U.S. Appl. No. 13/553,064, dated Mar. 27, 2014, 11 pages.
Office Action in U.S. Appl. No. 14/340,161, dated Jul. 18, 2016, 23 pages.
Office Action in U.S. Appl. No. 14/340,161, dated Dec. 31, 2015, 14 pages.
International Preliminary Report on Patentability for PCT/US2015/014377, dated Aug. 18, 2016, 6 pages.
International Search Report and Written Opinion for PCT/US2015/014377, dated Apr. 17, 2015, 11 pages.
Bilic and Belmonte, "Concise Review: Induced Pluripotent Stem Cells Versus Embryonic Stem Cells: Close Enough or Yet Too Far Apart?" Stem Cell Res., 33:33-41, 2012.
Jiang et al., "Parkin controls dopamine utilization in human midbrain dopaminergic neurons derived from induced pluripotent stem cells," Nat Commun., 3:668, 9 pages, Feb. 7, 2012.
Karakikes et al., "Small molecule-mediated directed differentiation of human embryonic stem cells toward ventricular cardiomyocytes," Stem Cells Transl Med., 3(1):18-31. Epub Dec. 9, 2013, Jan. 2014.
Kim et al., "Epigenetic memory in induced pluripotent stem cells," Nature., 467(7313):285-290, Sep. 16, 2010.
Kroon et al., "Pancreatic endoderm derived from human embryonic stem cells generates glucose-responsive insulin-secreting cells in vivo," *Nat Biotechnol.*, 26(4):443-452, Epub Feb. 20, 2008.
Kudva et al., "Transgene-free disease-specific induced pluripotent stem cells from patients with type 1 and type 2 diabetes," *Stem Cells Transl Med.*, 1(6):451-461, Epub May 30, 2012.
Lister et al., "Hotspots of aberrant epigenomic reprogramming in human induced pluripotent stem cells," *Nature.*, 471(7336): 68-73, Mar. 3, 2011.
Yu et al., "Hepatocyte-like cells differentiated from human induced pluripotent stem cells: relevance to cellular therapies," Stem Cell Res., 9(3):196-207, Epub Jun. 28, 2012.
D'Amour et al., "Efficient differentiation of human embryonic stem cells to definitive endoderm," Nat. Biotechnol., 23(12):1534-1541, Dec. 2005.

\* cited by examiner

|  | HCF | | | BJ | | MRC-5 | |
|---|---|---|---|---|---|---|---|
|  | Exp.1 | Exp. 2 | Exp. 3 | Exp.1 | Exp. 2 | Exp.1 | Exp. 2 |
| No vector infection | 0 | N.D. | N.D. | 0 | 0 | 0 | 0 |
| Oct/Sox/Klf/Myc | 16 | 12 | 32 | 4 | 5 | 6 | 16 |
| Oct/Sox/Klf | 0 | 0 | N.D. | 0 | N.D. | 0 | N.D. |
| Oct/Sox/Klf/Lin28/Nanog | 3* | 2* | N.D. | 0 | N.D. | 0 | N.D. |

*After expansion, all the clones showed non-ES-like morphology.

FIG. 3

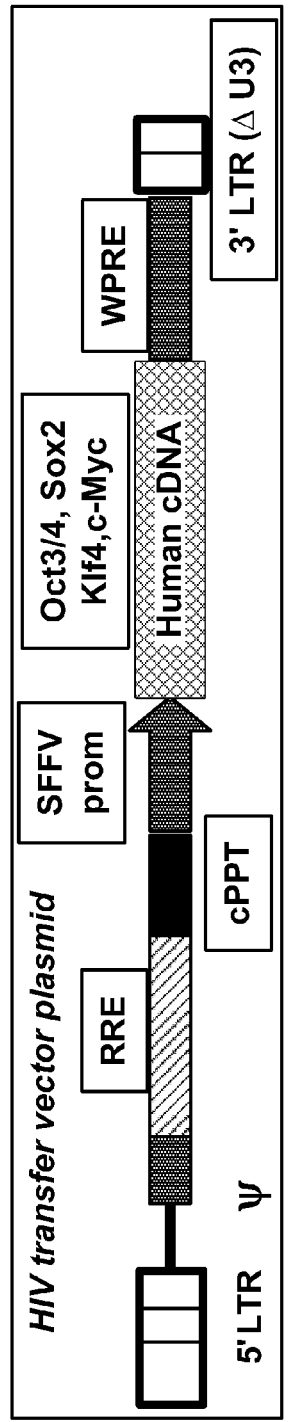
|  | Oct3/4 | Sox2 | Klf4 | c-Myc | LIF |
|---|---|---|---|---|---|
| *Homo sapiens* | 100.0 | 100.0 | 100.0 | 100.0 | 100.0 |
| *Macaca mulatta* | 98.3 | 99.4 | 92.8 | 98.2 | 99.0 |
| *Bos taurus* | 90.8 | 98.8 | 94.6 | 92.0 | 89.1 |
| *Sus scrofa* | 93.1 | 98.1 | 87.7 | 92.7 | 88.1 |
| *Canis lupus familiaris* | N.A. | 97.8 | N.A. | 92.3 | 92.1 |
| *Rattus norvegicus* | 84.4 | 97.8 | 90.1 | 89.7 | 82.7 |
| *Mus musculus* | 84.2 | 97.8 | 89.7 | 89.9 | 79.8 |
FIG. 24A
FIG. 24B
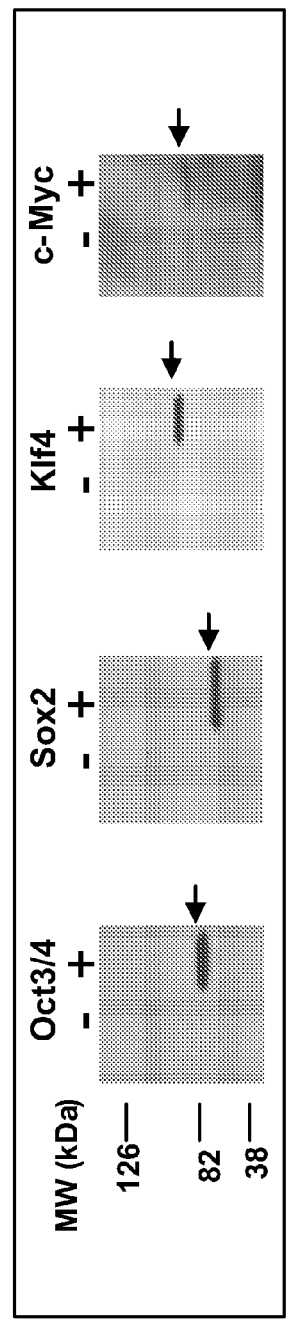
FIG. 24C Native | Transduced
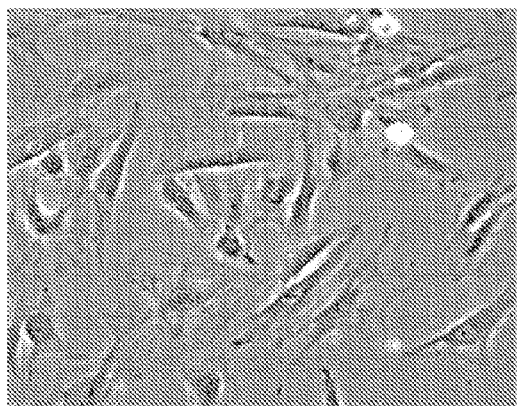 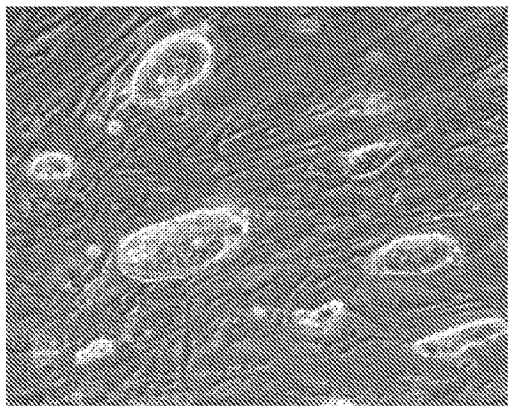
FIG. 25C | FIG. 25D
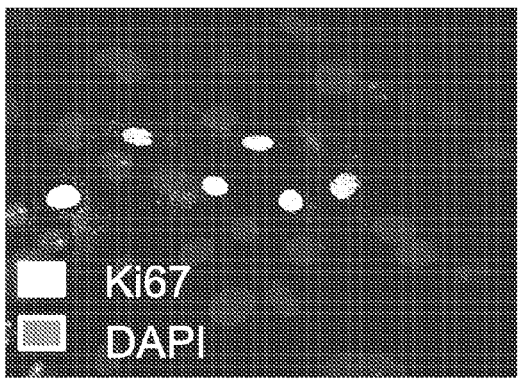 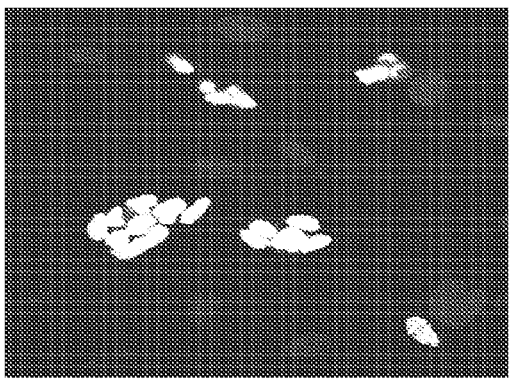
FIG. 25E | FIG. 25F
 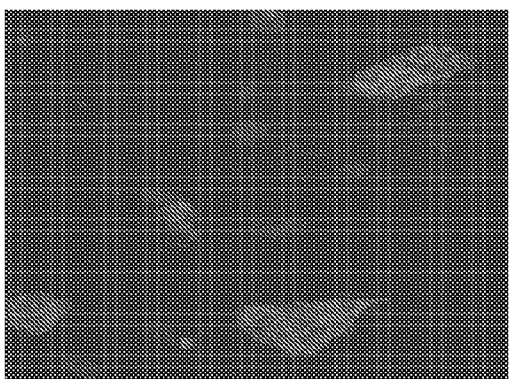
FIG. 25G | FIG. 25H

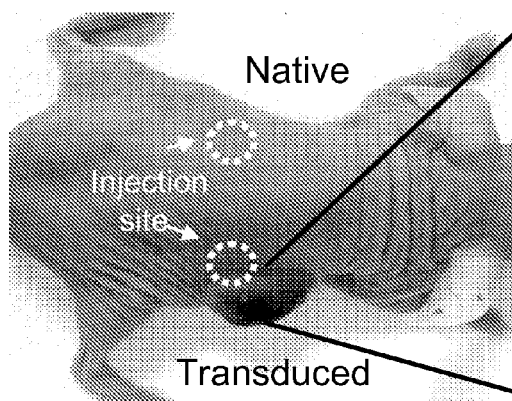
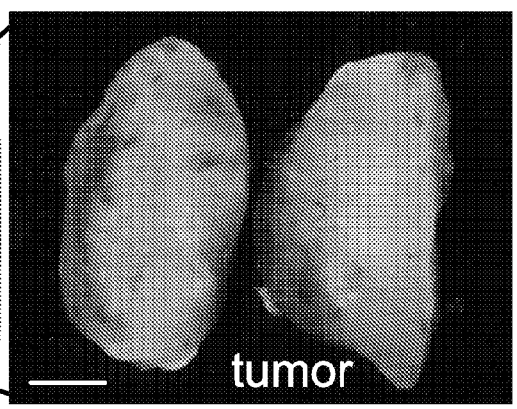
FIG. 27A  FIG. 27B
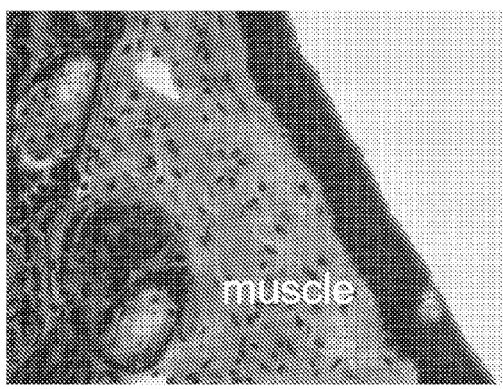
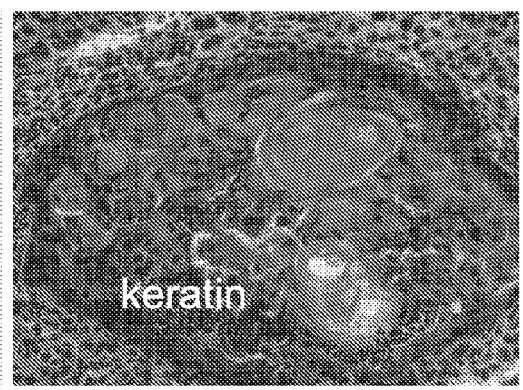
FIG. 27C  FIG. 27D
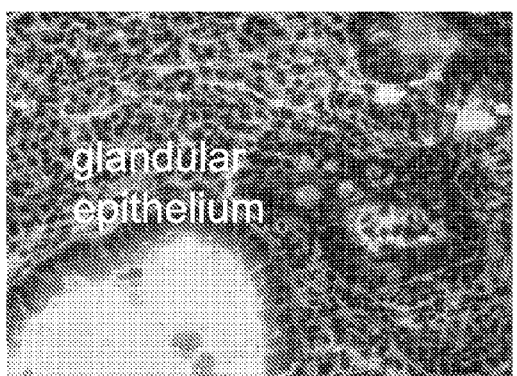
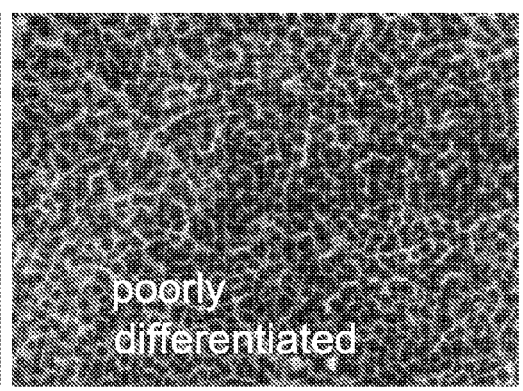
FIG. 27E  FIG. 27F

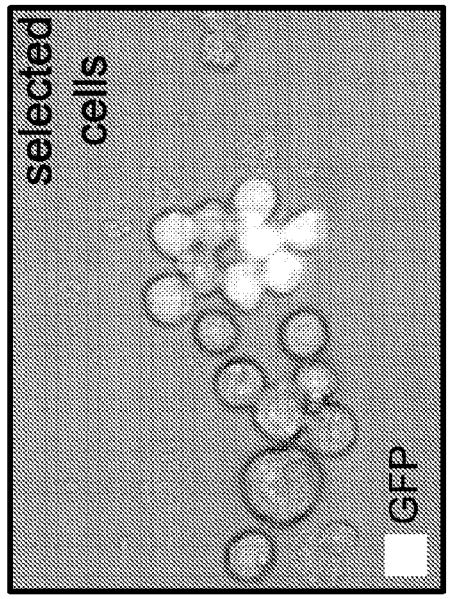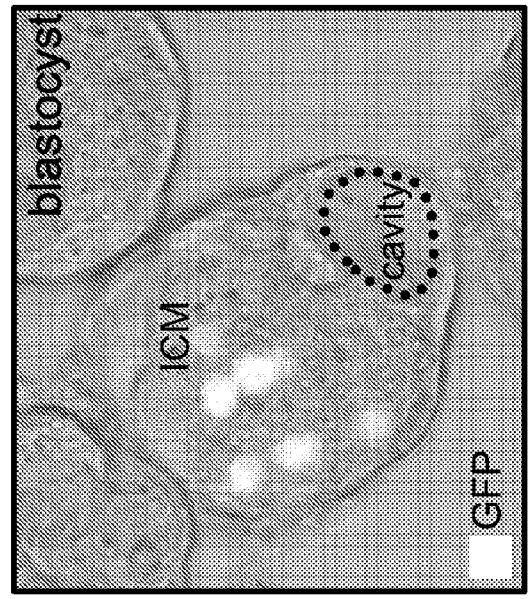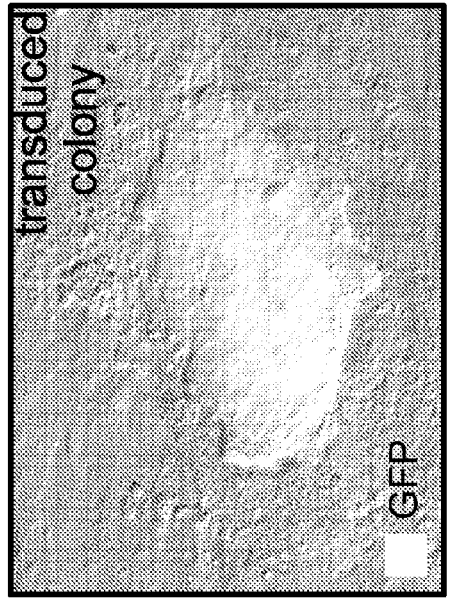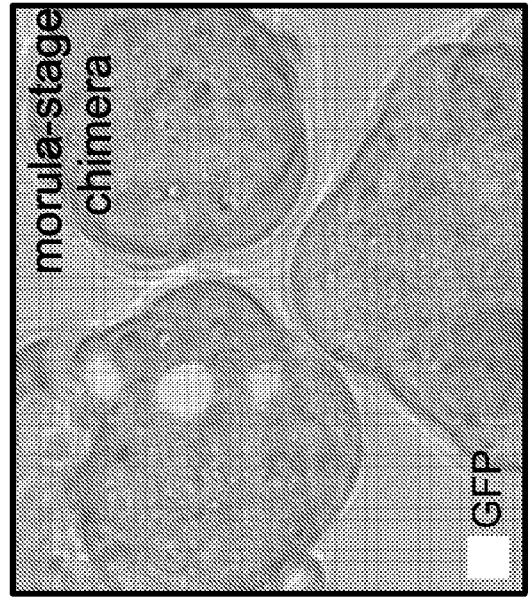
FIG. 28A
FIG. 28B
FIG. 28C
FIG. 28D

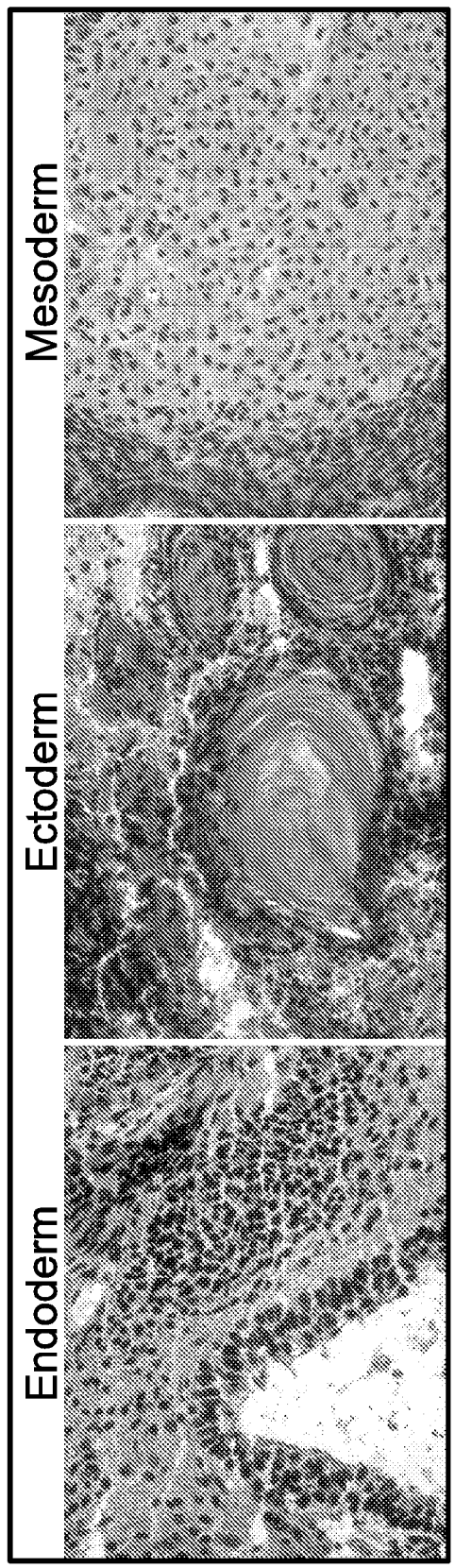
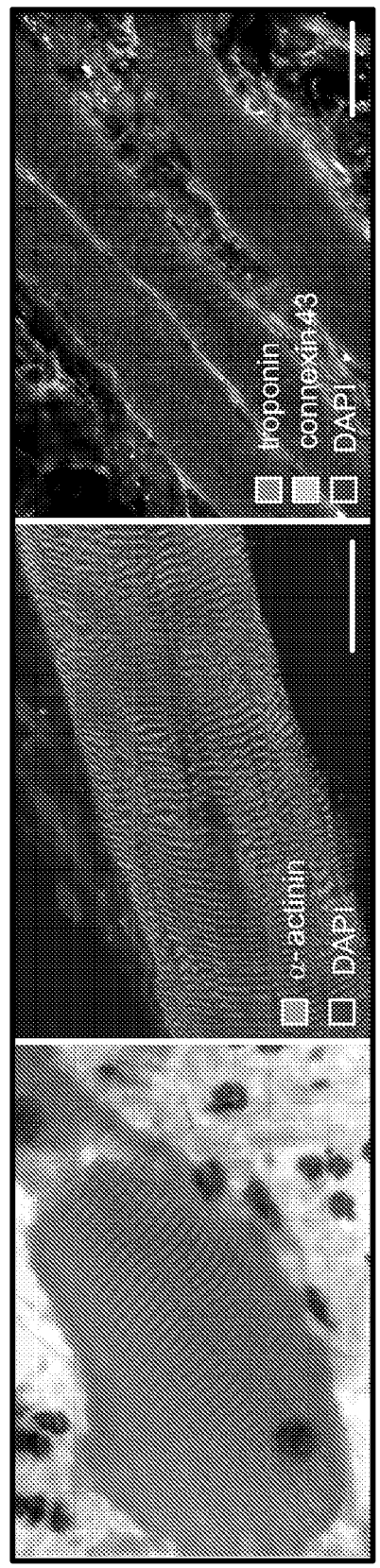
FIG. 31A
FIG. 31B

FIG. 33C                          FIG. 33D

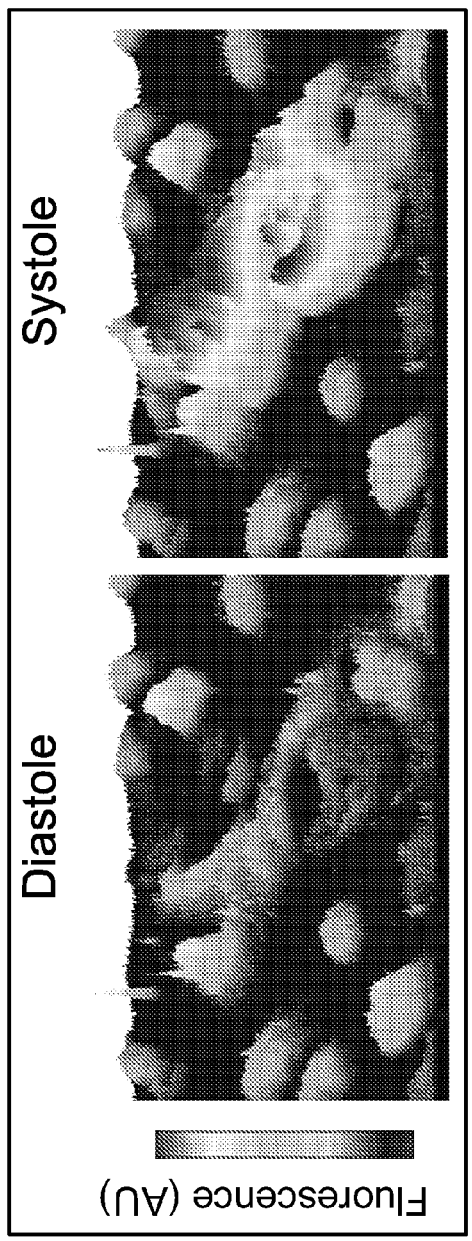
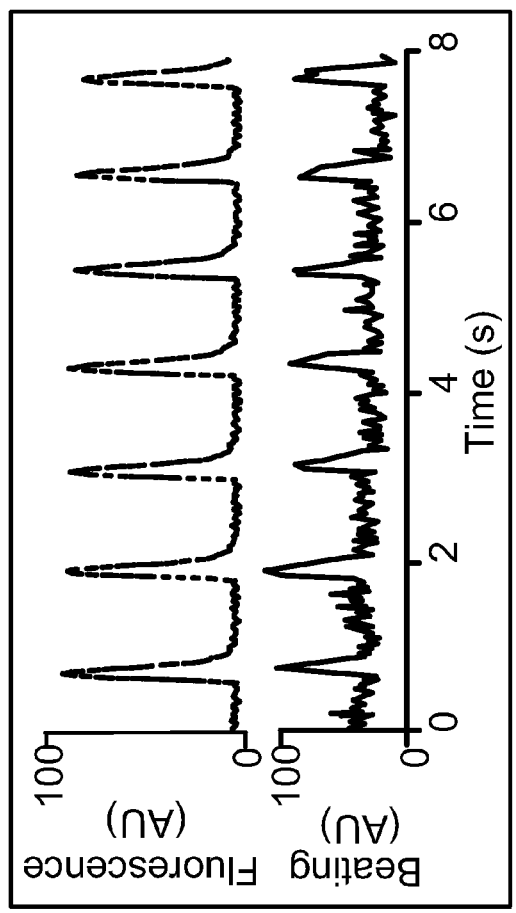
FIG. 34D
FIG. 34E

| Cellular | Embryonic |
|---|---|

METHOD OF TREATING HEART TISSUE USING INDUCED PLURIPOTENT STEM CELLS

STATEMENT AS TO FEDERALLY SPONSORED RESEARCH

This invention was made with government support under R01HL083439 and T32HL007111 awarded by National Institutes of Health. The government has certain rights in the invention.

CROSS-REFERENCE TO RELATED APPLICATIONS

This application is a National Stage application under 35 U.S.C. § 371 and claims the benefit under 35 U.S.C § 119(a) of International Application No. PCT/US2009/053314 having an International Filing Date of Aug. 10, 2009, which claims the benefit of priority to U.S. Provisional Application Ser. No. 61/273,654, filed Aug. 5, 2009; U.S. Provisional Application Ser. No. 61/271,341, filed Jul. 20, 2009; and U.S. Provisional Application Ser. No. 61/087,492, filed Aug. 8, 2008. The disclosures of the prior applications are considered part of (and are incorporated by reference in) the disclosure of this application.

BACKGROUND

1. Technical Field

This document relates to methods and materials involved in making and using induced pluripotent stem cells.

2. Background Information

Stem cells are characterized by the ability of self-renewal and differentiation into a diverse range of cell types. The two broad types of mammalian stem cells are embryonic stem (ES) cells and adult stem cells. Adult stem cells or progenitor cells replenish specialized cells to repair or maintain regenerative organs. Most adult stem cells are lineage-restricted and generally referred to by their tissue origin, such as adipose-derived stem cells. ES cell lines are derived from the epiblast tissue of the inner cell mass of a blastocyst or early morula stage embryos. ES cells are pluripotent and give rise to derivatives of the three germinal layers, i.e., the ectoderm, endoderm and mesoderm.

SUMMARY

This document provides methods and materials related to induced pluripotent stem cells. For example, this document provides induced pluripotent stem cells, compositions containing induced pluripotent stem cells, methods for obtaining induced pluripotent stem cells, and methods for using induced pluripotent stem cells (e.g., methods for using induced pluripotent stem cells to repair cardiovascular tissue). In some cases, the induced pluripotent stem cells and compositions containing induced pluripotent stem cells can be used to assess their therapeutic potential in appropriate animal models. For example, induced pluripotent stem cells of mouse origin that were created using human factors can be assessed in mice for therapeutic potential and for safety (e.g., the ability to not form cancerous cells).

In general, one aspect of this document features an induced pluripotent stem cell comprising nucleic acid encoding one or more polypeptides selected from the group consisting of a human Oct3/4 POU family polypeptide (e.g., a human Oct3/4 polypeptide), a human Sox family polypeptide, a human Klf family polypeptide, a human Myc family polypeptide, a human Nanog polypeptide, and a human Lin28 polypeptide, wherein the origin of the induced pluripotent stem cell is a non-human species. The non-human species can be selected from the group consisting of mouse, rat, hamster, guinea pig, rabbit, cat, dog, pig, sheep, goat, cow, horse, and monkey species. The induced pluripotent stem cell can be induced from a somatic cell. The somatic cell can be selected from the group consisting of skin, lung, heart, stomach, brain, liver, blood, kidney, and muscle cells. The human Sox family polypeptide can be a Sox2 polypeptide. The human Klf family polypeptide can be a Klf4 polypeptide. The human Myc family polypeptide can be a c-Myc polypeptide. The induced pluripotent stem cell can comprise nucleic acid encoding the human Oct3/4 POU family polypeptide (e.g., a human Oct3/4 polypeptide), the human Sox2 polypeptide, the human Klf4 polypeptide, and the human c-Myc polypeptide.

In another aspect, this document features an induced pluripotent stem cell comprising nucleic acid encoding one or more polypeptides selected from the group consisting of a non-human Oct3/4 POU family polypeptide (e.g., a non-human Oct3/4 polypeptide), a non-human Sox family polypeptide, a non-human Klf family polypeptide, a non-human Myc family polypeptide, a non-human Nanog polypeptide, and a non-human Lin28 polypeptide, wherein the origin of the induced pluripotent stem cell is human. The one or more polypeptides can be of mouse, rat, hamster, guinea pig, rabbit, cat, dog, pig, sheep, goat, cow, horse or monkey origin. The induced pluripotent stem cell can be induced from a human somatic cell. The human somatic cell can be selected from the group consisting skin, lung, heart, stomach, brain, liver, blood, kidney, and muscle cells. The non-human Sox family polypeptide can be a Sox2 polypeptide. The non-human Klf family polypeptide can be a Klf4 polypeptide. The non-human Myc family polypeptide can be a c-Myc polypeptide. The induced pluripotent stem cell can comprise nucleic acid encoding the non-human Oct3/4 POU family polypeptide (e.g., a non-human Oct3/4 polypeptide), a non-human Sox2 polypeptide, a non-human Klf4 polypeptide, and a non-human c-Myc polypeptide.

In another aspect, this document features an induced pluripotent stem cell, wherein the induced pluripotent stem cell was obtained using nucleic acid encoding one or more polypeptides selected from the group consisting of a human Oct3/4 POU family polypeptide (e.g., a human Oct3/4 polypeptide), a human Sox family polypeptide, a human Klf family polypeptide, a human Myc family polypeptide, a human Nanog polypeptide, and a human Lin28 polypeptide, wherein the origin of the induced pluripotent stem cell is a non-human species. The non-human species can be selected from the group consisting of mouse, rat, hamster, guinea pig, rabbit, cat, dog, pig, sheep, goat, cow, horse, and monkey species. The induced pluripotent stem cell can be induced from a somatic cell. The somatic cell can be selected from the group consisting of skin, lung, heart, stomach, brain, liver, blood, kidney, and muscle cells. The human Sox family polypeptide can be a Sox2 polypeptide. The human Klf family polypeptide can be a Klf4 polypeptide. The human Myc family polypeptide can be a c-Myc polypeptide. The induced pluripotent stem cell can comprise nucleic acid encoding the human Oct3/4 POU family polypeptide (e.g., a human Oct3/4 polypeptide), a human Sox2 polypeptide, a human Klf4 polypeptide, and a human c-Myc polypeptide.

In another aspect, this document features an induced pluripotent stem cell, wherein the induced pluripotent stem cell was obtained using nucleic acid encoding one or more polypeptides selected from the group consisting of a non-human Oct3/4 POU family polypeptide (e.g., a non-human Oct3/4 polypeptide), a non-human Sox family polypeptide, a non-human Klf family polypeptide, a non-human Myc family polypeptide, a non-human Nanog polypeptide, and a non-human Lin28 polypeptide, wherein the origin of the induced pluripotent stem cell is human. The one or more polypeptides can be of mouse, rat, hamster, guinea pig, rabbit, cat, dog, pig, sheep, goat, cow, horse or monkey origin. The induced pluripotent stem cell can be induced from a human somatic cell. The human somatic cell can be selected from the group consisting skin, lung, heart, stomach, brain, liver, blood, kidney, and muscle cells. The non-human Sox family polypeptide can be a Sox2 polypeptide. The non-human Klf family polypeptide can be a Klf4 polypeptide. The non-human Myc family polypeptide can be a c-Myc polypeptide. The induced pluripotent stem cell can comprise nucleic acid encoding the non-human Oct3/4 POU family polypeptide (e.g., a non-human Oct3/4 polypeptide), a non-human Sox2 polypeptide, a non-human Klf4 polypeptide, and a non-human c-Myc polypeptide.

In another aspect, this document features an induced pluripotent stem cell, wherein the induced pluripotent stem cell was obtained using a non-integrating vector comprising nucleic acid encoding one or more polypeptides selected from the group consisting of an Oct3/4 POU family polypeptide (e.g., a human Oct3/4 polypeptide), a Sox family polypeptide, a Klf family polypeptide, a Myc family polypeptide, a Nanog polypeptide, and a Lin28 polypeptide, wherein the induced pluripotent stem cell lacks the nucleic acid. The vector can be a viral vector. The vector can be a non-viral vector.

In another aspect, this document features a method for obtaining a population of induced pluripotent stem cells, wherein the method comprises (a) providing cells with nucleic acid encoding Oct3/4, Sox2, Klf4, and c-Myc polypeptides, and (b) culturing the cells with medium lacking serum under conditions to obtain the population of induced pluripotent stem cells. The medium can lack feeder cells. The medium can lack non-human feeder cells.

In another aspect, this document features a method for repairing diseased heart tissue in a mammal. The method comprises, or consists essentially of, administering induced pluripotent stem cells to the mammal under conditions wherein the diseased heart tissue is repaired, wherein the induced pluripotent stem cells were obtained using one or more polypeptides or nucleic acid encoding the one or more polypeptides selected from the group consisting of a Oct3/4 POU family polypeptide (e.g., a Oct3/4 polypeptide), a Sox family polypeptide, a Klf family polypeptide, a Myc family polypeptide, a Nanog polypeptide, and a Lin28 polypeptide. The administering step can comprise an intramyocardial administration. Progeny of the induced pluripotent stem cells can become engrafted into heart tissue of the mammal. Progeny of the induced pluripotent stem cells can become engrafted into heart tissue of the mammal without disrupting cytoarchitecture. The method can restore contractile performance, ventricular wall thickness, or electrical stability. The method can restore contractile performance, ventricular wall thickness, and electrical stability. The administering step can result in the regeneration of cardiac, smooth muscle, or endothelial tissue. The administering step can result in the regeneration of cardiac, smooth muscle, and endothelial tissue. In some cases, the induced pluripotent stem cells were induced from somatic cells. The somatic cells can be selected from the group consisting of skin, lung, heart, stomach, brain, liver, blood, kidney, and muscle cells. The Sox family polypeptide can be a human or non-human Sox2 polypeptide. The Klf family polypeptide can be a human or non-human Klf4 polypeptide. The Myc family polypeptide can be a human or non-human c-Myc polypeptide. The induced pluripotent stem cells can comprise nucleic acid encoding a human Oct3/4 POU family polypeptide (e.g., a human Oct3/4 polypeptide), a human Sox2 polypeptide, a human Klf4 polypeptide, and a human c-Myc polypeptide. The Oct3/4 POU family polypeptide can be a human Oct3/4 polypeptide. The Nanog polypeptide can be a human Nanog polypeptide. The Lin28 polypeptide can be a human Lin28 polypeptide. In some cases, the induced pluripotent stem cells were induced from human somatic cells.

In another aspect, this document features a method for regenerating cardiovascular tissue in a mammal. The method comprises, or consists essentially of, administering induced pluripotent stem cells to the mammal under conditions wherein progeny of the induced pluripotent stem cells become engrafted with cardiovascular tissue of the mammal, wherein the induced pluripotent stem cells were obtained using one or more polypeptides or nucleic acid encoding the one or more polypeptides selected from the group consisting of an Oct3/4 POU family polypeptide (e.g., a human Oct3/4 polypeptide), a Sox family polypeptide, a Klf family polypeptide, a Myc family polypeptide, a Nanog polypeptide, and a Lin28 polypeptide. The administering step can comprise an intramyocardial administration. The progeny can become engrafted into heart tissue of the mammal. The progeny can become engrafted into heart tissue of the mammal without disrupting cytoarchitecture. The method can restore contractile performance, ventricular wall thickness, or electrical stability. The method can restore contractile performance, ventricular wall thickness, and electrical stability. The administering step can result in the regeneration of cardiac, smooth muscle, or endothelial tissue. The administering step can result in the regeneration of cardiac, smooth muscle, and endothelial tissue. In some cases, the induced pluripotent stem cells were induced from somatic cells. The somatic cells can be selected from the group consisting of skin, lung, heart, stomach, brain, liver, blood, kidney, and muscle cells. The Sox family polypeptide can be a human or non-human Sox2 polypeptide. The Klf family polypeptide can be a human or non-human Klf4 polypeptide. The Myc family polypeptide can be a human or non-human c-Myc polypeptide. The induced pluripotent stem cells can comprise nucleic acid encoding a human Oct3/4 POU family polypeptide (e.g., a human Oct3/4 polypeptide), a human Sox2 polypeptide, a human Klf4 polypeptide, and a human c-Myc polypeptide. The Oct3/4 POU family polypeptide can be a human Oct3/4 polypeptide. The Nanog polypeptide can be a human Nanog polypeptide. The Lin28 polypeptide can be a human Lin28 polypeptide. In some cases, the induced pluripotent stem cells were induced from human somatic cells.

In another aspect, this document features a population of cardiomyoctes derived from induced pluripotent stem cells. The induced pluripotent stem cells were obtained using a human Oct3/4 POU family polypeptide (e.g., a human Oct3/4 polypeptide), a human Sox family polypeptide, and a human Klf family polypeptide or nucleic acid encoding the human Oct3/4 polypeptide, the human Sox family polypeptide, and the human Klf family polypeptide, wherein the origin of the induced pluripotent stem cell is human, and wherein the induced pluripotent stem cells were not contacted with an exogenous human c-Myc polypeptide. The induced pluripotent stem cell was induced from a human somatic cell. The human somatic cell can be selected from the group consisting skin, lung, heart, stomach, brain, liver, blood, kidney, and muscle cells. The human Sox family polypeptide can be a Sox2 polypeptide. The human Klf family polypeptide can be a Klf4 polypeptide. The induced pluripotent stem cell can comprise nucleic acid encoding the human Oct3/4 polypeptide, a human Sox2 polypeptide, and a human Klf4 polypeptide.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF THE DRAWINGS

FIG. 3 is a table providing the number of ES/iPS-like colonies formed after infection with HIV vectors expressing iPS-related factors.

FIGS. 25A-25H. Transduced murine fibroblasts with human stemness factors reactivate stem cell phenotype. (A) Control virus expressing GFP demonstrated no discernible changes in MEF morphology. (B) Coinfection with human OCT-3/4, SOX2, KLF4, and c-MYC vectors produced multiple colonies with distinct stem cell-like morphology that allowed isolation of individual clones. (C) Native MEFs continued to grow in monolayer and displayed contact inhibition at confluence. (D) Clonal expansion of transduced cells demonstrated morphology similar to embryonic stem cells. (E, F) Both native and transduced MEFs expressed markers of cell cycle activation indicated by Ki67 (cyan) in a subpopulation of progeny. (G, H) The stem cell marker SSEA1 was uniquely expressed within transduced cells compared with native MEFs identified by nuclear staining with DAPI.

FIG. 27. Multilineage in vivo differentiation within tumors. (A) Spontaneous in vivo differentiation was monitored in immunodeficient mice following subcutaneous injection by comparing native and transduced MEFs. (B) Tumor growth was detected only from sites injected with transduced cells after 1-2 weeks, followed by rapid expansion of tumor bulk, absent from native MEF injection sites. (C-F) Tissue was harvested at 4-6 weeks post injection. Cryosections and tissue staining demonstrated multiple lineages within the complex architecture of the nascent tumor and included muscle, keratin, glandular epithelium, and poorly differentiated tissues.

FIG. 28. Transduced cells integrate into host morula. (A, B) Transduced MEFs were labeled with GFP tag for tracking and allowed selection for ex utero integration into early-stage embryos. (C) Diploid aggregation between labeled transduced cells and normal morula produced chimeric early embryos. (D) Chimeric embryos developed into blastocysts, which displayed proper cavitation and formation of mosaic inner cell mass (ICM) with GFP-labeled blastomeres.

FIG. 31. Validated pluripotency of iPS according to in vivo differentiation. A, Fulfilling increasing levels of pluripotent stringency, 3F-iPS generated teratoma when injected subcutaneously into immunodeficient host. Tissues from the three germinal layers were identified by hematoxylin-eosin staining (40× magnification) represented by glandular epithelium (endoderm), keratinized epidermal ectoderm (ectoderm), and connective tissue (mesoderm). B, Cardiac tissue was found in teratomas derived from 3F-iPS as characterized by hematoxylin-eosin stained striations (left) and immunostaining for cardiac proteins α-actinin (middle), and troponin-I with connexin 43 (right). bar 10 μm. DAPI: 4,6'-diamidino-2-phenylindole.

DETAILED DESCRIPTION

Figure 1:
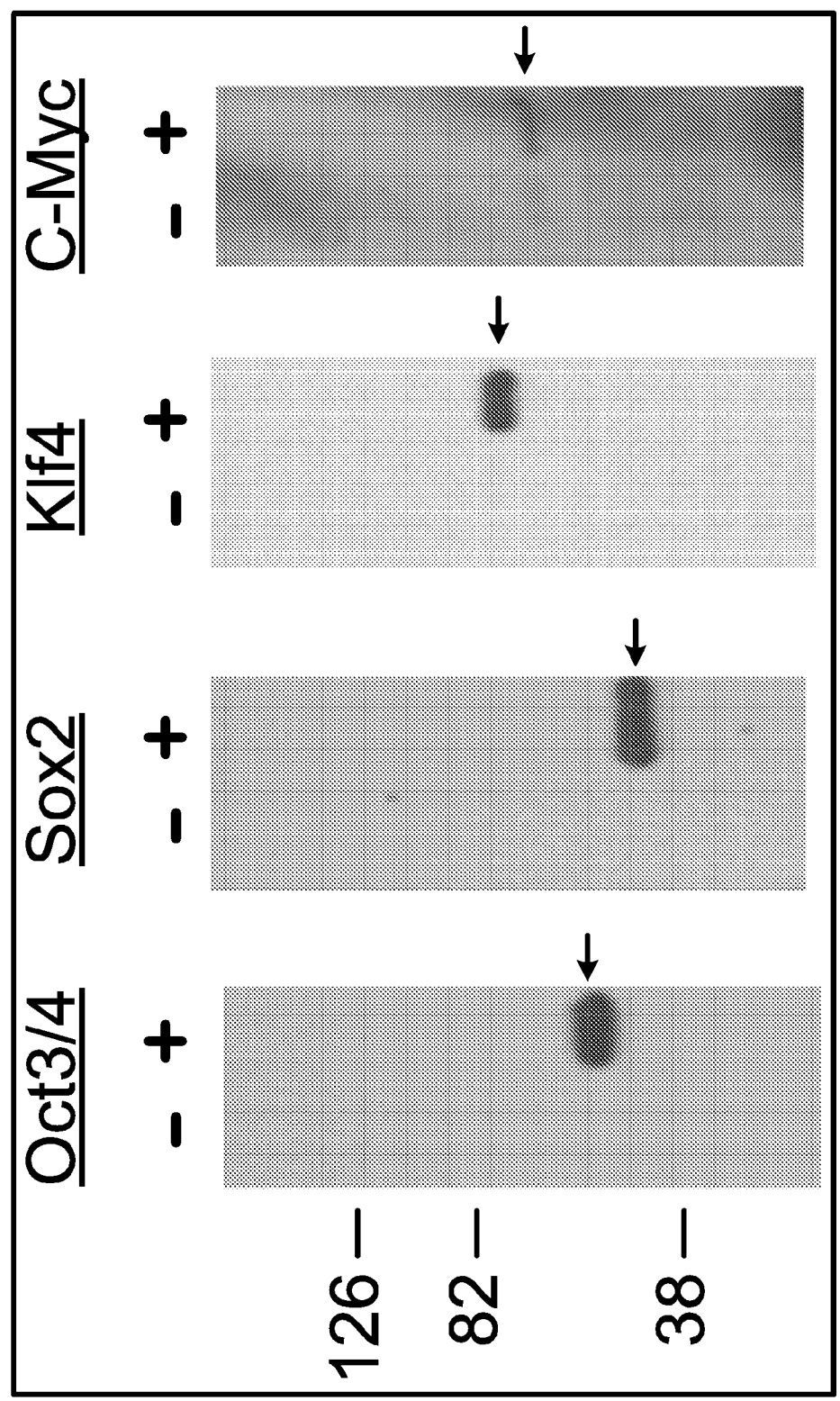
FIG. 1 is a photograph of a Western blot used to asses the generation of lentiviral vectors expressing stem cell-related genes. Oct3/4, Sox2, Klf4 and c-Myc expression was verified in the vector-infected 293T cells by immunoblotting with specific monoclonal antibodies.

This document provides methods and materials related to induced pluripotent stem cells. For example, this document provides induced pluripotent stem cells that were induced using polypeptides from a species that is different from the species from which the cells were obtained. An example of such induced pluripotent stem cells includes mouse cells that were induced to form induced pluripotent stem cells using human polypeptides. Other examples include rat, dog, cow, pig, and monkey (e.g., Rhesus monkey) cells that were induced to form induced pluripotent stem cells using human polypeptides. In some cases, an induced pluripotent stem cell provided herein can be a human cell that was induced to form an induced pluripotent stem cell using non-human polypeptides (e.g., polypeptides of mouse, rat, pig, dog, or monkey origin).

This document also provides induced pluripotent stem cells that were induced using polypeptides from a species that is the same species from which the cells were obtained. An example of such induced pluripotent stem cells includes human cells that were induced to form induced pluripotent stem cells using human polypeptides.

The polypeptides used to induce the formation of induced pluripotent stem cell can include any combination of Oct3/4 polypeptides, Sox family polypeptides (e.g., Sox2 polypeptides), Klf family of polypeptides (e.g., Klf4 polypeptides), Myc family polypeptides (e.g., c-Myc), Nanog polypeptides, and Lin28 polypeptides. For example, nucleic acid vectors designed to express Oct3/4, Sox2, Klf4, and c-Myc polypeptides can be used to obtain induced pluripotent stem cells. In some cases, Oct3/4, Sox2, Klf4, and c-Myc polypeptides can be directly delivered into target cells to obtain induced pluripotent stem cells using a polypeptide transfection method (e.g., liposome or electroporation). In one embodiment, nucleic acid vectors designed to express Oct3/4, Sox2, and Klf4 polypeptides, and not a c-Myc polypeptide, can be used to obtain induced pluripotent stem cells. In some cases, Oct3/4, Sox2, and Klf4 polypeptides can be directly delivered into target cells to obtain induced pluripotent stem cells using a polypeptide transfection method. An Oct3/4 polypeptide can have the amino acid sequence set forth in GenBank® Accession Numbers BC117435 (e.g., GI No. 109659099). An Sox2 polypeptide can have the amino acid sequence set forth in GenBank® Accession Numbers BC013923 (e.g., GI No. 33869633). A Klf4 polypeptide can have the amino acid sequence set forth in GenBank® Accession Numbers BC029923 (e.g., GI No. 20987475). A c-Myc polypeptide can have the amino acid sequence set forth in GenBank® Accession Numbers BC000141 (e.g., GI No. 12652778). A Nanog polypeptide can have the amino acid sequence set forth in GenBank® Accession Numbers BC099704.1 (e.g., GI No. 71043476). A Lin28 polypeptide can have the amino acid sequence set forth in GenBank® Accession Numbers BC028566 (e.g., GI No. 33872076).

Any appropriate cell type can be used to obtain induced pluripotent stem cells. For example, skin, lung, heart, liver, blood, kidney, or muscle cells can be used to obtain induced pluripotent stem cells. Such cells can be obtained from any type of mammal including, without limitation, humans, mice, rats, dogs, cats, cows, pigs, or monkeys. In addition, any stage of the mammal can be used, including mammals at the embryo, neonate, newborn, or adult stage. For example, fibroblasts obtained from an adult human patient can be used to obtain induced pluripotent stem cells. Such induced pluripotent stem cells can be used to treat that same human patient (or to treat a different human) or can be used to create differentiated cells that can be used to treat that same human patient (or a different human). For example, somatic cells from a human patient can be treated as described herein to obtain induced pluripotent stem cells. The obtained induced pluripotent stem cells can be differentiated into cardiomyocytes that can be implanted into that same human patient. In some cases, the obtained induced pluripotent stem cells can be directly administered to that same human patient.

Any appropriate method can be used to introduce nucleic acid (e.g., nucleic acid encoding polypeptides designed to induce pluripotent stem cells from cells) into a cell. For example, nucleic acid encoding polypeptides (e.g., Oct3/4, Sox2, Klf4, and c-Myc polypeptides) designed to induce pluripotent stem cells from other cells (e.g., non-embryonic stem cells) can be transferred to the cells using recombinant viruses that can infect cells, or liposomes or other non-viral methods such as electroporation, microinjection, transposons, phage integrases, or calcium phosphate precipitation, that are capable of delivering nucleic acids to cells. The exogenous nucleic acid that is delivered typically is part of a vector in which a regulatory element such as a promoter is operably linked to the nucleic acid of interest. The promoter can be constitutive or inducible. Non-limiting examples of constitutive promoters include cytomegalovirus (CMV) promoter and the Rous sarcoma virus promoter. As used herein, "inducible" refers to both up-regulation and down regulation. An inducible promoter is a promoter that is capable of directly or indirectly activating transcription of one or more DNA sequences or genes in response to an inducer. In the absence of an inducer, the DNA sequences or genes will not be transcribed. The inducer can be a chemical agent such as a protein, metabolite, growth regulator, phenolic compound, or a physiological stress imposed directly by, for example heat, or indirectly through the action of a pathogen or disease agent such as a virus.

Additional regulatory elements that may be useful in vectors, include, but are not limited to, polyadenylation sequences, translation control sequences (e.g., an internal ribosome entry segment, IRES), enhancers, or introns. Such elements may not be necessary, although they can increase expression by affecting transcription, stability of the mRNA, translational efficiency, or the like. Such elements can be included in a nucleic acid construct as desired to obtain optimal expression of the nucleic acids in the cells. Sufficient expression, however, can sometimes be obtained without such additional elements.

Vectors also can include other elements. For example, a vector can include a nucleic acid that encodes a signal peptide such that the encoded polypeptide is directed to a particular cellular location (e.g., the cell surface) or a nucleic acid that encodes a selectable marker. Non-limiting examples of selectable markers include puromycin, adenosine deaminase (ADA), aminoglycoside phosphotransferase (neo, G418, APH), dihydrofolate reductase (DHFR), hygromycin-B-phosphtransferase, thymidine kinase (TK), and xanthin-guanine phosphoribosyltransferase (XGPRT). Such markers are useful for selecting stable transformants in culture.

Any appropriate viral vectors can be used to introduce sternness-related factors, such as Oct3/4, Klf4, Sox2 and c-Myc. Examples of viral vectors include, without limitation, vectors based on DNA or RNA viruses, such as adenovirus, adeno-associated virus (AAV), retroviruses, lentiviruses, vaccinia virus, measles viruses, herpes viruses, baculoviruses, and papilloma virus vectors. See, Kay et al., *Proc. Natl. Acad. Sci. USA*, 94:12744-12746 (1997) for a review of viral and non-viral vectors. Viral vectors can be modified so the native tropism and pathogenicity of the virus has been altered or removed. The genome of a virus also can be modified to increase its infectivity and to accommodate packaging of the nucleic acid encoding the polypeptide of interest. In some cases, the induced pluripotent stem cells provided herein can be obtained using viral vectors that do not integrate into the genome of the cells. Such viral vectors include, without limitation, adenoviral vectors, AAV vectors, baculovirus vectors, and herpesvirus vectors. For example, cells obtained from a human can be provided nucleic acid encoding human Oct3/4, Sox2, Klf4, and c-Myc polypeptides using viral vectors that do not integrate the exogenous nucleic acid into the cells. Once the polypeptides are expressed and induced pluripotent stem cells are obtained, the induced pluripotent stem cells can be maintained in culture such that the induced pluripotent stem cells are devoid of the exogenous nucleic acid.

Any appropriate non-viral vectors can be used to introduce stemness-related factors, such as Oct3/4, Klf4, Sox2, and c-Myc. Examples of non-viral vectors include, without limitation, vectors based on plasmid DNA or RNA, retroelement, transposon, and episomal vectors. Non-viral vectors can be delivered to cells via liposomes, which are artificial membrane vesicles. The composition of the liposome is usually a combination of phospholipids, particularly high-phase-transition-temperature phospholipids, usually in combination with steroids, especially cholesterol. Other phospholipids or other lipids may also be used. The physical characteristics of liposomes depend on pH, ionic strength, and the presence of divalent cations. Transduction efficiency of liposomes can be increased by using dioleoylphosphatidylethanolamine during transduction. See, Felgner et al., *J. Biol. Chem.*, 269:2550-2561 (1994). High efficiency liposomes are commercially available. See, for example, SuperFect® from Qiagen (Valencia, Calif.).

In some cases, induced pluripotent stem cells can be obtained using culture conditions that do not involve the use of serum or feeder cells. For example, cells obtained from a human can be provided nucleic acid encoding human Oct3/4, Sox2, Klf4, and c-Myc polypeptides and cultured using media lacking serum (e.g., human or non-human serum) and lacking feeder cells (e.g., human or non-human feeder cells).

The invention will be further described in the following examples, which do not limit the scope of the invention described in the claims.

EXAMPLES

Example 1

Generating Mouse and Human iPS Cells Using Human Stem Cell-Associated Factors

The following studies were performed to establish effective methods for generating an iPS cell line capable of multilineage differentiation from somatic fibroblasts. These results include generating both mouse and human iPS cells using human stem cell-associated factors.

Generation of HIV vectors expressing stem cell-related factors. Human sequences were used to generate reprogramming vector sets that could be tested in evolutionary distant somatic cell types. Human factor cDNAs were amplified by PCR, and the PCR products were cloned into a HIV vector plasmid, pSIN-CSGWdlNotI vector, resulting in HIV-based lentiviral vectors encoding human Oct-3/4, Sox2, Klf4, c-Myc, Nanog, and Lin28. For improved transduction efficiency in mouse and rhesus cells, the modified HIV packaging construct with a H87Q Capsid mutation, pEx-QV, was used to produce infectious HIV vectors. After infection of human 293T cells with the infectious vectors, robust transgene expression was verified by immunoblotting with specific antibodies (FIG. 1).

Figure 2:
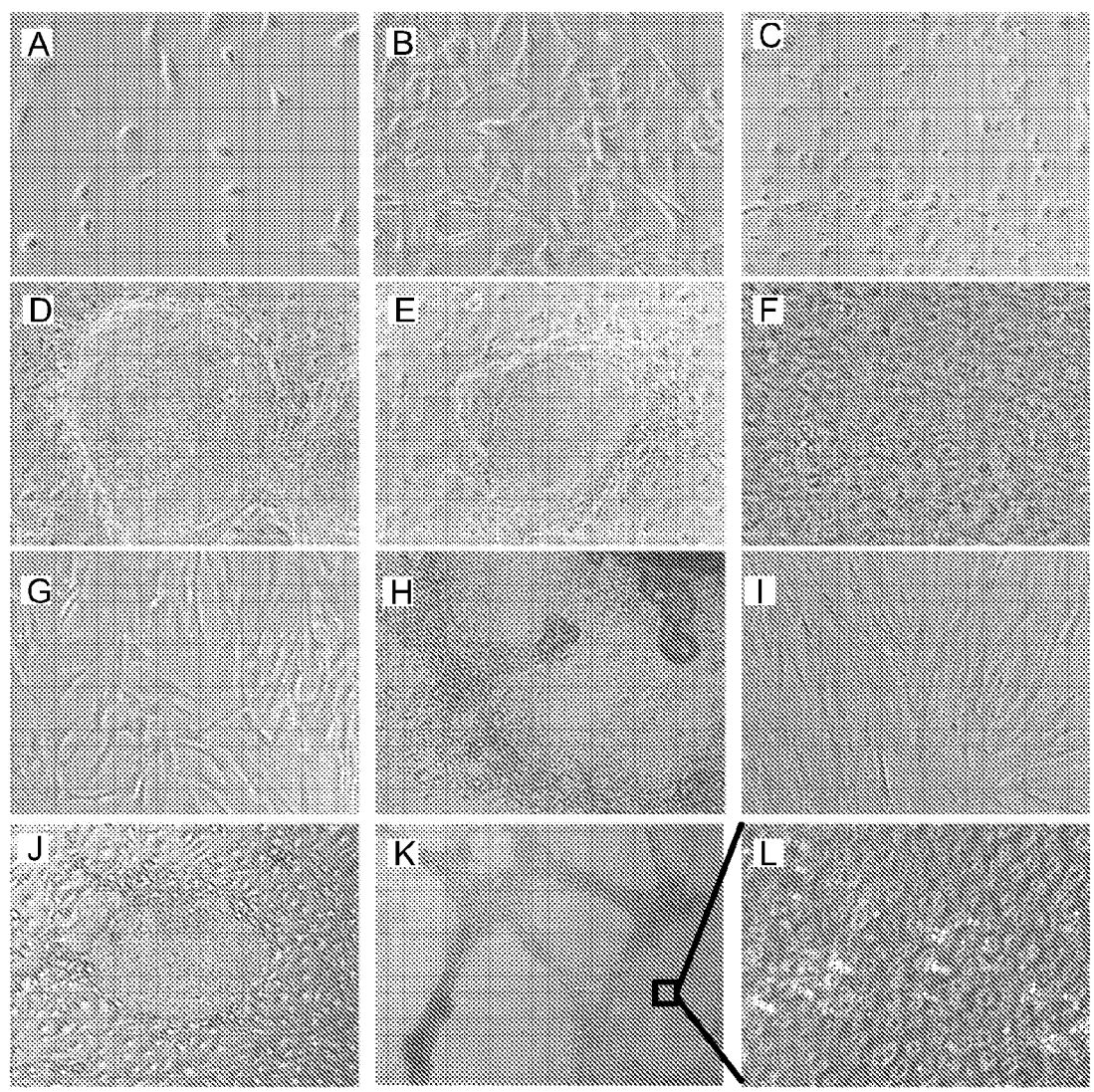
FIG. 2 contains photographs of cells demonstrating that lentiviral vector-mediated delivery of Oct3/4, Sox2, Klf4, and c-Myc results in ES-like colony formation. (A) Mouse SNL feeder cells. (B) Primary human cardiac fibroblasts (HCF). (C) Mitotically-inactivated SNL feeder cells after three weeks in culture. (D)(E) HCF-derived ES/iPS-like colonies. Colonies were flat and tightly packed. (F) Image of HCF-derived ES/iPS-like cells with high magnification. Each cell exhibited morphology similar to those of human ES and iPS cells, characterized by large nuclei and scant cytoplasm. (G) Human lung fibroblast MRC-5 cells. (H) Image of large MRC-5-derived ES/iPS-like colony. (I) Human foreskin fibroblasts BJ cells. (J) BJ-derived ES/iPS-like colony. (K) Image of a BJ-derived ES/iPS-like clone after expansion for three months in culture. (L) The BJ-derived ES/iPS-like cells with high magnification.

Ectopic expression of Oct3/4, Sox2, Klf4, and c-Myc in human somatic cells led to formation of iPS-like colonies. Human iPS cells form sharp-edged, flat, tightly-packed colonies similar to human ES cells, and express human ES-specific markers (Takahashi et al., *Cell*, 131:861-72 (2007) and Yu et al., *Science*, 318:1917-20 (2007)). Human somatic cells (primary cardiac fibroblasts HCF (ScienCell), foreskin-derived fibroblasts BJ (ATCC), fetal lung fibroblasts MRC-5 (ATCC)) were infected with different combinations of lentiviral vectors. Three weeks after co-cultivation with mouse feeder cells, ES/iPS-like colonies were observed in cells infected with Oct3/4, Sox2, Klf4, and c-Myc vectors (FIGS. 2 and 3), but not in untreated cells or cells treated with vectors expressing Oct3/4, Sox2, Klf4, Nanog, and Lin28 (FIG. 3).

Figure 4:
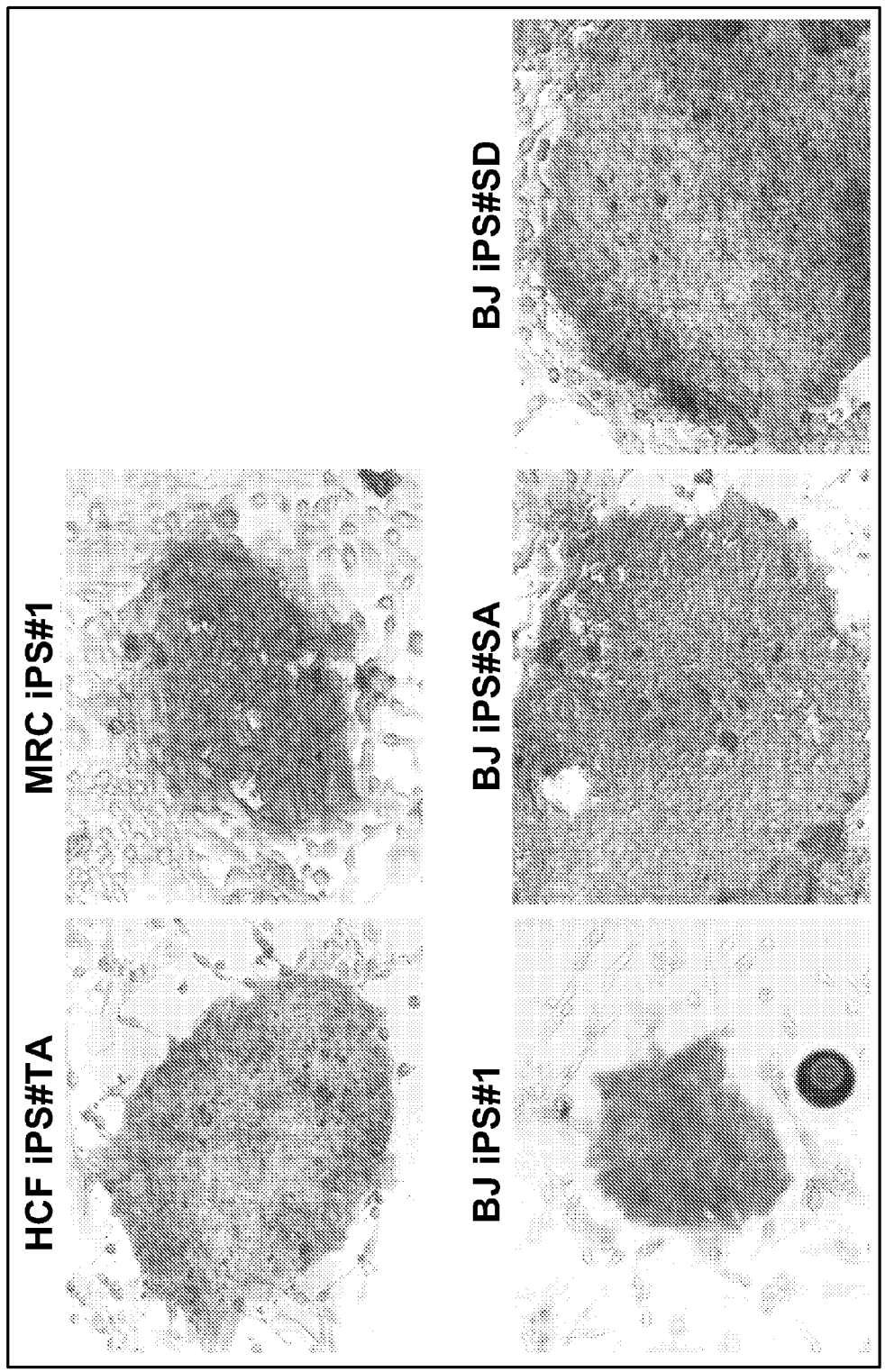
FIG. 4 contains photographs of putative human iPS colonies expressing alkaline phosphatase. All iPS-like colonies tested expressed alkaline phosphatase.
Figure 5:
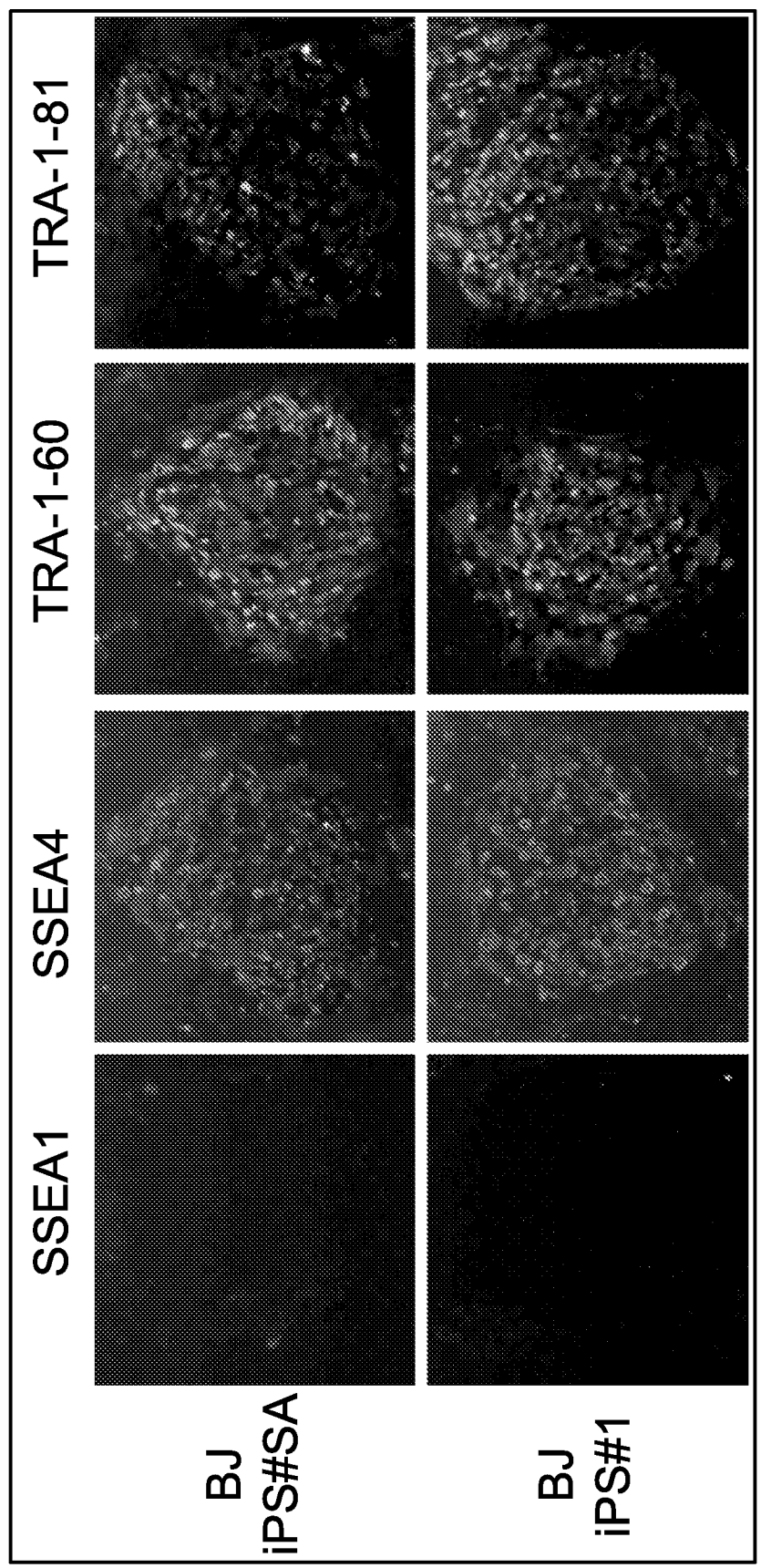
FIG. 5 contains photographs demonstrating an induced pluripotent phenotype from human fibroblasts. All iPS-like colonies tested expressed human ES/iPS markers, SSEA4, TRA-1-60, and TRA-1-81, but not SSEA1.

Putative human iPS clones express alkaline phosphatase and human ES/iPS-specific markers. Colonies selected for human ES/iPS-like morphology from HCF, BJ1 and MRC-5 cells were analyzed for alkaline phosphatase expression. Putative iPS clones, which were grown on feeder cells for three days, were fixed for one minute in 2% paraformaldehyde and then stained with the first red violet solution for 15 minutes at room temperature (Millipore, ES cell characterization kit). All putative human iPS clones tested expressed alkaline phosphatase (FIG. 4). Colonies also were analyzed by immunohistochemistry, detecting expression of human ES/iPS markers SSEA4, TRA-1-60, and TRA-1-81, but not SSEA1 (FIG. 5).

Figure 6:
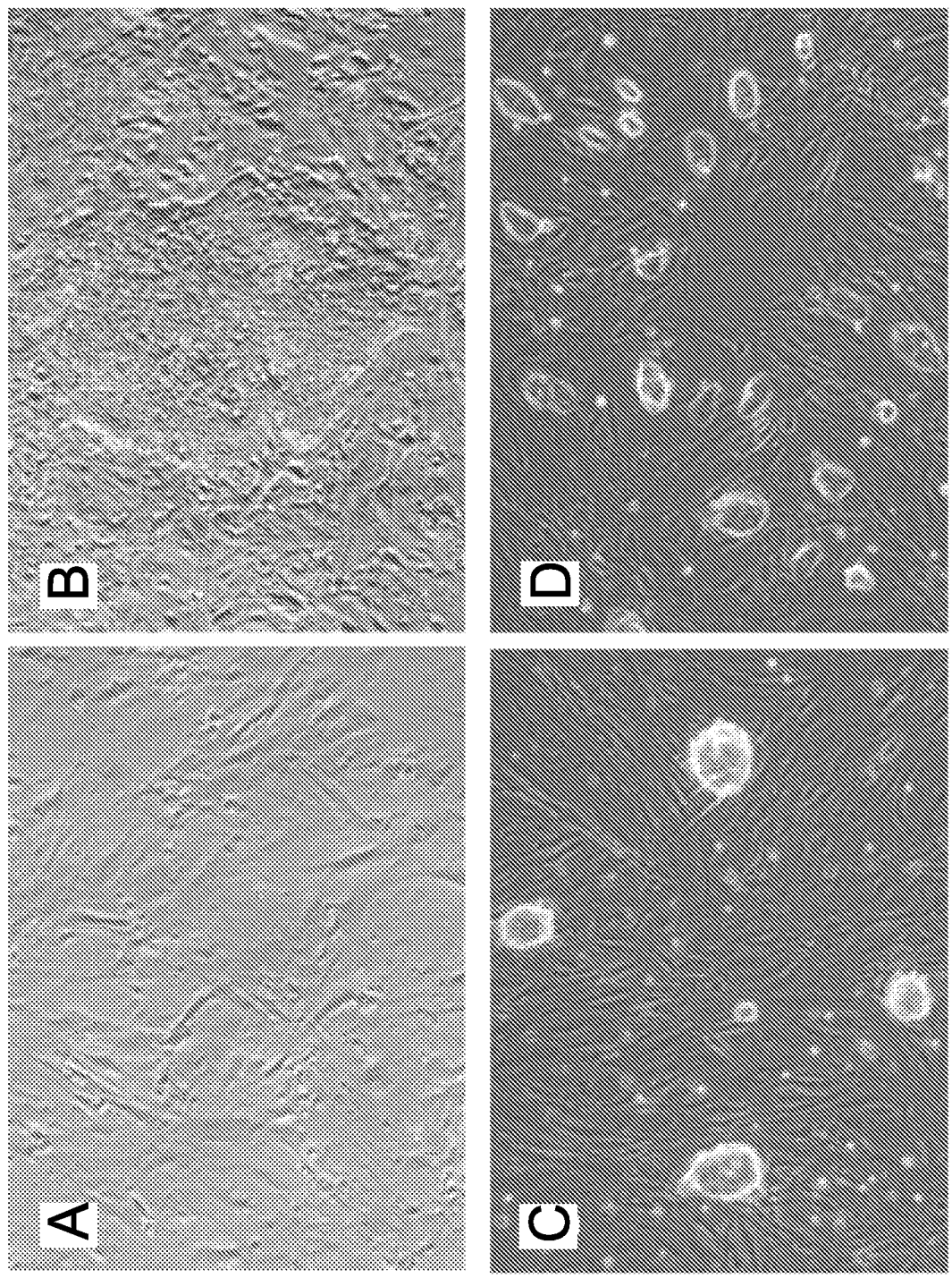
FIG. 6 contains photographs of mouse cells demonstrating that mouse iPS-like colonies can be derived from mouse embryonic fibroblasts. (A) Mouse embryonic fibroblast cells. (B) Tightly packed ES/iPS-like colonies were observed 10 days after vector transduction. (C) Single clone-derived iPS-like colonies. (D) Mouse ES cell colonies.
Figure 7:
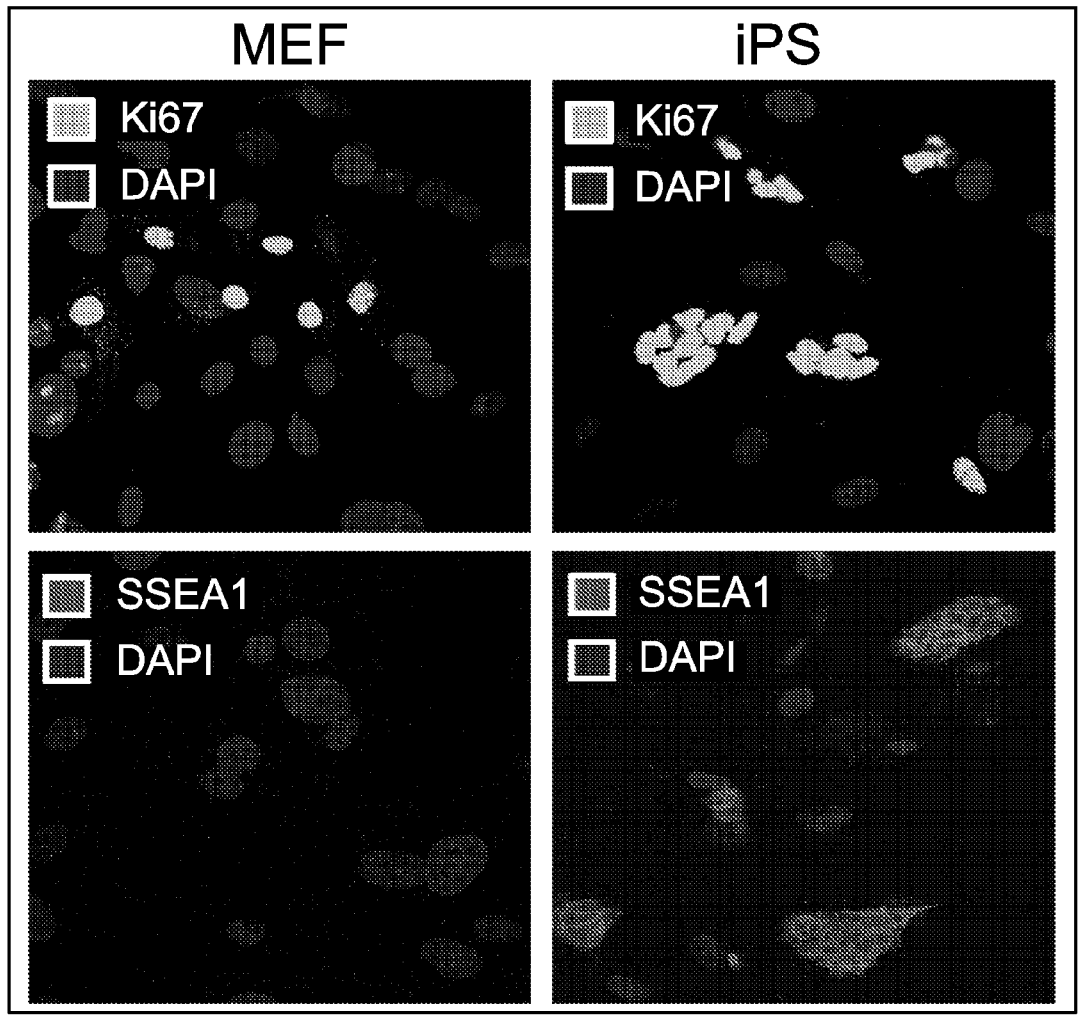
FIG. 7 contains images of induced pluripotent phenotype from mouse embryonic fibroblasts. MEF cells express Ki67 without SSEA-1 in the uninduced state. iPS cells derived from MEF's increase Ki67 expression and develop strong SSEA-1 expression.

Derivation of putative mouse iPS cells. When mouse embryonic fibroblasts were infected with four HIV vectors expressing human pluripotent genes, numerous (>500) mouse ES/iPS-like colonies were generated (FIG. 6). Following one week of co-culture with feeder cells, clonal expansion of selected colonies yielded progeny expressing the stem cell marker SSEA-1 (FIG. 7). In contrast to the original fibroblast source, derived iPS lines displayed ES-like morphology, and after six passages maintained expression of the pluripotent Oct4/Sox2 genes.

Derivation of mouse iPS-like colonies from adult mouse somatic cells. To test if human iPS-related factors can reprogram adult mouse somatic cells, mouse lung-, kidney-, tail-, and heart-derived cells from a six weeks old B16-GFP transgenic mouse and a factor VIII knockout mouse were infected with HIV vectors expressing human Oct3/4, Sox2, Klf4, and c-Myc. Numerous ES-like colonies were formed ten days after vector infection, especially in the lung-derived cells, and putative iPS clones were successfully expanded on mouse feeder cells.

Figure 8:
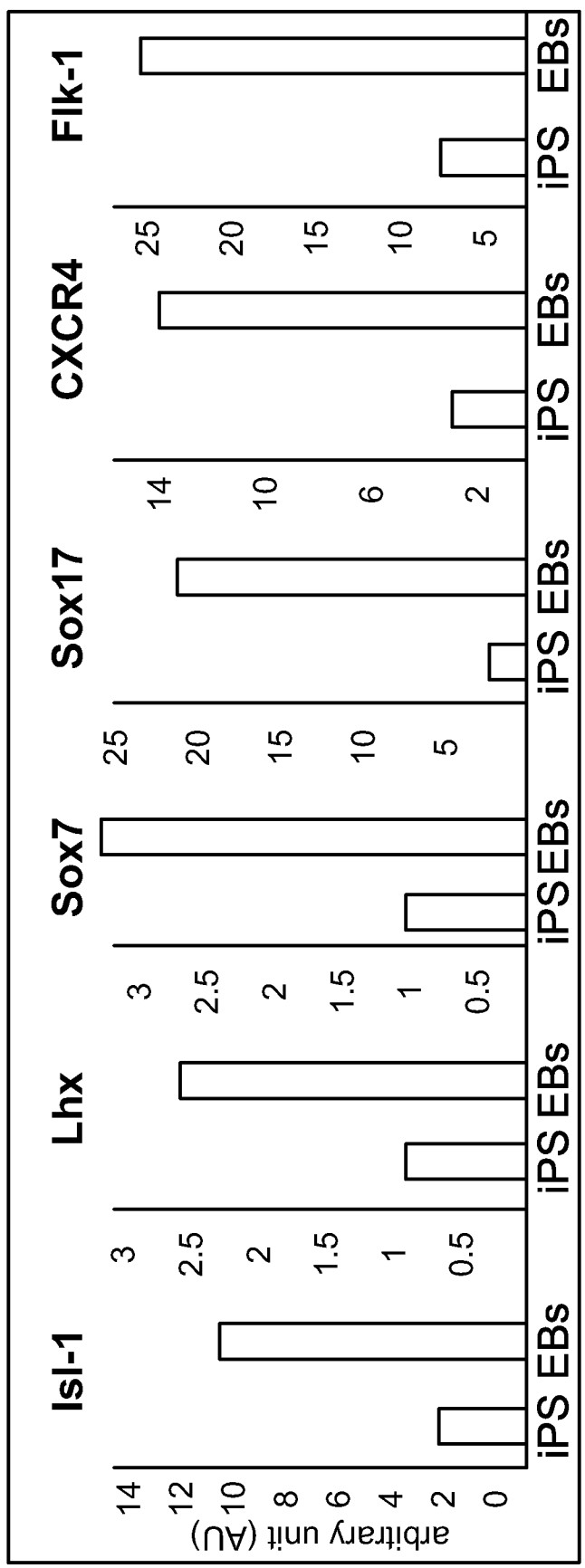
FIG. 8 is a graph plotting the expression of the indicated markers. EB in vitro differentiation revealed significant expression of markers of gastrulation, indicating formation of all three germ layers.

Expression of gastrulation during in vitro differentiation of iPS-derived embryoid body. In order to verify the pluripotency, the in vitro differentiation potential of the putative iPS cells was analyzed. An iPS clone was differentiated into embryoid bodies (EB), and the gastrulation markers in undifferentiated iPS cells and EB were examined by RT-PCR. Significant induction of gastrulation markers was evident in EB, indicating derivation of germ layers from transformed fibroblasts (FIG. 8).

In vitro differentiation of mouse iPS cells into embryoid bodies capable of rhythmic contractions. The putative iPS cells were tested for the ability to differentiate into cardiomyocytes. iPS-derived embryoid bodies were successfully differentiated into beating cardiomyocytes, evidence of the formation of contractile cardiomyocytes with pacemaker activity.

Figure 9:
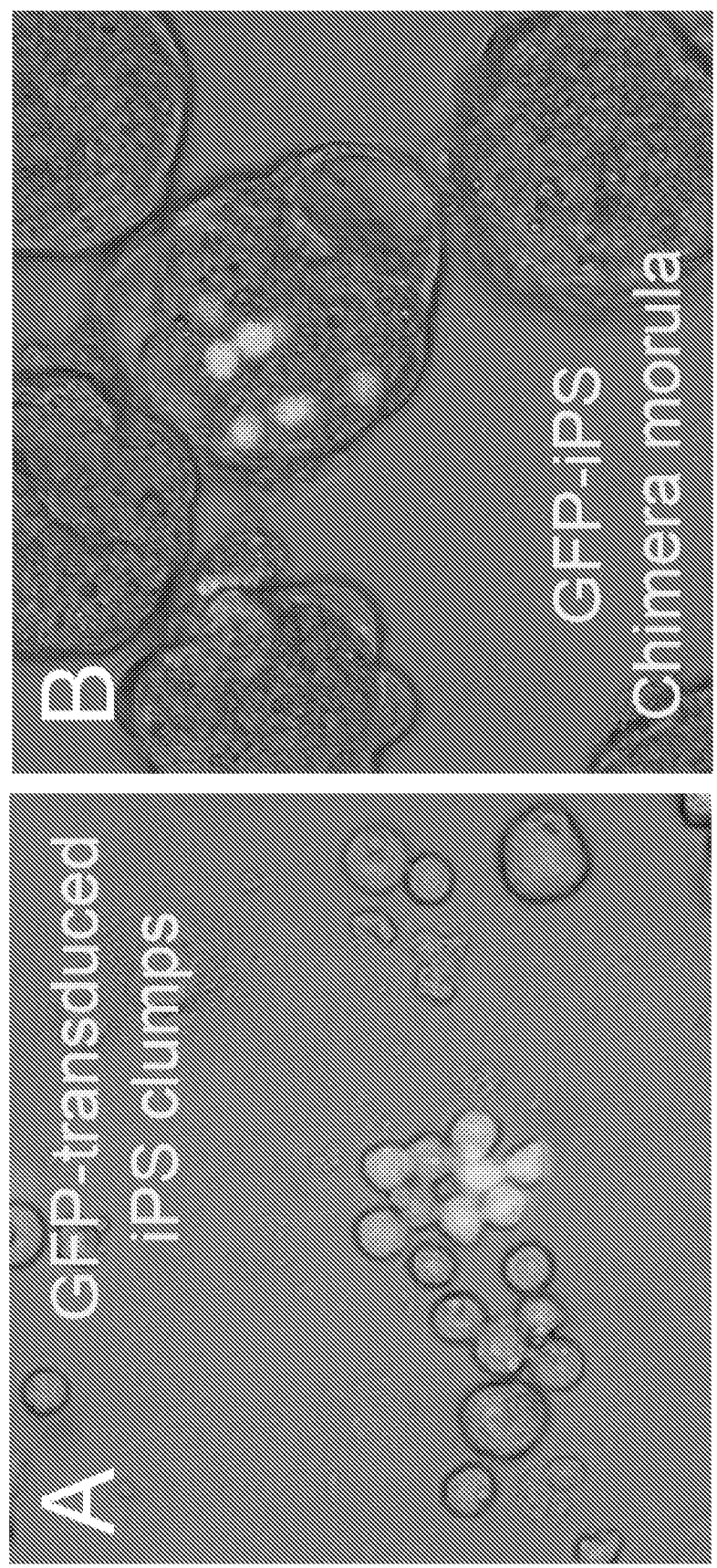
FIG. 9 contains photographs of iPS cell engraftment into host morula. (A) iPS cells were genetically labeled with GFP-expression tag and prepared as cell dumps. (B) Diploid aggregation with unlabeled morula stage embryo revealed incorporation into inner cell mass of the developing blastocytes.

Mouse iPS cell engraftment into host molura. A MEF-derived iPS clone was labeled with GFP by infecting the cells with a GFP-expressing HIV vector. GFP-labeled iPS cells were efficiently incorporated into developing morula to form a chimera blastocyte, a property limited to genuine ES cells (FIG. 9). Mosaic embryos are generated using GFP-labeled iPS cells in diploid aggregation for intrauterine transfer and subsequent embryonic development, and are used to characterize tissue-specific differentiation capacity of engineered iPS cells.

Figure 10:
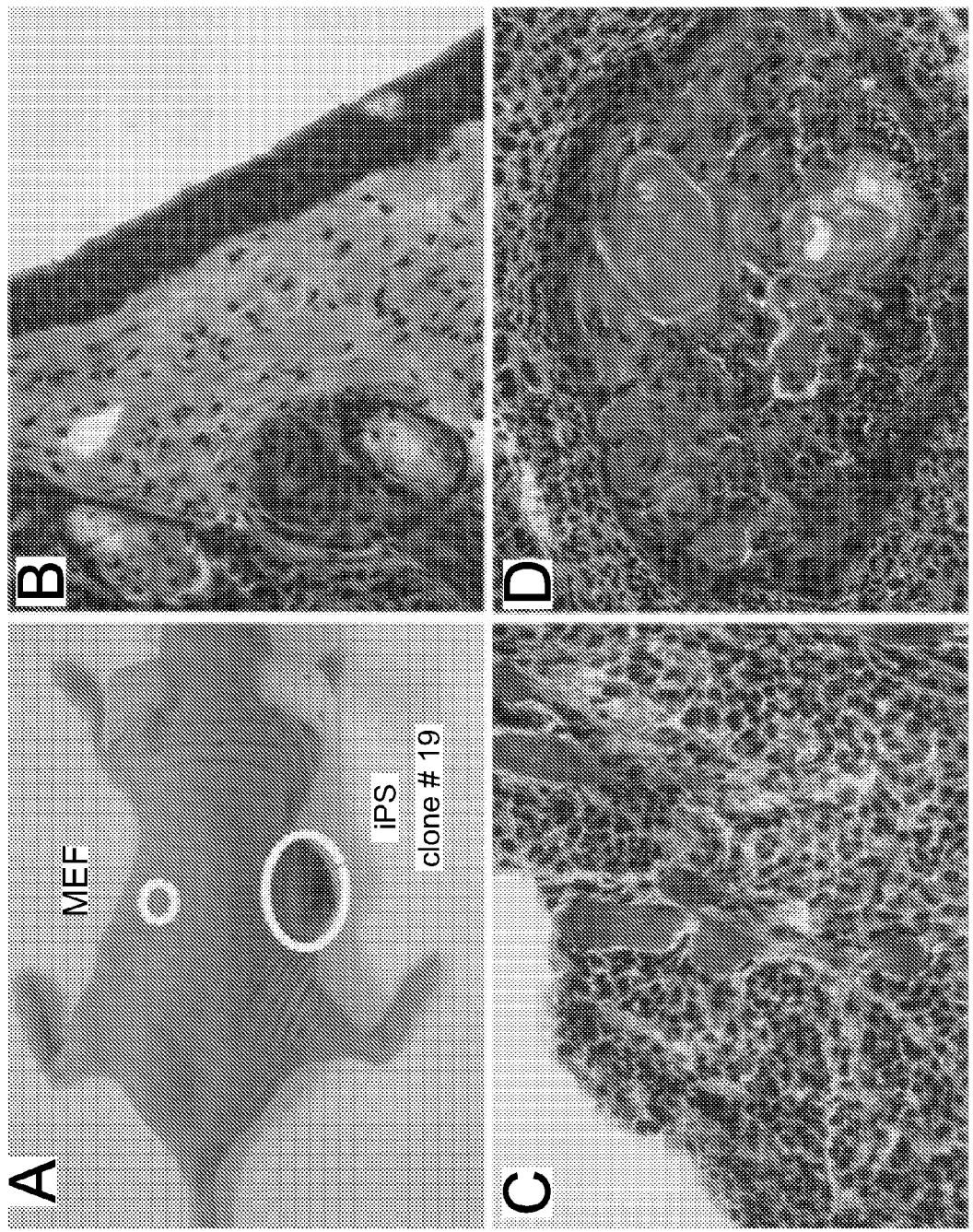
FIG. 10 contains photographs demonstrating the in vivo differentiation of mouse iPS cells into teratoma-like masses. (A) Four weeks after subcutaneous injection of a mouse iPS clone in a nude mouse resulted in formation of teratoma-like masses. (B)(C)(D) HE staining revealed typical multi-lineage tissue differentiation.

Xenografts of iPS cells in nude mice generate teratoma-like masses. Human and mouse ES cells form teratomas after cell injection into immunodeficient mice, an assay that has become the accepted standard for demonstrating their developmental pluripotency. Immunodeficient mice were subcutaneously injected with mouse iPS clones or parental MEF cells. Injection of 500,000 iPS cells resulted in formation of a subcutaneous tumor that enlarged to 1 cm diameter within 4 weeks (FIG. 10). Histology of mass revealed complex cellular architecture consistent with diverse lineage differentiation of a teratoma (FIG. 10). Tissue-specific immunostaining is performed to characterize cytotypes fully.

Figure 11:
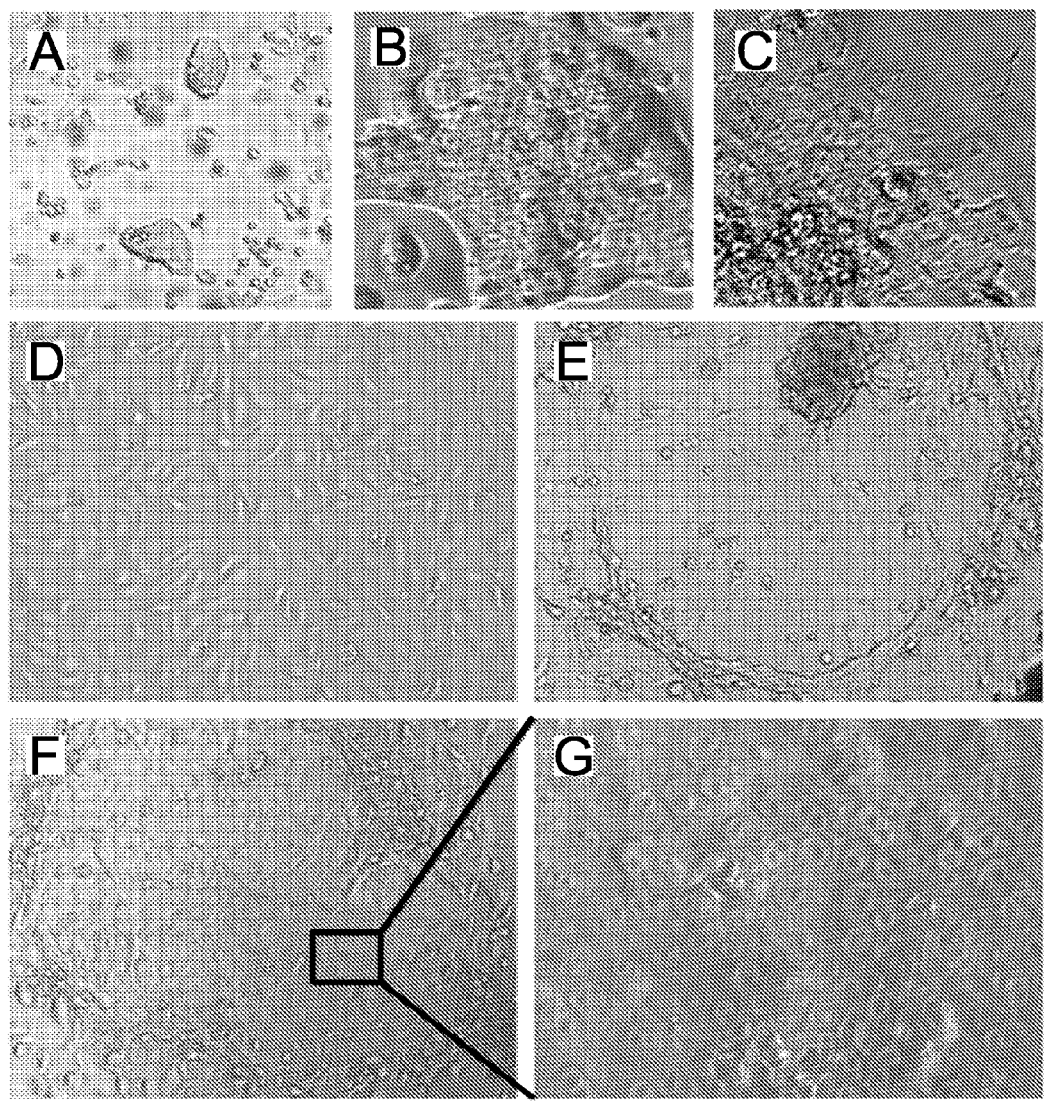
FIG. 11 contains photographs demonstrating the generation of putative iPS cells from rat, hamster, and rhesus monkey cells. (A) Rat iPS-like colonies. (B) Rat iPS-like colonies (higher magnification). (C) Chinese hamster-derived iPS-like colonies (higher magnification). (D) Parental Rhesus kidney-derived cell line. (E) and (F) Rhesus monkey iPS-like colonies. (G) Image of rhesus iPS-like cells with high magnification. Each cell exhibited morphology similar to those of human iPS cells, characterized by large nuclei and scant cytoplasm.

Derivation of putative iPS cells from rat cells. The ability of human iPS-related factors to reprogram rat somatic cells into ES-like progeny was tested. Normal rat kidney cells were infected with HIV vectors expressing human Oct3/4, Sox2, Klf4, and c-Myc. Vector-infected cells were co-cultured with mouse SNL feeder cells for eight days. Many iPS-like colonies were observed, and 12 colonies were picked for further characterization. Only two of the 12 colonies maintained the iPS-like morphology for two weeks in the presence of mouse LIF (FIG. 11). iPS-like colonies were also formed in the Chinese hamster cells following transduction by the four human factor-expressing vectors (FIG. 11).

Derivation of putative iPS cells from rhesus monkey cells. Rhesus monkey kidney derived cells were infected with HIV vectors expressing human Oct3/4, Sox2, Klf4, and c-Myc. Vector-infected cells were co-cultured with mouse SNL feeder cells for ten days in serum-free media (HuESGro, Millipore) supplemented with human b-FGF. Six putative rhesus monkey iPS clones with sharp-edged, flat and tightly-packed colonies similar to human iPS cells were identified (FIG. 11).

These results demonstrate the feasibility of reprogramming of human and mouse cells with defined human factors. For example, these results demonstrate that HIV vectors expressing human Oct3/4, Sox2, Klf4, c-Myc, Nanog, and Lin28 can be used to derivate iPS cells from rat, dog, and rhesus monkey cells, thereby allowing appropriate efficacy and toxicology testing of autologous iPS cells in appropriate animal models.

Efficient iPS derivation from experimental animals can enable preclinical efficacy testing of autologous iPS cells in proper models. Use of the vectors expressing human stem cell factors can allow direct toxicology testing of the same vectors used in human trials.

Figure 12:
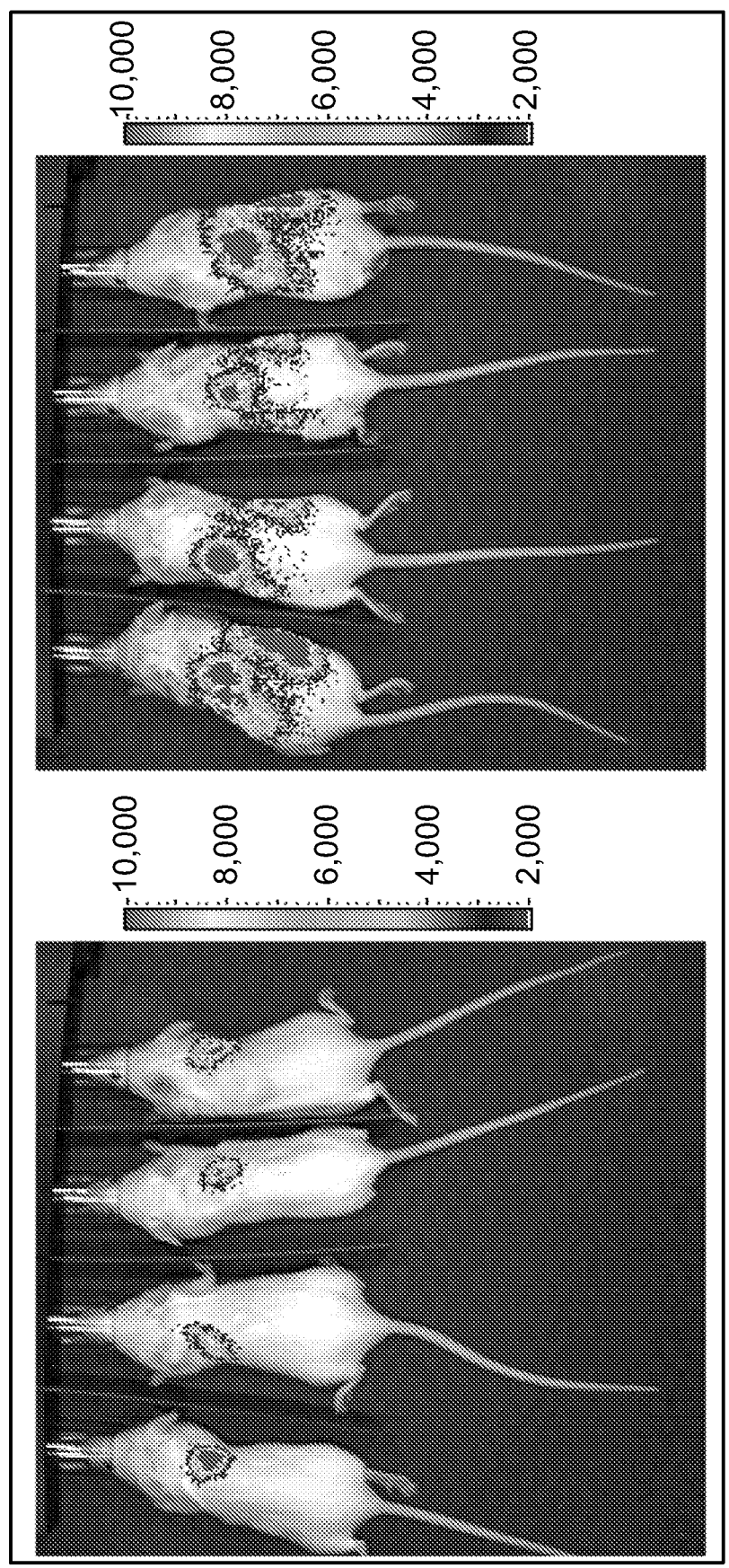
FIG. 12 contains photographs of non-invasive live imaging of HIV vector-infected cells. Luciferase-expressing HIV vector-infected cells were monitored by Xenogen IVIS imaging machine. Left panel: 1 week after subcutaneous administration of Luciferase-expressing HIV vector. Right panel: 1 week after intravenous administration of the same vector.

The influence of systemic administration of autologous iPS cells in mice and rats can be examined. For example, autologous iPS cells can be genetically label with Luciferase, GFP, and LacZ with HIV vectors, and their in vivo distribution (examples of live-imaging are shown in FIG. 12) can be monitored. Where the cells migrate, how they differentiate in vivo, and whether they form teratomas in immunocompetent hosts can be determined. The biodistribution of iPS cells in healthy and diseased animals can be compared. In addition, the therapeutic effects of autologous iPS injection into myocardial infarction-induced mouse and rat models can be tested. These studies can be expanded in dog, pig, and rhesus monkey heart disease models.

Example 2

Reprogramming Mouse Fibroblast Cells Using Lentiviral Vectors Expressing Human Oct3/4, Sox2, Klf4, and c-Myc The following is performed to further characterize the ability of human factors to reprogram mouse fibroblast cells into iPS cells. Fibroblasts are isolated from a GFP transgenic C57/BL6 mouse tail. $5 \times 10^4$ cells are infected with HIV vectors expressing human Oct3/4, Sox2, Klf4, and c-Myc at multiplicity of infection of 10. Transduced cells are cultured in the normal growth medium for fibroblast cells for four days, and then are spread in a 10-cm plate on a mouse SNL feeder cells. One day after the passage, culture supernatants are changed to LIF -and FCS-containing ES media. One third of the culture supernatants are replaced daily. The cells are monitor for up to 3 weeks. 24 iPS-like colonies are picked up for expansion. The remaining cells on the 10-cm plates are fixed by 4% paraformaldehyde for one min, are treated with freshly prepared first red substrate for AP staining (Millipore) for 15 minutes at room temperature, and then are counted for the number of iPS-like colonies.

The 24 clonal iPS-like cells are expanded, and their authenticity is screened by mouse ES/iPS-specific marker SSEA1 and alkaline phosphatase expression. Five iPS-like colonies with strong SSEA and alkaline phosphatase expression are further characterized to demonstrate the pluripotency. The clones are examined for the telomerase activity (TRAPEZE telomerase kit), in vitro differentiation through embryoid bodies (EB), pluripotency-associated gene expression, and the ability to form teratomas and are used to generate chimeric mice.

Mouse ES and iPS culture. Mouse ES and iPS cells are maintained in Glasgow's Minimum Essential Medium (Bio-Whittaker-Cambrex) supplemented with pyruvate and L-glutamine (Cellgro), non-essential amino acids (Cellgro), β-mercaptoethanol (Sigma-Aldrich), 10% FCS (Invitrogen), and leukemia inhibitory factor (Chemicon International).

EB formation. Mouse iPS cells are differentiated into three-layer embryoid bodies using the hanging-drop method in differentiation media supplemented with 20% FCS and TNF-α (Invitrogen) as described elsewhere (Nelson et al., *Stem Cells*, 26:1464-73 (2008)). In vitro differentiation of mouse iPS cells into embryoid bodies capable of rhythmic contractions is performed as described elsewhere (Nelson et al., *Stem Cells*, 26:1464-73 (2008)).

Cells. 293T (ATCC), MRC-5 (ATCC), BJ (ATCC) and SNL feeder cells (MMRRC) are maintained in Dulbecco's modified Eagle medium (DMEM) supplemented with 10% FCS and antibiotics. Primary mouse, rat, dog, and pig fibroblast cells are cultured in DMEM supplemented with 10% fetal calf serum (FCS) and antibiotics.

HIV-based vectors. HIV-based vectors are prepared by transfection of 293T cells with three plasmids, pMD-G, pEx-QV, and stem cell-related gene-expressing vector plasmid, as described elsewhere (Ikeda et al., *Gene Ther.*, 9:932-8 (2002); Ikeda et al., *Nat. Biotechnol.*, 21:569-72 (2003); Strang et al., *Gene Ther.*, 11:591-8 (2004); and Sakuma et al., *Gene Ther.*, 14:185-9 (2007)).

Immunostaining. Immunostaining to detect cell surface markers is performed as described elsewhere (Noser et al., *Mol. Ther.*, 15:1531-6 (2007) and Palmowski et al., *J. Immunol.*, 172:1582-7 (2004)).

Example 3

Reprogramming Somatic Cells from Rat, Dog, Pig, and Rhesus Monkey Cells

The following is performed to further characterize the generation of iPS cells from diverse species with vectors expressing defined human stem cell-related factors. Rat and pig lung-derived primary cells (less than 5 passages) and dog cardiac fibroblast cells are used to derive rat, dog, and pig iPS cells. Rhesus monkey lung-derived fibroblast cells (DBL-FRhL-2, ATCC CL-160), fetal epithelial cells (FrhK4, ATCC CRL-1688), primary peripheral blood monocytes (Dr. DeRavin, NIAID) and primary hepatocytes (Celsis Invitro Technologies) are used to derive iPS cells from rhesus monkey. $5 \times 10^4$ cells are infected with various combinations of HIV vectors expressing human Oct3/4, Sox2, Klf4, c-Myc, Nanog, and Lin28 at multiplicity of infection of 10. Transduced cells are cultured in the normal growth medium for fibroblast cells for 4 days, and then are spread in a 10-cm plate on a mouse SNL feeder cells. One day after the passage, the medium is changed to specific ES media (Table 1). For rat iPS cell derivation, mouse ES media supplemented with 1000 units of rat LIF (Millipore) is used. For dog and pig iPS cell derivation, mouse ES media supplemented with mouse LIF (Chemicon International) and human LIF (Millipore) are used, respectively. For rhesus monkey iPS cells, b-FGF-containing HuESGRo medium is used. One third of the culture supernatants are replaced daily. The cells are monitored for up to 3 weeks. 24 iPS-like colonies are picked up for expansion. The remaining cells on the 10-cm plates are fixed by 4% paraformaldehyde for 1 minute, treated with freshly prepared first red substrate for AP staining (Millipore) for 15 minutes at room temperature, and then counted for the number of iPS-like colonies.

TABLE 1

ES Cell Markers and cytokines use to maintain the cells.

|  | Mouse | Rat | Dog | Pig* | Cow* | Rh | Hu |
|---|---|---|---|---|---|---|---|
| SSEA1 | ✓ | ✓ | ✓ | ✓ |  |  |  |
| SSEA-3 |  |  |  |  |  | ✓ | ✓ |
| SSEA-4 |  |  |  |  | ✓ | ✓ | ✓ |
| TRA-1-60 |  |  |  |  |  | ✓ | ✓ |
| TRA-1-81 |  |  |  |  |  | ✓ | ✓ |
| Oct4 | ✓ | ✓ | ✓ | ✓ | ✓ | ✓ | ✓ |
| APtase | ✓ | ✓ | ✓ | ✓ | ✓ | ✓ | ✓ |
| Growth factor | mLIF | mLIF | mLIF | hLIF | hLIF hEGF | hLIF | bFGF |

*Porcine and Bovine ES-like cells

The 24 clonal iPS-like cells are expanded, and their authenticity screened by mouse ES/iPS-specific marker and alkaline phosphatase expression. Five iPS-like colonies with strong SSEA1 (SSEA4 for rhesus iPS cells) and alkaline phosphatase expression are further characterized to demonstrate the pluripotency. The clones are examined for the telomerase activity (TRAPEZE telomerase kit), in vitro differentiation through EB, pluripotency-associated gene expression, and teratoma formation.

Rat, dog, and pig iPS culture. Mouse ES/iPS media is used with rat LIF, human LIF, or mouse LIF for rat, dog, and pig iPS cells, respectively.

Rhesus monkey iPS culture. Human iPS cells are maintained in serum-free HESGro medium (Millipore) supplemented with basic fibroblast growth factor (8 ng/mL).

Cells. 293T (ATCC), MRC-5 (ATCC), BJ (ATCC) and SNL feeder cells (MMRRC) are maintained in Dulbecco's modified Eagle medium (DMEM) supplemented with 10% FCS and antibiotics. Primary mouse, rat, dog, and pig fibroblast cells are cultured in DMEM supplemented with 10% fetal calf serum (FCS) and antibiotics.

HIV-based vectors. HIV-based vectors are prepared by transfection of 293T cells with three plasmids, pMD-G, pEx-QV, and stem cell-related gene-expressing vector plasmid, as described elsewhere (Ikeda et al., *Gene Ther.*, 9:932-8 (2002); Ikeda et al., *Nat. Biotechnol.*, 21:569-72 (2003); Strang et al., *Gene Ther.*, 11:591-8 (2004); and Sakuma et al., *Gene Ther.*, 14:185-9 (2007)).

Immunostaining. Immunostaining to detect cell surface markers is performed as described elsewhere (Noser et al., *Mol. Ther.*, 15:1531-6 (2007) and Palmowski et al., *J. Immunol.*, 172:1582-7 (2004)).

Example 4

Figure 13:
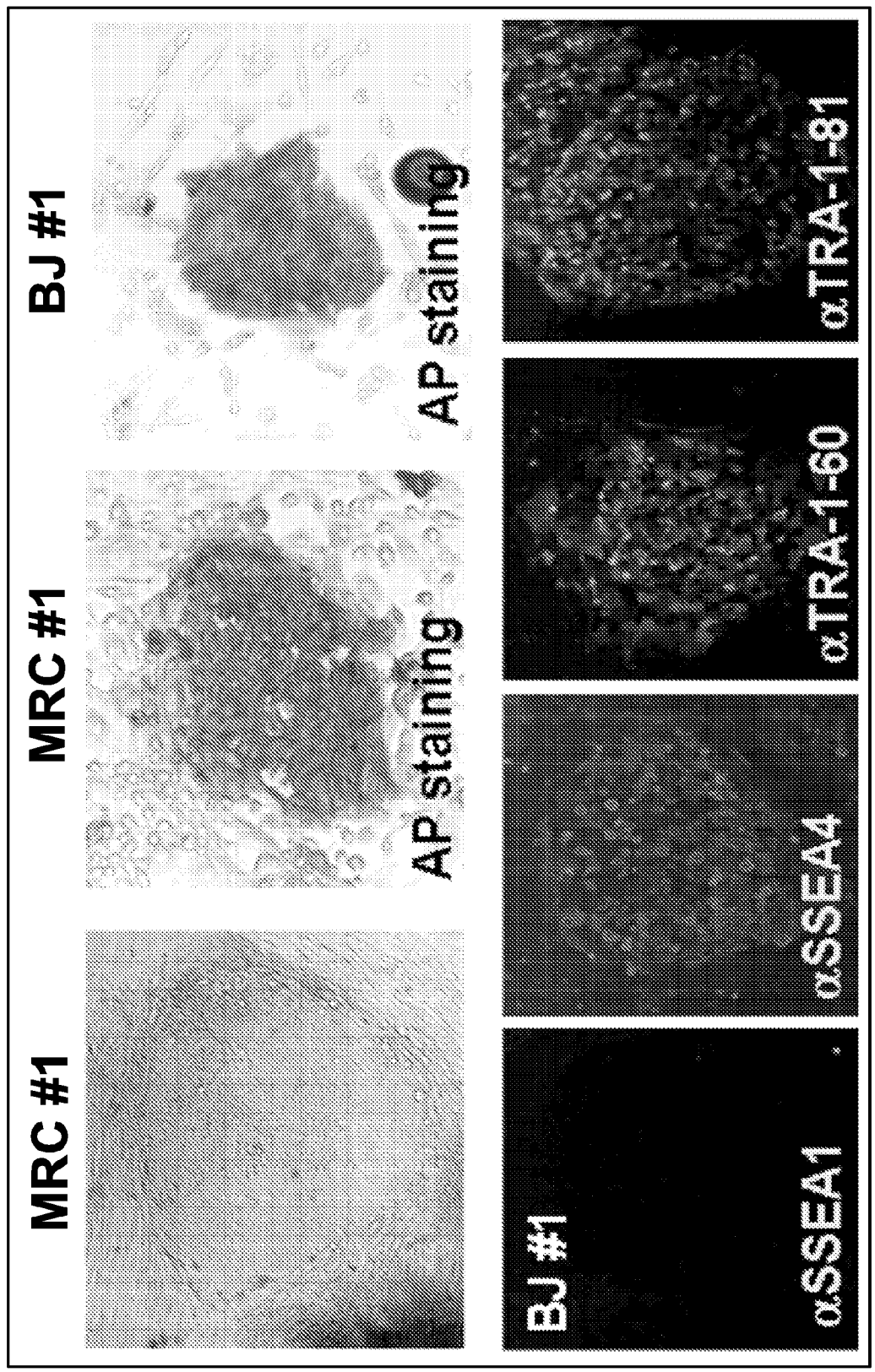
FIG. 13 contains photographs demonstrating the feeder-free generation of human iPS-like cells. iPS-like colonies generated without mouse SNL feeder cells were expanded on mitotically inactivated MRC-5 cells. All the clones tested expressed alkaline phosphatase and human ES/iPS markers, SSEA4, TRA-1-60, and TRA-1-81.

Generating iPS Cells without Using Mouse Feeder Cells and Fetal Calf Serum iPS-like colonies were formed when HCF, BJ, and MRC-5 cells were infected with HIV vectors expressing Oct3/4, Sox2, Klf4, and c-Myc and simply maintained in a serum-free media (HESGro, Millipore, containing b-FGF) for two weeks (FIG. 13, upper left panel). iPS clones were successfully expanded on inactivated human MRC-5 cells. These mouse feeder cell-free human iPS cells expressed human iPS/ES markers including alkaline phosphatase, SSEA4, TRA-1-60, and TRA-1-81 (FIG. 13). When a modified medium (100 mL of HESGro media plus 25 mL of mTeSRtml (Stem Cell Technologies)) was used, human iPS cells could be derived and expanded without using feeder cells and fetal calf serum (not shown). These results demonstrate that iPS cells for clinical applications can be generated without using mouse feeder cells and fetal calf serum.

Example 5

Determining Optimal Intracellular Environment for Efficient Production of iPS Cells Ectopic expression of pluripotent genes can rely on the host environment to achieve reprogramming of a non-stem into a stem cell phenotype. To secure optimal induction of pluripotent reprogramming, the influence of the intracellular background environment on the efficiency of iPS generation can be delineated amongst target somatic cells. iPS cells are derived from various murine and human somatic cell lines originating from different tissues and different age groups, and the most efficient cell source for iPS generation is determine. In order to verify pluripotent outcome, putative iPS cell clones are characterized by the following criteria: (i) degree of expression of pluripotent markers (e.g., human SSEA-4, TRA-1-60 and TRA-1-81; mouse SSEA-1); (ii) extent of telomerase activity (i.e., TRAPEZE telomerase kit); (iii) propensity for in vitro and in vivo three germinal layer formation (e.g., embryoid body generation); (iv) completeness in utero organogenesis (i.e., hybrid iPS/blastomere development for mouse iPS cells); and (v) robustness of tissue-specific differentiation (e.g., cardiomyocytes). Ranking of cytotypes based on the listed criteria is used to determine the optimal intracellular environment for efficient production of iPS cells.

Reprogramming-associated signaling cascades are induced by ectopic gene expression, and ultimately reshape cellular phenotypes through transformation of genome-wide expression profile. Bioinformatics and network biology in combination with microarray, high-throughput transcriptome analysis is used to chart gene networks responsible for maintaining pluripotency in ES cells (Yu et al., Science, 318:1917-20 (2007) and Evans & Kaufman, Nature, 292:154-6 (1981)). This technology has identified critical pathways and patterns of gene expression synchronized to coordinate differentiation (Martin, Proc. Natl. Acad. Sci. USA, 78:7634-8 (1981) and Thomson et al., Science, 282:1145-7 (1998)). The reverse engineering approach to chart re-programming processes in response to transient ectopic pluripotent gene expression should thus provide valuable insight to the signaling pathways required to generate safe iPS cells.

Comparison of benchmarked ES cell transcriptomes with iPS-derived cytotypes is performed in order to reveal the roadmap for effective reprogramming of somatic tissues and advance safe iPS derivation strategies without activation of oncogenic networks that can increase long-term risk of uncontrolled growth.

$5 \times 10^4$ cells derived from skin, bone marrow, heart, lung, kidney, and liver of B16-GFP transgenic mice at different ages (new born, 6 weeks old, and 1 year old) are transduced with HIV vectors expressing Oct3/4, Sox2, Klf4, and c-Myc at multiplicity of infection of 10. Primary human cardiac fibroblasts, hepatocytes, neonate, and adult dermal fibroblasts and mesenchymal stem cells (ScienCell) are also transduced. The transduced cells are cultured in the specific growth media for 4 days, and are spread in a 10-cm plate on SNL feeder cells. The medium is changed to LIF- and FCS-containing media for mouse iPS generation, while serum-free growth media with b-FGF is used for human iPS derivation. One third of the culture supernatants is replaced daily. The cells are monitored for up to 4 weeks, and the number of iPS-like colonies on the plates is counted. The colonies are expanded, and iPS clones are obtained from each group. Their authenticity is verified by surface marker expression. Skin-derived mouse iPS clones from different age groups and iPS clones from different tissues of a 6 week-old mouse (2 clones/group), as well as human iPS clones from different primary tissues are further characterized as shown in Table 2.

TABLE 2

Experiments performed to characterize iPS cells in Aims 1 and 2

| | iPS/ES-specific surface markers | Expression of stem cell genes | Telomerase activity | in vitro differentiation | Teratoma Formation | Chimeric animals | Transcriptomes |
|---|---|---|---|---|---|---|---|
| $1^{st}$ generation | ✓ | ✓ | ✓ | ✓ | ✓ | ✓ | ✓ |
| $2^{nd}$ generation | ✓ | ✓ | ✓ | ✓ | ✓ | ✓ | ✓ |

Clonal expansion of iPS cells can produce a homogenous cell population amendable to transcription profiling using genome-wide analysis. Transcriptome profiling of parental cytotype in comparison to progenitor cells at sequential stages of reprogramming is achieved during iPS cellular induction. Mouse embryonic fibroblasts are profiled according to transcriptome expression and are used as a reference point to compare iPS-like clones identified by characteristic morphology upon ectopic gene expression. To identify subtle expression network changes predictive of safe and effective reprogramming, iPS-like clones with and without transient expression of oncogenes such as c-Myc are compared to traditional ES cell lines through mRNA isolation, microarray data collection, and bioinformatics network analysis.

Genomics. Total RNA is extracted at selected reprogramming stages using a combination of gDNA Eliminator and RNeasy columns (Qiagen). cDNA is prepared from total RNA samples using MMLV Reverse Transcriptase (Invitrogen). Samples are subjected to microarray analysis by labeled cRNA hybridization to the mouse genome 430 2.0

GeneChip (Affymetrix) (Behfar et al., *J. Exp. Med.*, 204: 405-20 (2007); Nelson et al., *Stem Cells*, 26:1464-73 (2008); Perez-Terzic et al., *Nat. Clin. Pract. Cardiovasc. Med.*, 4 Suppl 1, S68-76 (2007); and Chung et al., *Nat. Clin. Pract. Cardiovasc. Med.*, 4 Suppl 1, S60-7 (2007)). Real-time PCR is performed using a standard TagMan® PCR kit protocol on an Applied Biosystems 7900HT Sequence Detection System (Applied Biosystems). Comparisons between groups are performed by Student's t tests with 95% confidence intervals.

Gene Expression Profiling. Gene expression changes of microarray data acquired using the GeneChip Scanner 3000 (Affymetrix, Inc, Santa Clara, Calif.) are profiled with the Genespring GX 7.3 analysis software suite (Agilent Technologies). The derived gene list is limited to report transcripts with expression levels above background and then is subjected to 1-way ANOVA, using a Benjamini-Hochberg post hoc multiple testing correction for all P<0.01. Differentially expressed genes (P<0.05) are excluded from sub-threshold transcripts using Volcano plot analysis, according to a minimum 1.5-fold change, and ontologically dissected to determine physiological system priority emphasized within changing transcripts. Molecular interactions of expression profiles comprising pluripotent gene expression are examined and formatted for Cytoscape 2.2, which provides an ad hoc network map of integrated up- and down-regulated candidate genes driving the pluripotent switch.

Example 6

Establishing Genomic Modification-Free Technology for Safe Production of iPS Cells Retroviral or lentiviral vector integration has risks associated with insertional mutagenesis. Use of oncogenic c-Myc during reprogramming is also problematic for clinical application of the resulting iPS cells, as sustained c-Myc expression can increase the risk of tumor formation in iPS-derived cells in vivo. In order to avoid these risks, iPS cells can be generated without integrating vectors and continuous c-Myc expression. Derivation of iPS cells with transient expression from non-integrating vectors can solve both problems, as the resulting iPS cells carry no genomic modifications.

Since retroviral promoters are rapidly silenced in mouse or human ES cells (Wolf & Goff, *Cell*, 131:46-57 (2007)), expression of stem cell factors from the introduced retroviral vectors was also silenced in iPS cells (Takahashi et al., *Cell*, 131:861-72 (2007)). This observation indicates that the stem cell factors are only required to initiate the reprogramming step, but are not mandatory to maintain the resulting iPS phenotype.

Figure 14:
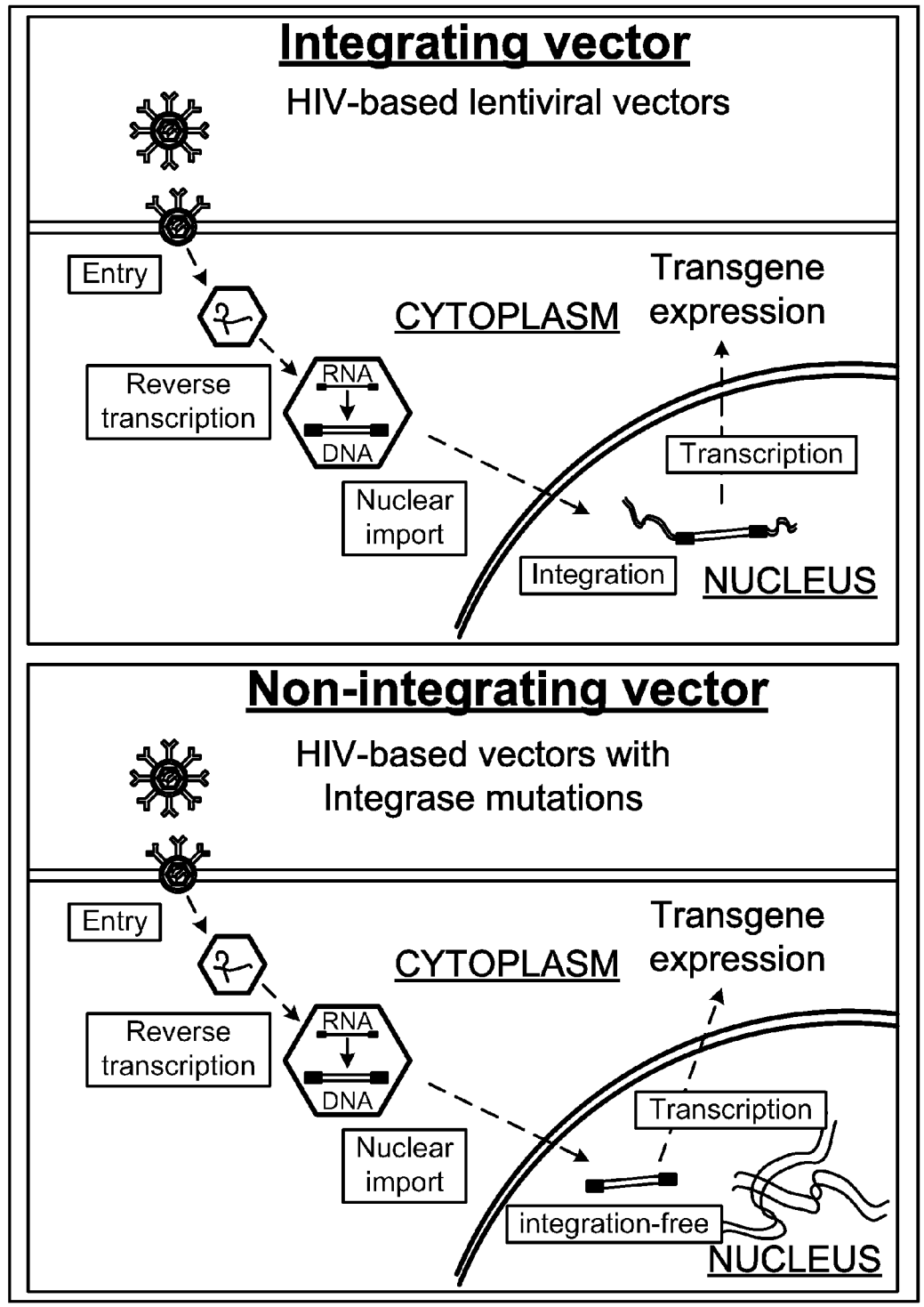
FIG. 14. Integration-free transgene expression. HIV-based vectors with mutations in the viral Integrase do not integrate into host genome and express transgene products without integration. AAV-based vectors also express transgene products without integrating into host genome.
Figure 15:
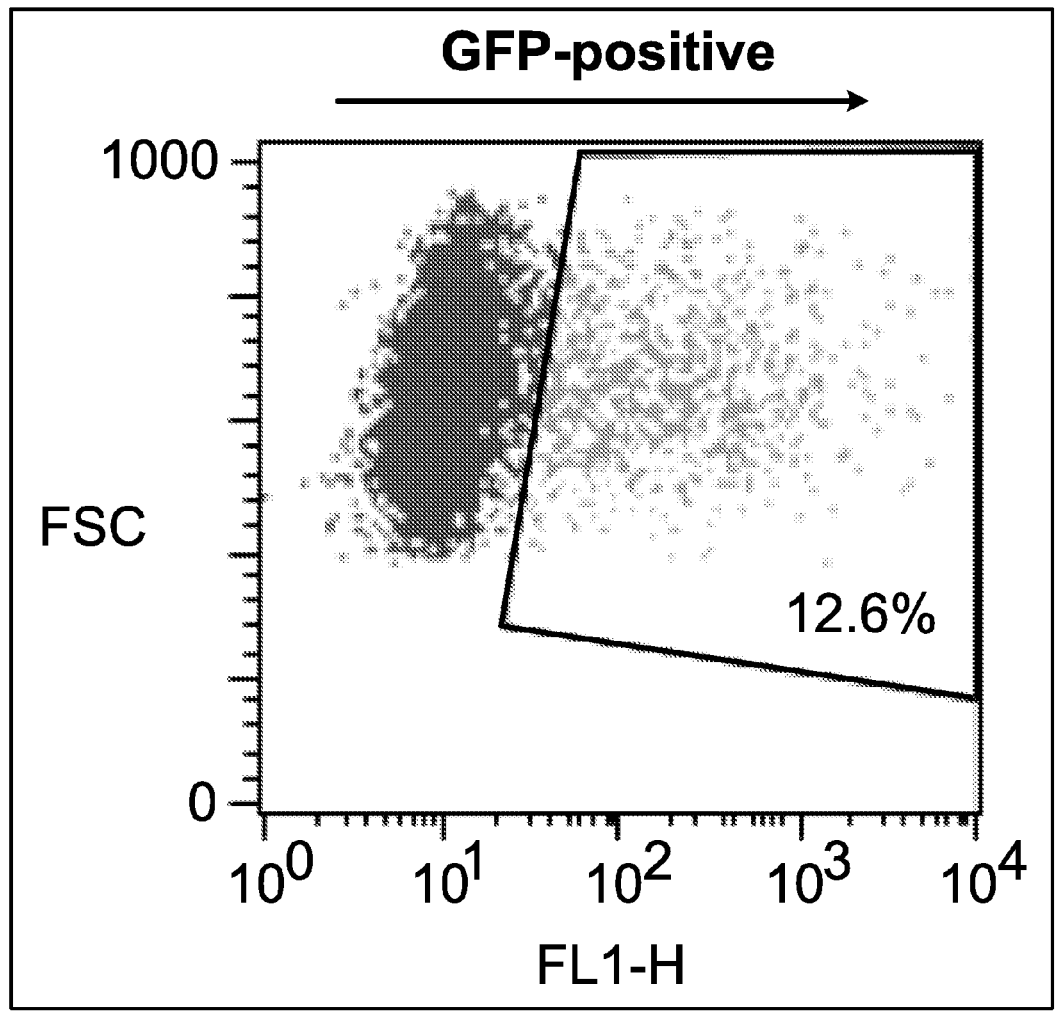
FIG. 15. Expression of GFP in human cells transduced with an AAV serotype 9 vector. $2\times10^5$ cells were infected with 1 μL of a concentrated GFP-expressing AAV9 vector. GFP-positive cells were analyzed by FACS at 2 days after infection.

It is hypothesized that initiation of the reprogramming step by non-integrating vectors is sufficient to generate iPS cells. To test this hypothesis, and improve upon the iPS derivation strategy, a genomic modification-free strategy for iPS generation is developed. As non-integrating vectors, AAV and integrase-negative HIV vectors are used (FIGS. 14 and 15). AAV-based vectors are particularly attractive for future clinical applications, as AAV-based vectors can be used under biosafety level 1 practice.

HIV-based vectors generally integrating into host genome before they express significant levels of transgene products. However, recent studies have shown that HIV-based vectors generated with a packaging construct with non-functional viral integrase can express transgene for long term without integrating into host genome (Negri et al., *Mol. Ther.*, 15:1716-23 (2007); Apolonia et al., *Mol. Ther.*, 15:1947-54 (2007); and Saenz et al., *J. Virol.*, 78:2906-20 (2004)). Similarly, although wildtype AAV can site-specifically integrate into AAVS1 site at chromosome 19 (Philpott et al., *J. Virol.*, 76:5411-21 (2002) and Philpott et al., *Proc. Natl. Acad. Sci. USA*, 99:12381-5 (2002)), this AAV integration step is mediated by ectopic AAV viral enzyme Rep and a viral cis sequence in the p5-rep region. Since AAV-based vectors do not carry viral Rep protein nor the p5-rep sequence, they do not integrate into host genome (Flotte et al., *Proc. Natl. Acad. Sci. USA*, 90:10613-7 (1993) and Kaplitt et al., *Nat. Genet.*, 8:148-54 (1994)). Infection of AAV and integrase-negative HIV vectors can lead to transient transgene expression without vector integration into host genome. Such non-integrating vectors are used to express the stem cell-related genes and establish genomic modification-free iPS cells.

An additional risk with iPS preparation is the current use of animal-derived biological reagents that preclude clinical grade production and utilization in practice. iPS colonies are established in the absence of fetal calf serum and mouse feeder cells. After successful reprogramming of human somatic cells by non-integrating vectors, genetic modification-free iPS cells are established without using FCS and mouse feeder cells.

Non-integrating HIV vectors expressing human stem cell-related factors are generated using a packaging construct with mutations in the viral integrase (Saenz et al., *J. Virol.*, 78:2906-20 (2004)). The vectors are concentrated about 100-fold by ultracentrifugation as described elsewhere (Strang et al., *Gene Ther.*, 11:591-8 (2004) and Strang et al., *J. Virol.*, 79:1765-71 (2005)). AAV serotypes 2 and 9 vectors expressing the four human factors Oct3/4, Sox2, Klf4 and c-Myc are generate. AAV vectors are concentrated and are purified through ultracentrifugation through cesium chloride gradients. Transgene expression in the cells infected by 10 μL of the concentrated non-integrating HIV and AAV vectors is verified. $5 \times 10^4$ human skin-derived and cardiac fibroblast cells and mouse tail-derived fibroblasts are consecutively infected with 200 μL of concentrated vectors for 3-14 days. The transduced cells are cultured in the specific growth media for the first 4 days, and are spread in a 10-cm plate with inactivated SNL feeder cells. The medium is changed to LIF- and FCS-containing mouse ES media for mouse iPS generation, while serum-free growth media with 40 ng/mL of b-FGF is used for human iPS derivation. One third of the culture supernatants is replaced daily. The cells are monitored for up to 4 weeks, and the number of iPS-like colonies on the plates is counted. Obtained iPS-like colonies are isolated to confirm absence of vector integration by sensitive Q-PCR and FISH methods. Representative iPS clones are characterize for their pluripotency as described herein, and the transcriptomes between the iPS made with or without integrating vectors are compared. In order to demonstrate increased safety, iPS-derived chimeric mice are generated using mouse iPS cells made with or without integrating vectors (two clones each), and their respective long-term risk of tumorigenicity is compared.

Mitotically inactivated MRC-5, HCF, and BJ cells are tested to determine whether they can support prolonged undifferentiated growth of human iPS cells. It is determined whether iPS cells can be generated by using autologous human cells as feeders. Genomic modification-free iPS cells are generated by using autologous human cells as feeders.

Primary mouse cells. B16-GFP transgenic mice were obtained from Dr. Richard A. Vile (Mayo Clinic). Bone marrow, skin, heart, lung, stomach, spleen, kidney, liver, and tail is harvested, and tissue-derived primary cell cultures are established as described elsewhere (Noser et al., *J. Virol.*, 80:7769-74 (2006); Strang et al., *J. Virol.*, 79:1765-71 (2005); and Relander et al., *Mol. Ther.*, 11:452-9 (2005)). Cells are transduced by HIV vectors, and iPS generation efficiency is monitored.

Mouse ES and iPS culture. Mouse ES and iPS cells are maintained in Glasgow's Minimum Essential Medium (Bio-Whittaker-Cambrex) supplemented with pyruvate and L-glutamine (Cellgro), non-essential amino acids (Cellgro), β-mercaptoethanol (Sigma-Aldrich), 10% fetal calf serum (FCS) (Invitrogen), and leukemia inhibitory factor (Chemicon International).

Primary human cells. Primary cardiac fibroblasts, pulmonary fibroblasts, hepatocytes, neonate and adult dermal fibroblasts, and mesenchymal stem cells (ScienCell) are cultured in specific media (ScienCell) and are used for iPS induction.

Human iPS culture. Human iPS cells are maintained in serum-free HuESGro medium
(Millipore) supplemented with basic fibroblast growth factor (40 ng/mL).

ER formation. Mouse iPS cells are differentiated into three-layer embryoid bodies using the hanging-drop method in differentiation media supplemented with 20% FCS and TNF-α (Invitrogen) as described herein. In vitro differentiation of mouse iPS cells into embryoid bodies capable of rhythmic contractions are performed as described herein.

Cell lines. 293T (ATCC), MRC-5 (ATCC), BJ (ATCC), and SNL feeder cells (MMRRC) are maintained in Dulbecco's modified Eagle medium (DMEM) supplemented with 10% FCS and antibiotics.

HIV-based vectors. HIV-based integrating vectors are prepared by transfection of 293T cells by using Fugene-6 (Roche) as described elsewhere (Ikeda et al., *Gene Ther.*, 9:932-8 (2002); Ikeda et al., *Nat. Biotechnol.*, 21:569-72 (2003); Strang et al., *Gene Ther.*, 11:591-8 (2004); and Sakuma et al., *Gene Ther.*, 14:185-9 (2007)). For efficient transduction of mouse cells, pEx-QV packaging construct is used (Ikeda et al., *J. Virol.*, 78:11816-22 (2004)). The non-integrating HIV-packaging construct, which carries a mutation in the viral integrase, is used to generate non-integrating HIV vectors expressing defined human factors.

AAV vector. Helper-free AAV vectors based on AAV serotypes 2 and 9 are generated by transient transfection of 293T cells with pHelper, pRepCap, or pRep2Cap9 and pAAV-MCV-derived vector constructs (Stratagene).

Immunoblotting. Immunoblotting is performed to detect Oct3/4, Sox2, Klf4, c-Myc, Nanog, and Lin28 as described herein.

Immunostaining. Immunostaining is performed to detect cell surface markers as described herein.

Genomics. Total RNA is extracted at selected reprogramming stages using a combination of gDNA Eliminator and RNeasy columns (Qiagen). cDNA is prepared from total RNA samples using MMLV Reverse Transcriptase (Invitrogen). Samples are subjected to microarray analysis by labeled cRNA hybridization to the mouse genome 430 2.0 GeneChip (Affymetrix) (Behfar et al., *J. Exp. Med.*, 204: 405-20 (2007); Nelson et al., *Stem Cells*, 26:1464-73 (2008); Perez-Terzic et al., *Nat. Clin. Pract. Cardiovasc. Med.*, 4 Suppl 1, S68-76 (2007); and Chung et al., *Nat. Clin. Pract. Cardiovasc. Med.* 4 Suppl 1, S60-7 (2007)). Real-time PCR is performed using a standard TaqMan® PCR kit protocol on an Applied Biosystems 7900HT Sequence Detection System (Applied Biosystems). Comparisons between groups are performed by Student's t tests with 95% confidence intervals.

Gene Expression Profiling. Gene expression changes of microarray data acquired using the GeneChip Scanner 3000 (Affymetrix, Inc, Santa Clara, Calif.) are profiled with the Genespring GX 7.3 analysis software suite (Agilent Technologies). The derived gene list is limited to report transcripts with expression levels above background and then is subjected to 1-way ANOVA, using a Benjamini-Hochberg post hoc multiple testing correction for all $P<0.01$. Differentially expressed genes ($P<0.05$) are excluded from sub-threshold transcripts using Volcano plot analysis, according to a minimum 1.5-fold change, and ontologically dissected to determine physiological system priority emphasized within changing transcripts. Molecular interactions of expression profiles comprising pluripotent gene expression are examined and formatted for Cytoscape 2.2, which provides an ad hoc network map of integrated up- and down-regulated candidate genes driving the pluripotent switch.

Figure 16:
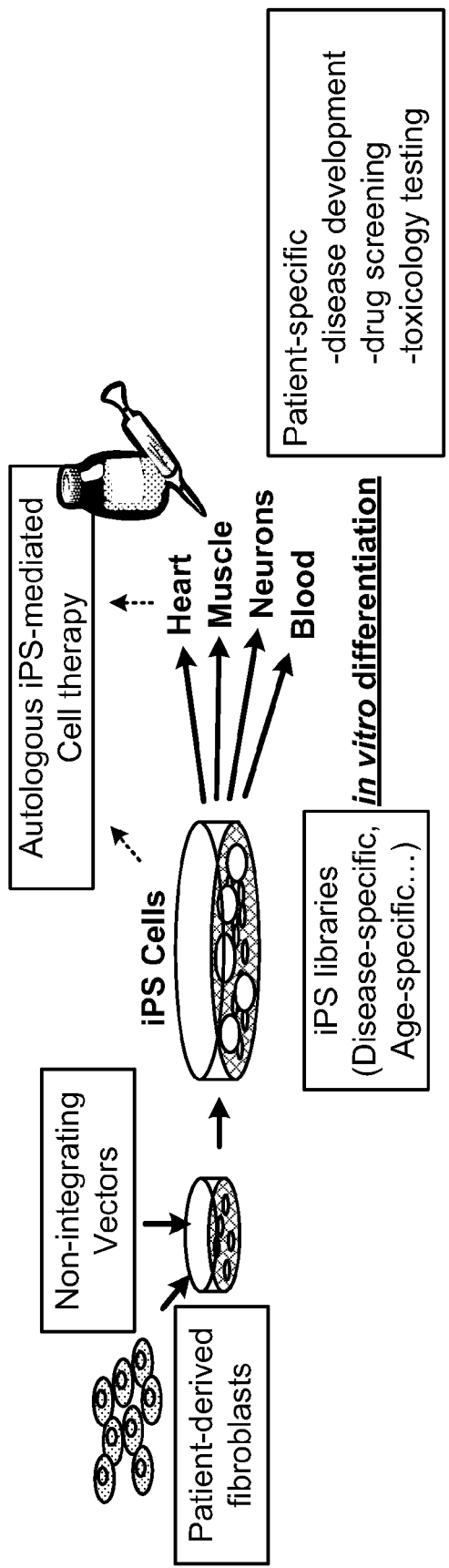
FIG. 16 is a schematic of uses of iPS cells provided herein.

Achieving efficient and safe iPS derivation provides an essential platform for realizing individualized cell therapy. For clinical iPS application, a further understanding of the influence of intracellular environment on the reprogramming efficiency is helpful. The studies provided herein can be extended into broad ranges of human populations including young and old, healthy and diseased donors. Reprogramming efficiency can be lower from older and diseased donors. If this is the case, further optimization of the gene transfer vectors, combination of defined stem cell factors, and vector transduction conditions can be used to improve the reprogramming efficiency particularly from old and diseased subjects. Through this approach, disease-specific iPS libraries can be generated. Such patient-specific iPS libraries can provide a valuable platform to study patient-specific disease development mechanisms in vitro. They can also increase the efficiency of patient-specific drug discovery. Thus, the methods and materials provided herein can be used for autologous iPS-mediated cell therapies as well as for tools to assess patient-specific disease development, drug screening, and drug toxicity (FIG. 16).

Example 7

Repair of Acute Myocardial Infarction with iPS Induced by Human Stemness Factors Transduction pSIN-CSGWdlNotI-derived transfer vectors were generated with human OCT3/4, SOX2, KLF4 and c-MYC cDNAs (Open Biosystems; Nelson et al. *Clin. Translation Sci.*, 2:118-126 (2009)). The packaging plasmid, pCMVR8.91, was engineered with H87Q mutation in the HIV-1 capsid region for increased transduction efficiency of purified infectious supernatants (Nelson et al. *Clin. Translation Sci.*, 2:118-126 (2009)). Mouse embryonic fibroblasts, obtained from embryos at 14.5 days post-coitum (dpc), were expanded in maintenance medium containing Dulbecco's modified Eagle's medium (Invitrogen) supplemented with 10% fetal calf serum (FCS), 1% L-glutamine (Invitrogen) and 1% penicillin/streptomycin, and plated at $10^5$/24-wells prior to transduction for 12 hours with infectious supernatants. Transduced fibroblasts were replated at confluence, and iPS isolated in 2 weeks for clonal expansion. Cells were labeled with HIV vectors carrying LacZ (pLenti6/UbC/V5-GW/LacZ, Invitrogen) or luciferase (pSIN-Luc) (Hasegawa et al., *Clin. Cancer Res.*, 15:6170-6178 (2006)).

Pluripotent Induction

R1-derived embryonic stem cells and iPS were expanded in embryonic stem cell media. Cells were fixed with 3% paraformaldehyde, permeabilized, and stained with anti-SSEA-1 antibody (MAB4301; dilution 1:50; Chemicon) along with secondary goat anti-mouse Alexa Fluor 568 (1:250; Invitrogen). Nuclei were labeled with 4,6'-diamidino-2-phenylindole (DAPI; Invitrogen). For ultrastructural evaluation, cells were examined on Hitachi 4700 field emission scanning or JEOL 1200 EXII transmission electron microscopes (Perez-Terzic et al., *Nat. Clin. Pract. Cardiovasc. Med.*, 4(Suppl. 1):568-576 (2007)). Growth and differentiation potential were determined upon subcutaneous injection in anesthetized (2-3% isoflurane) athymic nude mice. Cryopreserved tissue was processed for hematoxylin/eosin procedures (Yamada et al., *Stem Cells*, 26:2644-2653 (2008) and Behfar et al., *J. Exp. Med.*, 204:405-420 (2007)).

Differentiation iPS were differentiated into embryoid bodies using the hanging-drop method (Behfar et al., *FASEB J.*, 16:1558-1566 (2002)). Expression of pre-cardiac mesoderm and cardiac differentiation markers was detected by RT-PCR. Total RNA was extracted with a combination of gDNA Eliminator and RNeasy columns (Qiagen). cDNA was prepared from RNA samples using Superscript III First Strand Synthesis System (Invitrogen). Mouse GAPDH (4352932E; Applied Biosystems) was used as control. Analyzed genes included Gata4 (Mm00484689_m1), Myocd (Mm00455051_m1), and Mef2c (Mm01340839_m1; Applied Biosystems).

Diploid Aggregation

Contribution to embryonic development was assessed through diploid aggregation (Nelson et al., *Phil. Trans. R. Soc. B.*, 364:269-276 (2009)). Host embryos from CD-1 superovulated females were collected at 2.5 dpc. Fibroblasts or iPS were partially digested using trypsin 0.25%-EDTA (Invitrogen), and 8-15 cell clumps were placed with paired embryos denuded of zona pellucida. The aggregation complex was incubated for 24 hours (in 5% $CO_2$/5% $O_2$/90% $N_2$) until blastocyst cavitation (Nelson et al., *Phil. Trans. R. Soc. B.*, 364:269-276 (2009)). Chimeric embryos were transplanted into anesthetized (2-3% isoflurane) pseudopregnant surrogate CD-1 mothers, harvested at 9.5 dpc, and analyzed for distribution of LacZ-labeled progenitors (Nelson et al., *Phil. Trans. R. Soc. B.*, 364:269-276 (2009)).

iPS Therapy

Male, 8-12 weeks old C57BL/6 or athymic nude mice were anesthetized (1.5-2% isoflurane), intubated (Mini Vent 845, Hugo Sacks Electronik), and left coronary artery ligated with a 9-0 suture under direct visualization following minimally invasive thoracotomy. Myocardial ischemia was confirmed by electrocardiography, echocardiography, and color change of left ventricular wall. Fibroblasts or iPS (200,000/10 µL of differentiation medium) were transplanted with four injections of 2.5 µL within 30 minutes after ligation. Cryosections (7 µm-thickness) were processed for hematoxylin/eosin, Masson's trichrome, luciferase and O-gal staining (Yamada et al., *Stem Cells*, 26:2644-2653 (2008) and Behfar et al., *J. Exp. Med.*, 204:405-420 (2007)). Sections were labeled with luciferase (1:5000, Sigma) or β-galactosidase antibody (1:5000, Abcam) coupled with Alexa-568 secondary antibody (1:1000, Invitrogen) and co-localized with α-actinin (1:200, Sigma), smooth muscle actin (1:200, Abcam), CD31 (1:200, Abcam), or SSEA-1 (1:50, Chemicon) antibodies all paired with Alexa-488 antibody (1:1000, Invitrogen).

Live Cell Imaging and Heart Performance

Luciferase-transfected fibroblasts or iPS were cultured for multiple passages including a freeze/thaw cycle prior to expansion and transplantation. Cells were tracked with the IVIS 200 Bioluminescence Imaging System (Xenogen) following intra-peritoneal injection of 150 mg/kg D-luciferin (Xenogen), and signals analyzed with the Living Image Software (Xenogen). Ventricular performance was quantified by echocardiography (RMV-707B scanhead, Vevo770, Visual Sonics). Ejection fraction (%) was calculated as $[(LVVd-LVVs)/LVVd]\times100$, where LVVd is left ventricular end-diastolic volume (µL) and LVVs, left ventricular end-systolic volume (µL). Left ventricular fractional shortening (% FS) was calculated as $[(LVDd-LVDs)/LVDd]\times100$, where LVDd is left ventricular end-diastolic dimension (mm) and LVDs, left ventricular end-systolic dimension (mm) (Yamada et al., *Stem Cells*, 26:2644-2653 (2008)). Electrical activity was monitored by electrocardiography (MP150, Biopac). Data was collected and analyzed by blinded investigators.

Statistical Analysis

Results are presented as mean±SEM. Median is additionally reported when grouped data were compared with non-parametric Mann-Whitney U test. Comparison between groups over time was performed by two-way repeated-measures ANOVA. Kaplan-Meier analysis was applied with log-rank testing. $p<0.05$ was predetermined as significant, and all values>0.001 were reported.

Results

Nuclear Reprogramming Resets Primitive Morphology and Unlocks Functional Pluripotency.

Figure 17A:
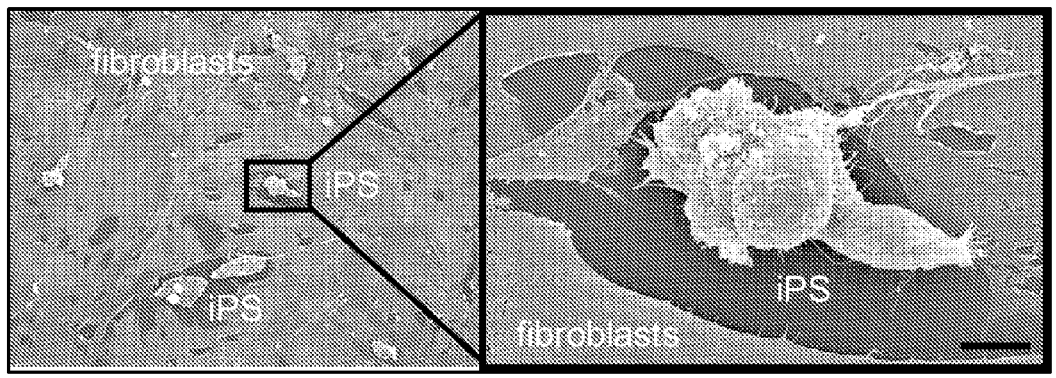
FIG. 17. Induced pluripotent stem cells (iPS) demonstrate pluripotent features. A, Flat fibroblasts reprogrammed with human stemness factors metamorphosed into rounded clusters shown by field-emission scanning electron microscopy. Bar=50 μm. B, In transmission electron microscopy, derived iPS demonstrated nuclear/cytoplasmic composition similar to embryonic stem cells (ES). C, Counterstained by nuclear DAPI, iPS expressed the pluripotent marker SSEA-1, absent from fibroblasts (0 h; left). Bar=5 μm. D, Fibroblasts or iPS clumps were placed along with two 8-cell host embryos for diploid aggregation (1 hour; top). Bar=30 μm. Within 24 hours, iPS spontaneously integrated to form an early stage chimeric blastocyst (24 hours; bottom right), in contrast to fibroblasts that were excluded (24 hours; bottom left).
Figure 17B:
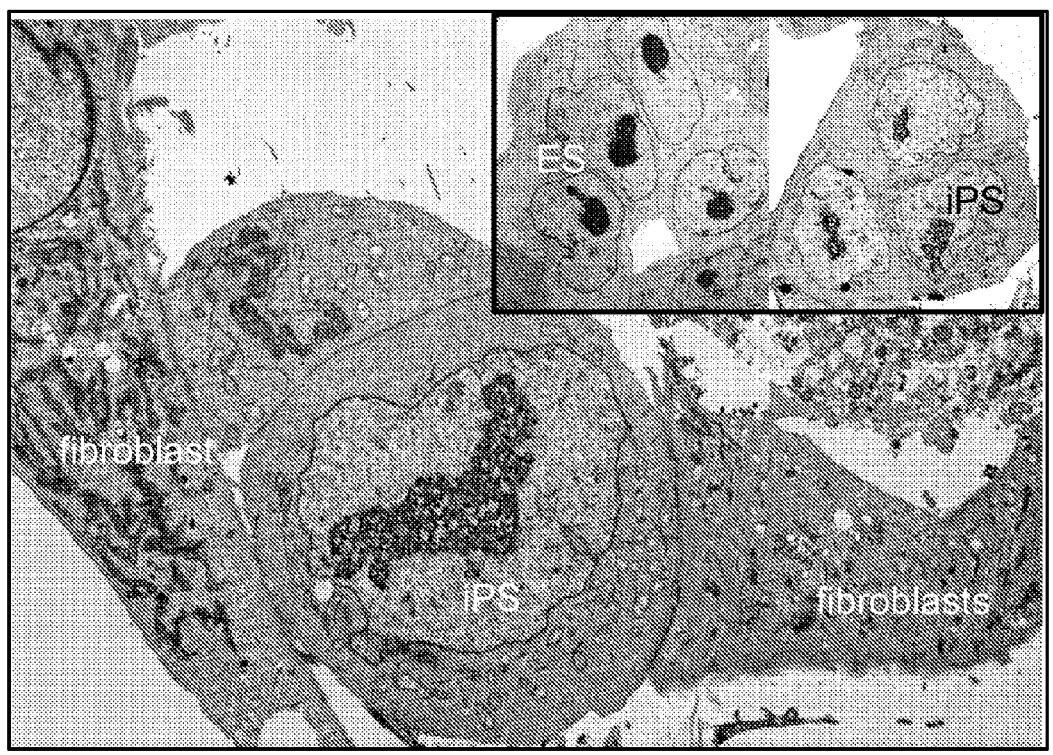
Figure 17C:
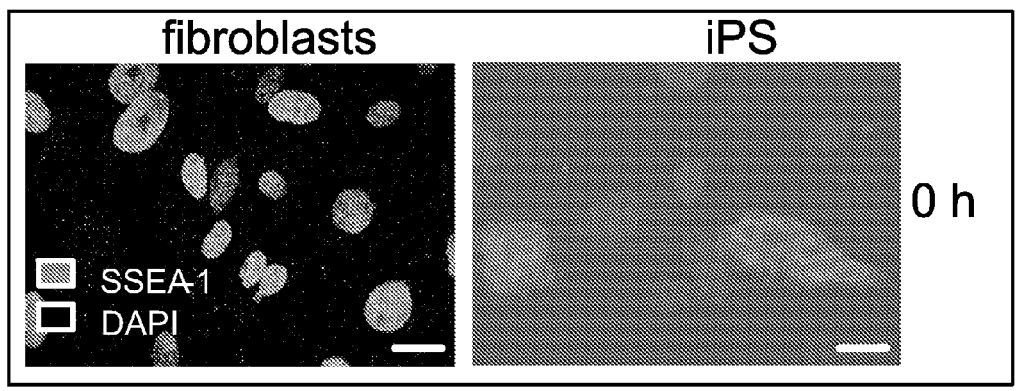
Figure 17D:
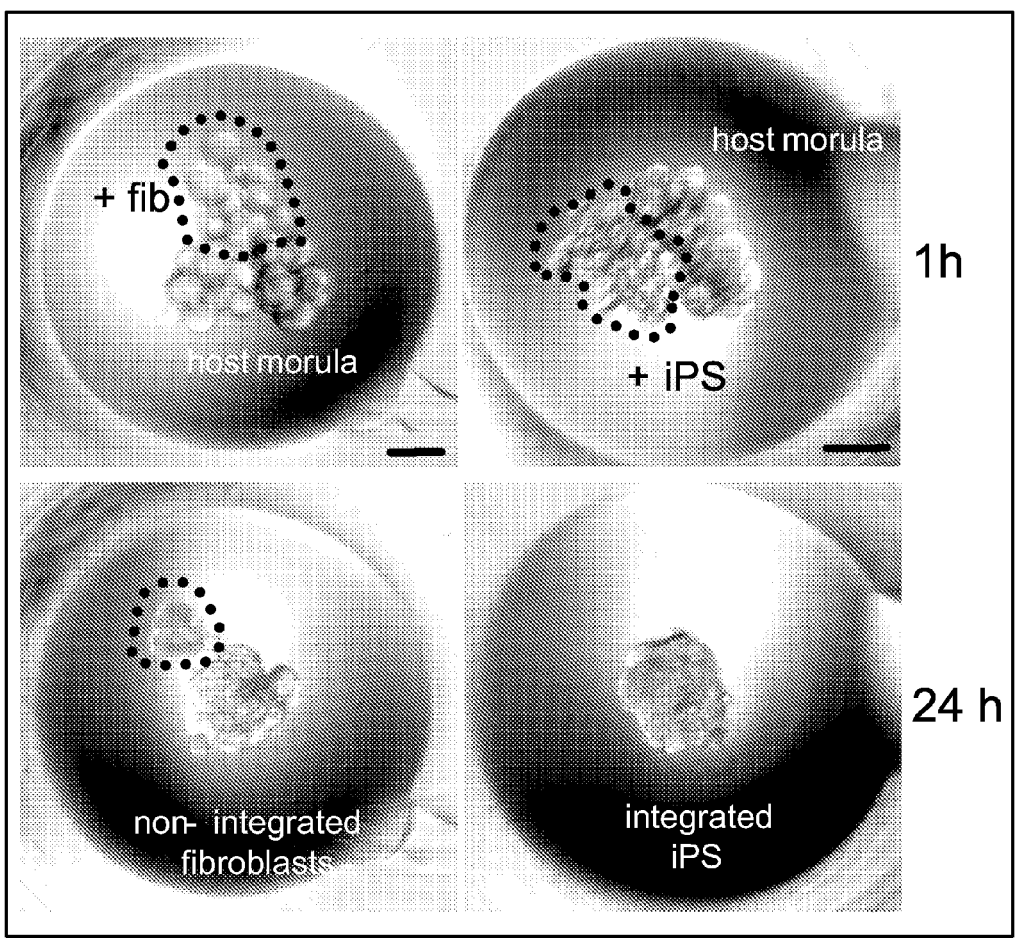

Transduced with human sternness factors, OCT3/4, KLF4, SOX2 and c-MYC, reprogrammed fibroblasts were isolated according to compact clusters of embryonic stem cell-like morphology distinct from monomorphic, single-cell layers of parental fibroblasts (FIG. 17A). Reprogrammed cells displayed distinct sub-cellular architecture, reorganized from original fibroblasts to recapitulate salient features of undifferentiated embryonic stem cells with high nucleo/cytoplasmic ratio, predominance of nuclear euchromatin, and scant density of cytosolic organelles (FIG. 17B). Reprogramming induced expression of the early embryonic SSEA-1 antigen, an initial marker of sternness absent in parental fibroblasts (FIG. 17C). To determine functional pluripotency, the inherent capacity for embryonic integration was probed by diploid aggregation using a pair of denuded host embryos (FIG. 17D, upper). While morula-derived blastomeres incorporated into an embryonic structure after 24 hours in micro-wells, fibroblasts aborted engraftment and failed to contribute to ex utero blastocyst development (FIG. 17D, lower left). In contrast, reprogrammed fibroblasts demonstrated spontaneous integration and contributed to pre-implantation blastocyst formation (FIG. 17D, lower right). Non-coerced assimilation into early stage embryos thereby established bona fide iPS clones, providing a high-stringency quality control measure for functional pluripotency.

Chimeric Embryos Authenticate iPS-Derived Patterning of Normal Cardiogenesis.

Figure 18A:
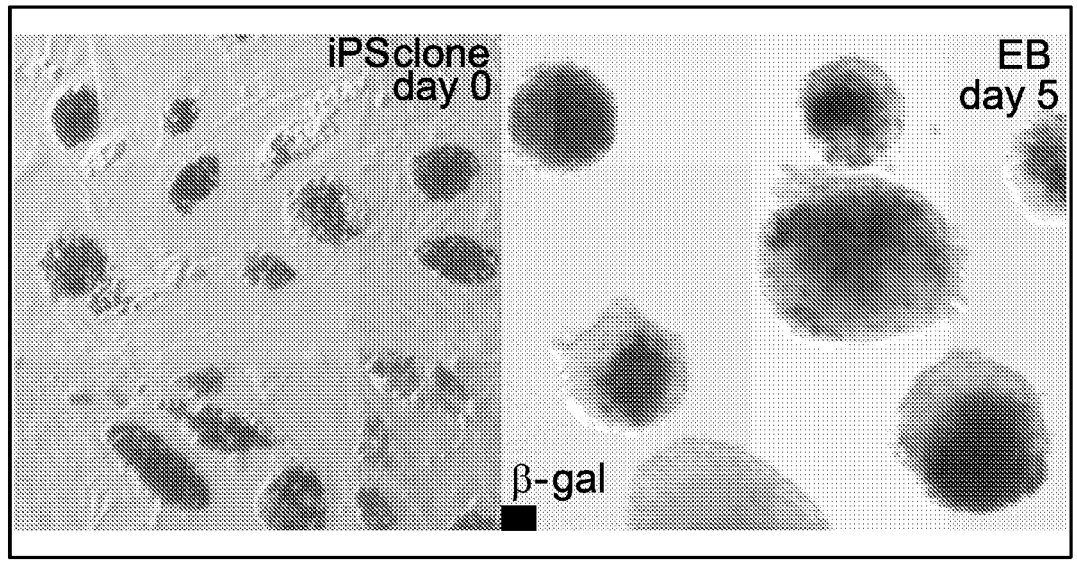
FIG. 18. iPS recapitulate in utero cardiogenic propensity. A, LacZ-labeled iPS clones, detected by β-galactosidase (β-gal) staining, were maintained as undifferentiated colonies at day 0 before aggregation into embryoid bodies (EB). B, Gene expression profiles at day 0 (d0) compared to day 12 (d12) of differentiation demonstrated induction of cardiac transcription factors, Mef2c (p=0.049; n=3), Gata4 (p=0.049; n=3), and Myocardin (p=0.049; n=3). C, Embryos provide a wildtype (WT) environment to determine tissue-specific differentiation (upper left). Derived by diploid aggregations, ES stochastically contribute to tissue patterning with diffuse integration tracked with constitutively labelled EF-lacZ cell line (upper right) and cardiac-specific integration identified by α-MHC-lacZ reporter (lower left). iPS, labeled with ubiquitously expressing reporter with CMV promoter, identifies progeny throughout developing embryo (lower right). D, Chimerism with lacZ-labeled iPS demonstrated robust contribution to developing hearts within 9.5 dpc embryos. Bar=100 µm. E, Heart parenchyma of 9.5 dpc chimeric embryo contained integrated iPS progeny expressing 13-galactosidase. Bar=50 µm.
Figure 18B:
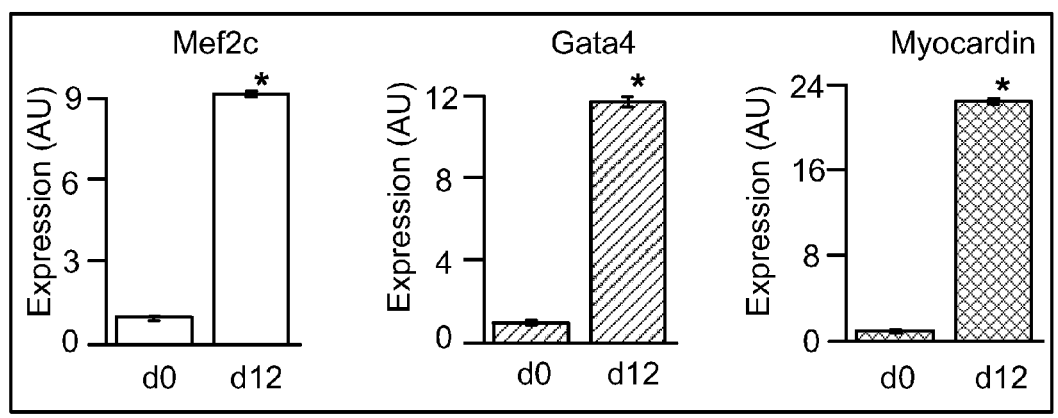
Figure 18C:
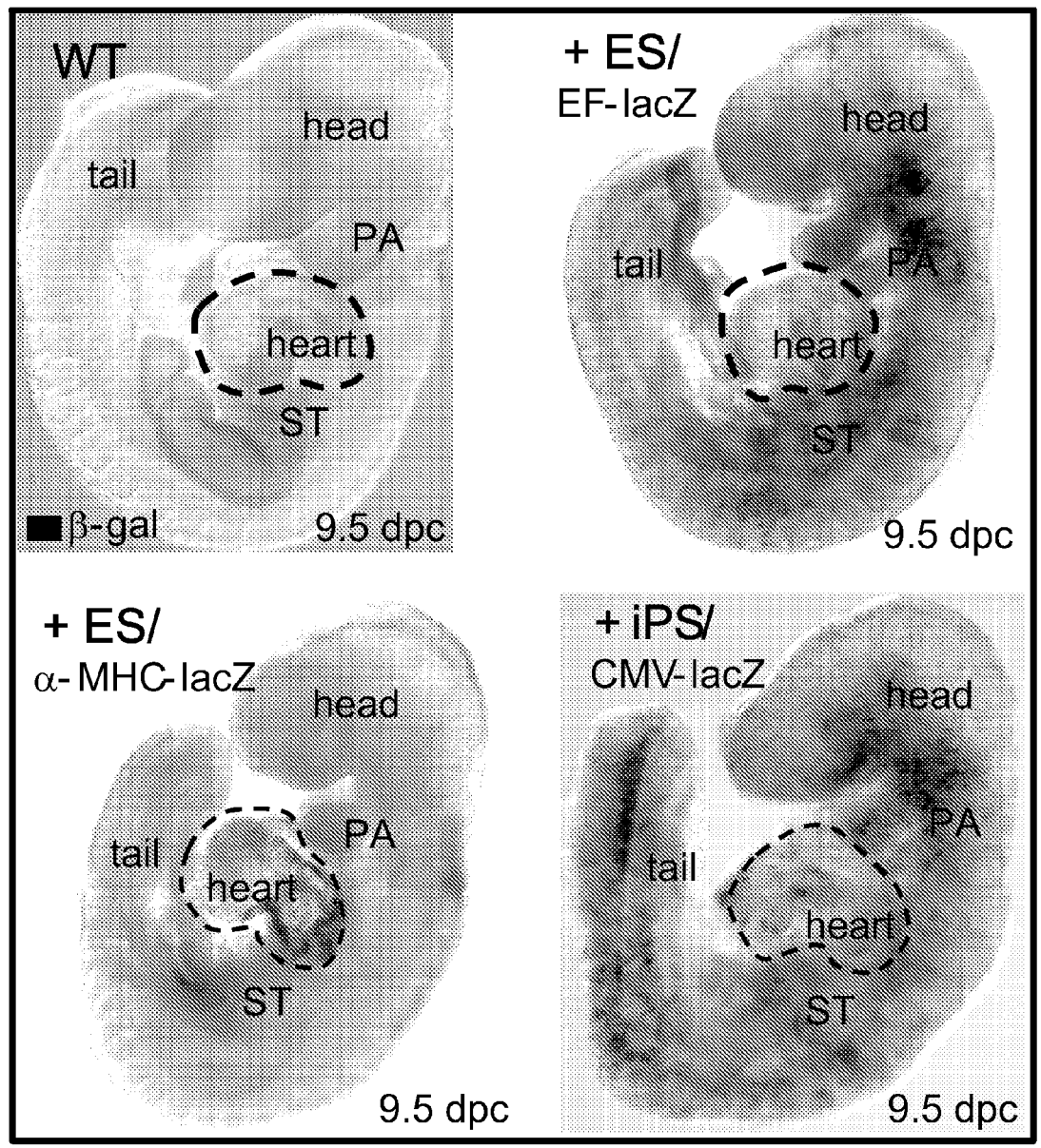
Figure 18E:
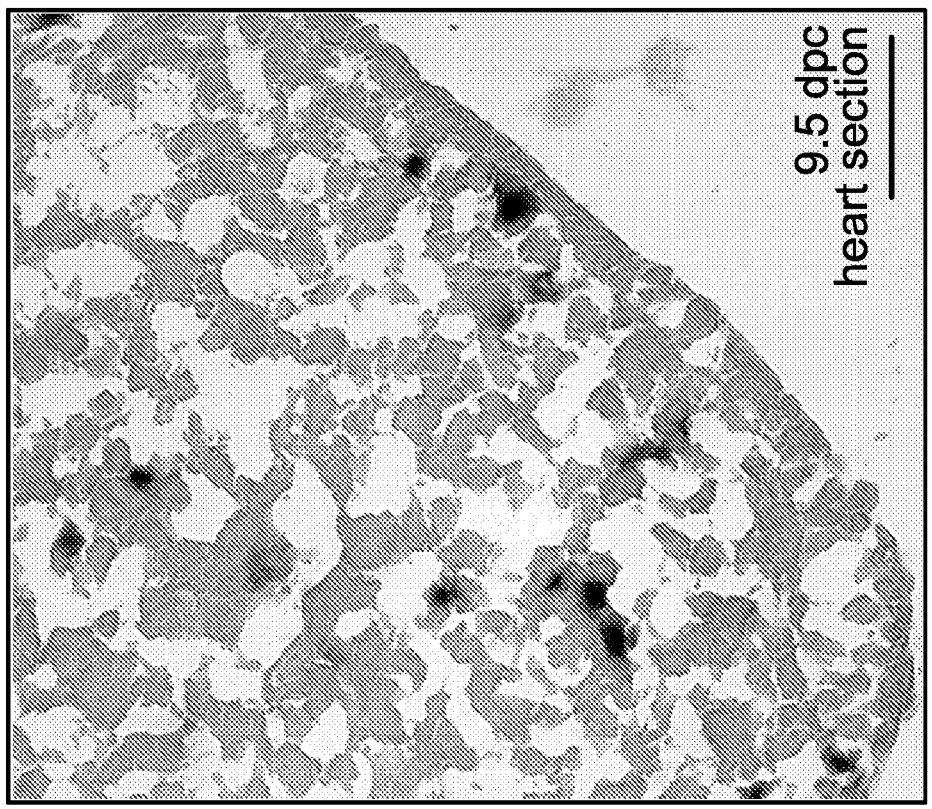
Figure 18D:
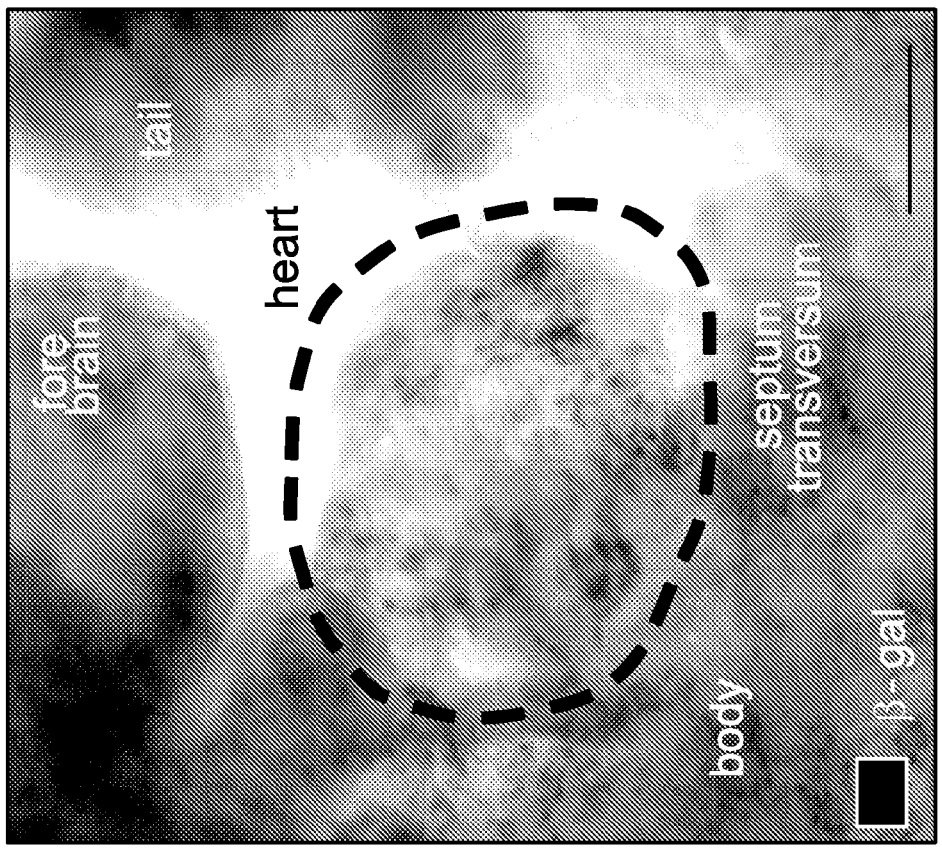

As iPS differentiated within 5-day-old embryoid bodies (FIG. 18A), up-regulation of pre-cardiac markers Mesp1, Tbx5, Cxcr4, and Flk-1 indicated engagement beyond the original fibroblast lineage (Nelson et al., *Stem Cells*, 26:1464-1474 (2008) and Nelson et al., *Differentiation*, 77:248-255 (2009)). Within 12 days, increased expression of canonical cardiac transcription factors, Mef2c (p=0.049; n=3), Gata4 (p=0.049; n=3) and Myocardin (p=0.049; n=3), indicated the capacity for cardiac tissue maturation (FIG. 18B). Beyond redirection of somatic cell fate in vitro, chimeric embryos were utilized to examine the ability of iPS clones to ensure tissue formation during embryonic development in utero. Pre-implantation blastocysts containing lacZ-labeled iPS progenitors were transferred into surrogate uterus, and tracked at early stages of organogenesis. iPS labeled with a constitutively active reporter construct mimicked the stochastic distribution of embryonic stem cells throughout the developing embryo at 9.5 dpc (FIG. 18C). Labeled iPS progeny demonstrated robust contribution to the heart field, including cardiac inflow and outflow tracts as well as left and right ventricles of the embryonic heart parenchyma (FIGS. 18D and 18E). Thereby, qualified iPS clones demonstrated de novo organogenesis and patterning of cardiogenic tissue within a developing embryo.

iPS Engraft into Infarcted Immunocompetent Adult Hearts.

Figures 19A, 19B:
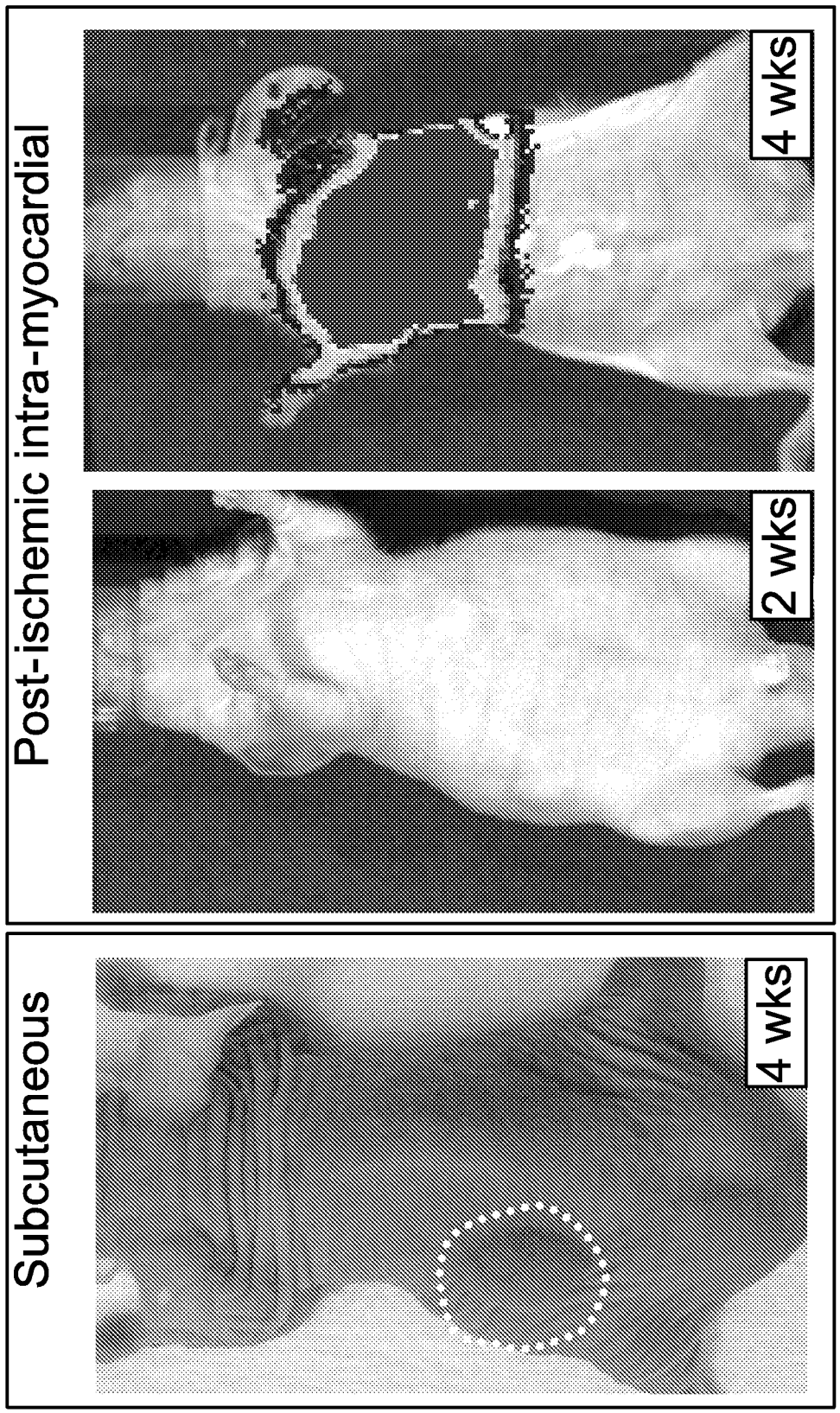
FIG. 19. iPS fate determined by host competency. A, Subcutaneous injection of 500,000 iPS in immunodeficient host resulted in tumor growth (dotted circle). B, Upon acute myocardial infarction, 200,000 iPS transplanted intra-myocardially were detected in the heart region by in vivo bioluminescence imaging dramatically expanding by 4 weeks (wks). C, Tumor growth was detected by echocardiography (upper left) and confirmed on necropsy in all immunodeficient hosts (upper right). Histology demonstrated tumor expansion outside of the heart (lower left), and infiltration within the wall of infarcted myocardium (lower right). D, Immunocompetent hosts reproducibly averted tumor growth upon subcutaneous injection (square) of 500,000 iPS throughout follow-up. E, iPS transplantation within infarcted myocardium of immunocompetent hosts produced stable engraftment detected by live-cell imaging throughout the 4 week follow-up. F, Post-ischemic myocardium transplanted with iPS at 4 weeks demonstrated rare pockets of SSEA-1 positive progeny. Bar=10 µm. G, Subcutaneous (sc) transplantation produced teratoma in immunodeficient (deficient), in contrast to tumor-free outcome in all immunocompetent (competent) hosts. H, Normal pre-infarction (Pre) sinus rhythm was maintained following iPS transplantation throughout the 4 week follow-up, with P-waves (triangles) preceding each QRS complex (stars) with no ventricular tachycardia or ectopy.
Figure 19C:
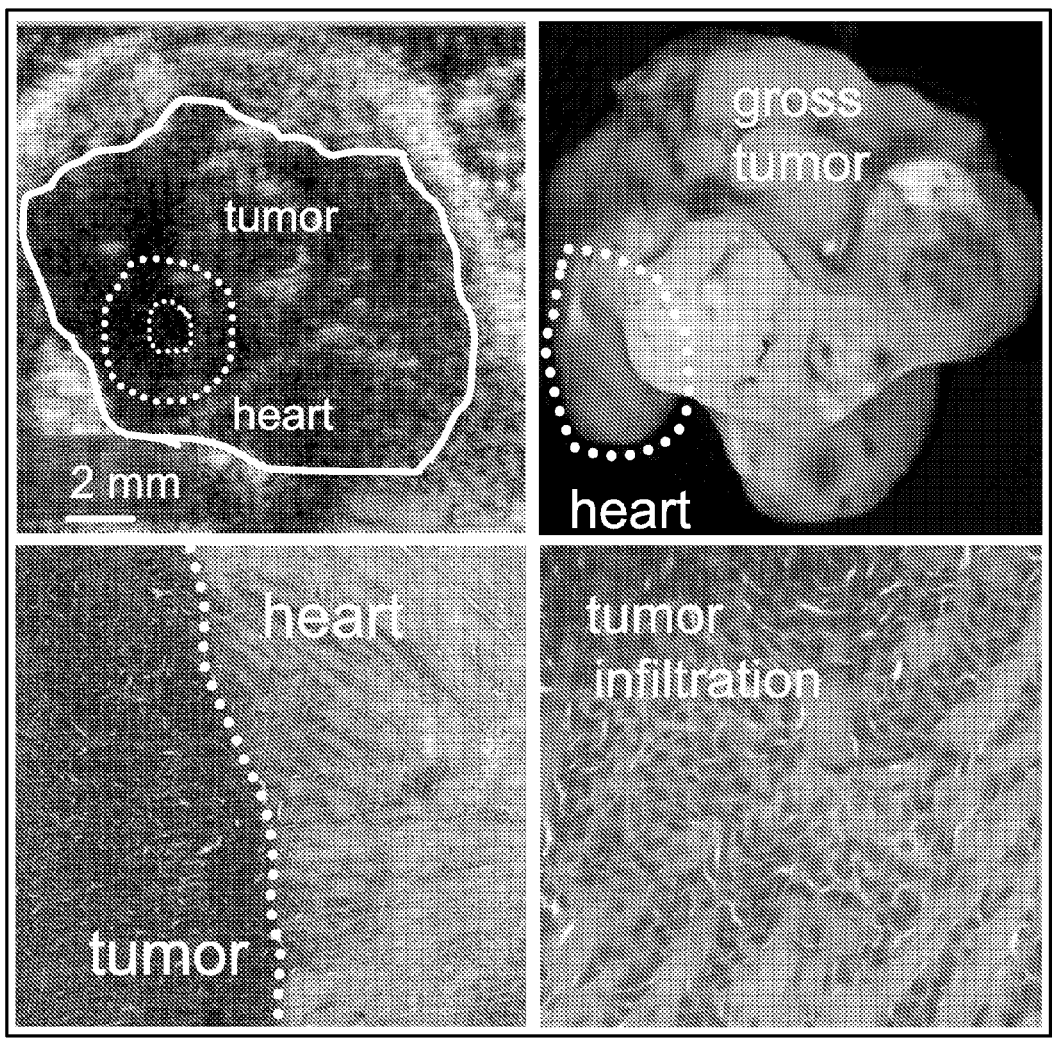
Figures 19D, 19E:
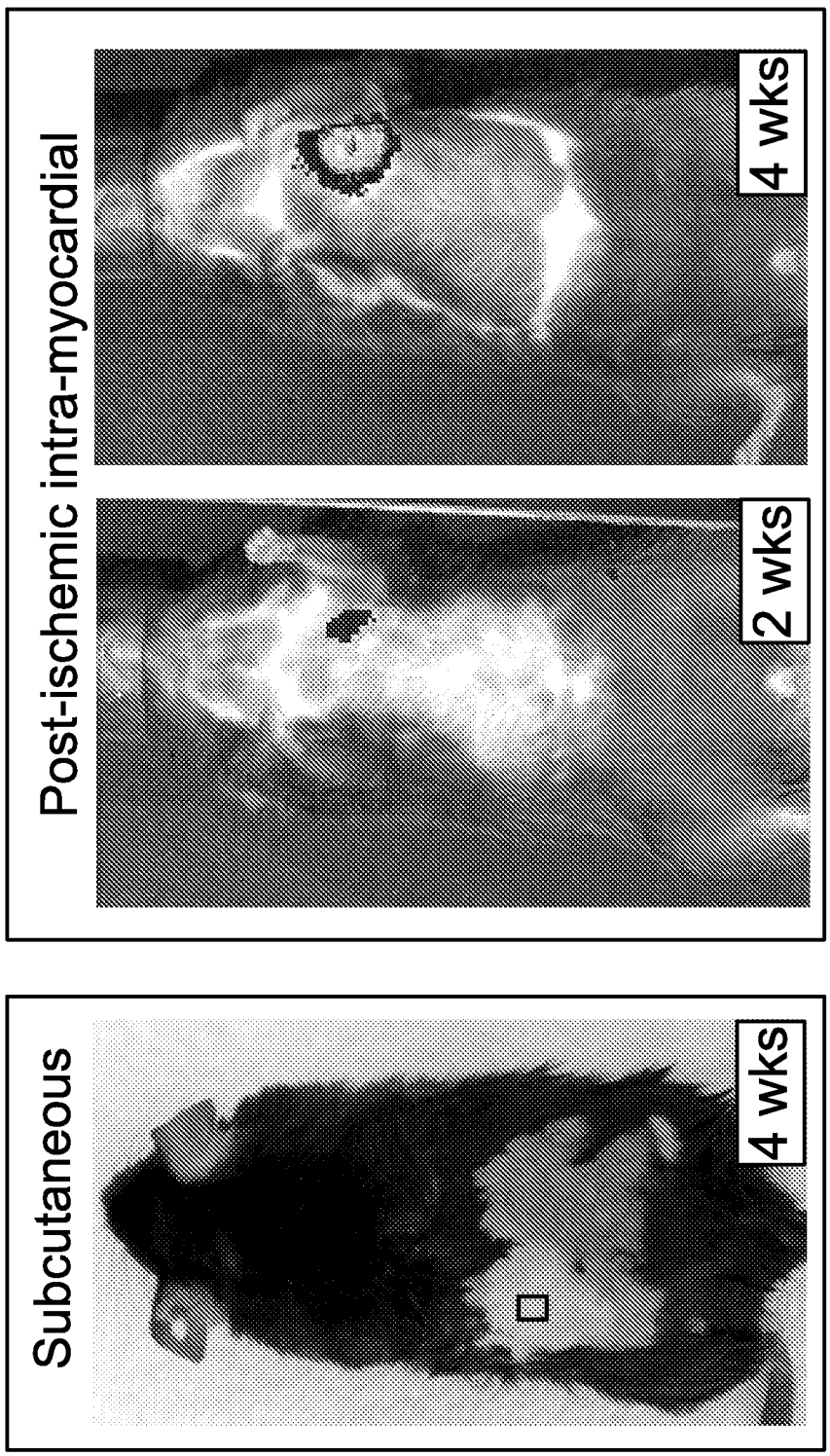
Figure 19F:
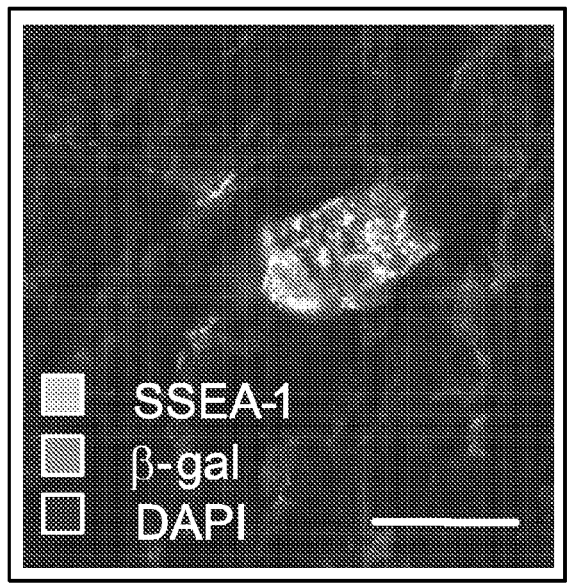
Figure 19G:
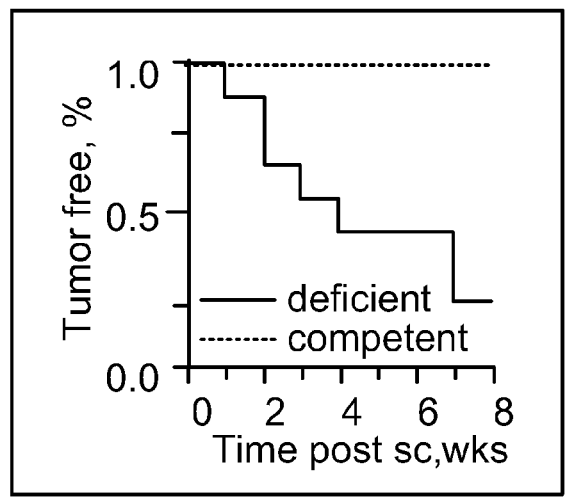
Figure 19H:
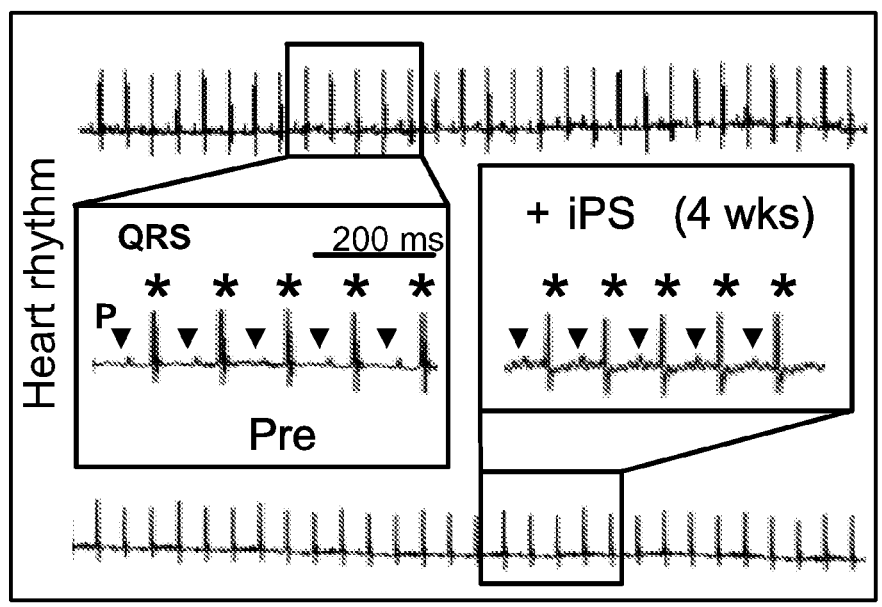

In contrast to fibroblasts unable to proliferate even after prolonged incubation, subcutaneous injection of iPS clones within an immunodeficient adult environment demonstrated aggressive growth (FIG. 19A). Transplanted cells, initially labeled with retroviral reporter constructs and expanded through multiple passages (>5) in vitro, were tracked with in vivo imaging using emitted bioluminescence from iPS-derived progeny. Upon permanent occlusion of epicardial coronary vasculature and microsurgical transfer into the ischemic myocardium, iPS remained within injected hearts and produced gradual tumor outgrowth between 2-4 weeks (FIG. 19B). Echocardiography confirmed a significant tumor burden, which compromised hemodynamics 4-weeks post-transplant (FIG. 19C). Autopsy in immunodeficient recipients (n=6) verified consistent teratoma formation with extension beyond the myocardial wall and tumor infiltration within the post-injured myocardium (FIG. 19C). In contrast to tumorigenesis that compromised the safety within immunodeficient environments, subcutaneous transplantation of iPS into immunocompetent hosts demonstrated a persistent absence of tumor growth in all animals (n=6) even at 8 weeks of follow-up (FIG. 19D). Furthermore, intramyocardial transplantation of 200,000 iPS/heart, a dose selected based on tumor-free outcome with embryonic stem cell intervention (Behfar et al., *J. Exp. Med.*, 204:405-420 (2007) and Behfar et al., *FASEB J.*, 16:1558-1566 (2002)), produced stable engraftment without detectable tumor formation (n=6; FIG. 19E). According to bioluminescence emitted from labeled progeny, differentiated iPS within ischemic immunocompetent hearts were detectable by 2 weeks post-transplantation without metastatic dissemination after 4 weeks of engraftment (n=6; FIG. 19E). In fact, immunostaining of hearts at 4 weeks demonstrated rare iPS progeny positive for SSEA-1 expression within the post-ischemic myocardium (FIG. 19F). Immunocompetent recipients thus ensured controlled iPS engraftment (FIG. 19G) with tissue integration that did not perturb electrical homeostasis (n=6; FIG. 19H). In this way, the immunocompetent adult host provided a permissive environment for differentiation, offering the opportunity to test the therapeutic potential of iPS clones.

iPS Therapy Restores Myocardial Performance Lost by Ischemic Injury.

Figure 20A:
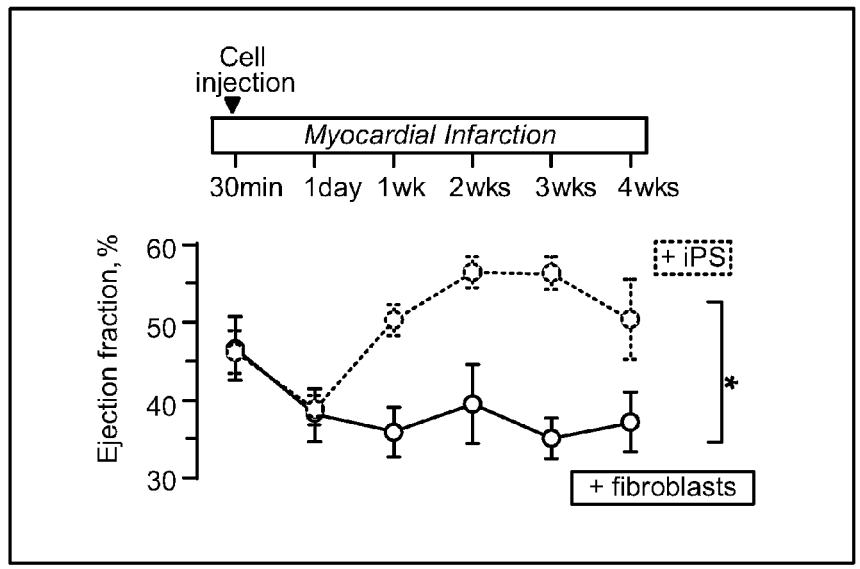
FIG. 20. iPS restored function following acute myocardial infarction (MI). A, Upon randomization, cell-based intervention was performed at 30 minutes after coronary ligation. Divergent ejection fractions were noted in iPS (n=6) versus fibroblast (n=6) treated hearts within 1 week post-therapy, maintained throughout follow-up. *p=0.002 using two-way repeated measures ANOVA. B, Fractional shortening was similar at day 1 post-infarction, but significant improvement was only observed in iPS-treated hearts. Line indicates median value. *p=0.01. C, Septal wall thickness was preserved in systole following iPS (n=6) compared to fibroblast (n=6) treatment. *p=0.006. D, Echocardiography with long-axis views revealed anterior wall thinning and apex aneurysmal formation (arrow heads) in fibroblast-treated hearts as indicated by akinetic wall (left) in contrast to normalized systolic wall motion in iPS-treated hearts (right). E, Short-axis confirmed thinning in the anterior wall (black bar) and overall decreased cardiac performance with fibroblast compared to iPS-based interventions. The larger and smaller dotted lines indicate endocardium and epicardium, respectively. LVVd: left ventricular volume in diastole; LVVs: left ventricular volume in systole.
Figure 20B:
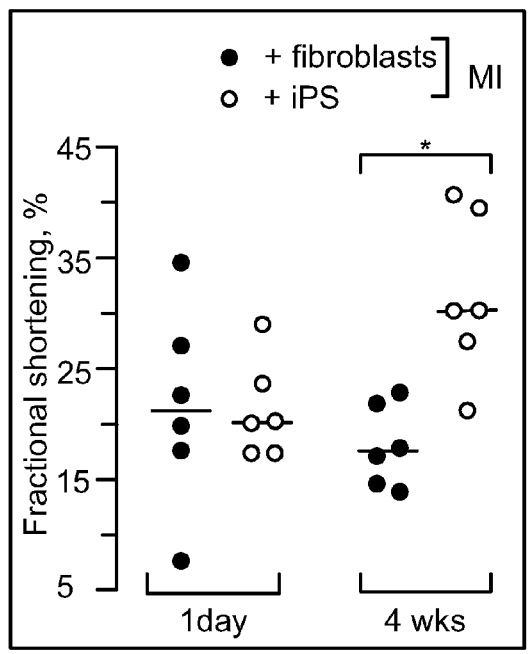
Figure 20C:
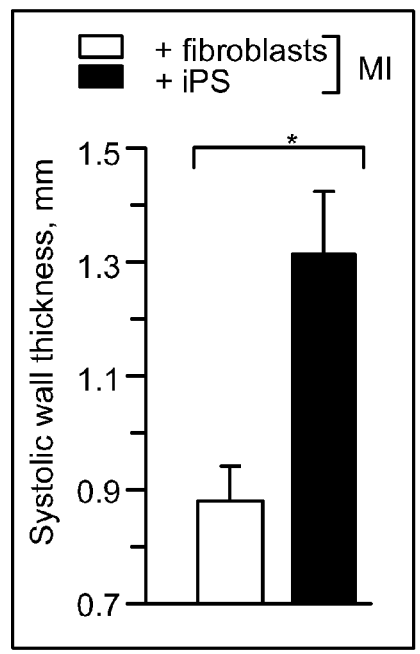
Figure 20D:
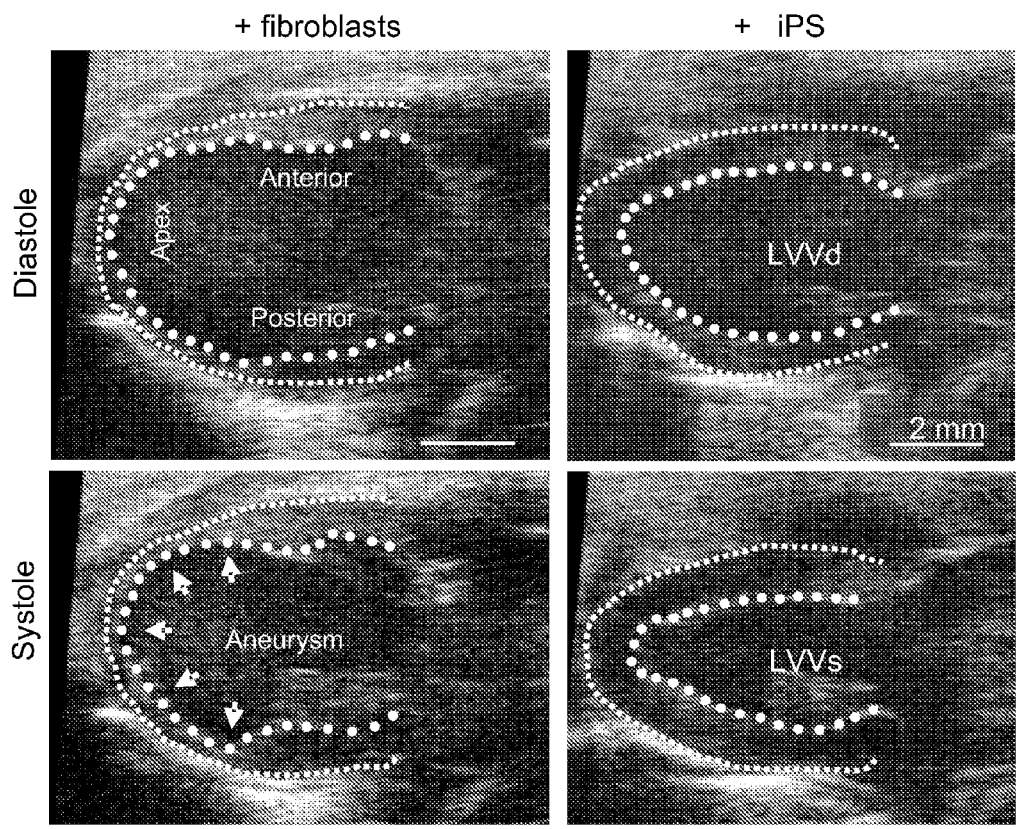
Figure 20E:
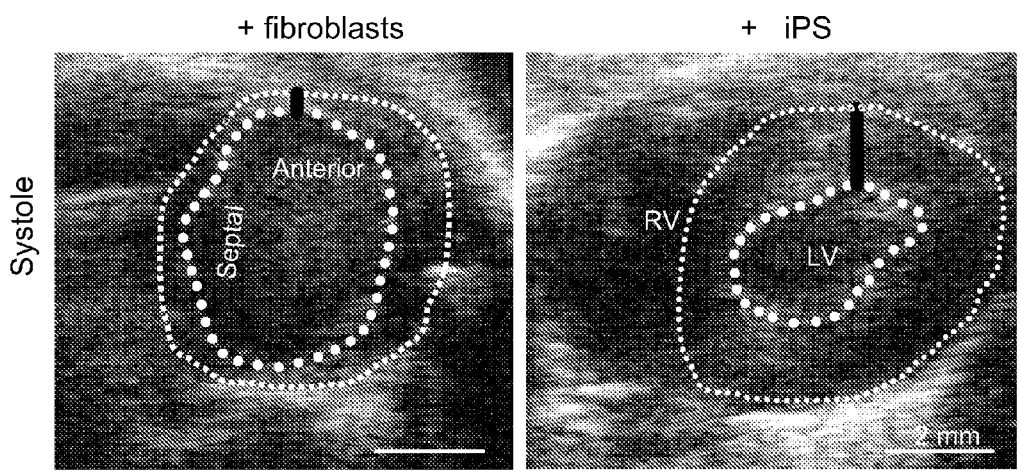

Within immunocompetent hosts, recovery of post-ischemic cardiac performance was compared in randomized cohorts transplanted with parental fibroblasts versus derived iPS. Monitored by echocardiography, irreversible occlusion of the epicardial coronary blood flow consistently impaired anterior wall motion, depressed global cardiac function, and halved ejection fraction (EF) from 82±3% before infarction (n=8) to 38±3% within 1-day post-infarction (n=12; FIG. 20A). While blinded transplantation with parental fibroblasts demonstrated persistent functional decline with EF dropping to 37±4% at 4 weeks (n=6), iPS intervention improved cardiac contractility to achieve an EF of 56±2% within the first 2-weeks of therapy and 50±5% by 4 weeks (n=6; p=0.002 iPS versus fibroblasts, FIG. 20A). Functional benefit in response to iPS was verified by the improved fractional shortening, from 20±1% (median 18%, n=6) at 1-day post-infarction to 31±3% (median 29%, n=6) after 4-weeks, in contrast to a lack of recovery in fibroblast-treated hearts (n=6, p=0.01; FIG. 20B). Moreover, the regional septal wall thickness in systole was significantly rebuilt with iPS (1.31±0.11 mm, median 1.20 mm, n=5), but not with fibroblast (0.88±0.06 mm, median 0.90 mm, n=6) treatment (p=0.006; FIG. 20C). Impaired cardiac contractility in the injured anterior wall resulted in akinetic regions with paradoxical motion in systole indicative of aneurysms in fibroblast-treated hearts, in contrast to coordinated concentric contractions in response to iPS treatment visualized by long-axis and short-axis imaging (FIGS. 20D and 20E). Thus, compared to non-reparative parental fibroblasts, iPS intervention improved functional performance following acute myocardial infarction.

iPS Therapy Halts Progression of Pathologic Remodeling in Infarcted Hearts.

Figure 21A:
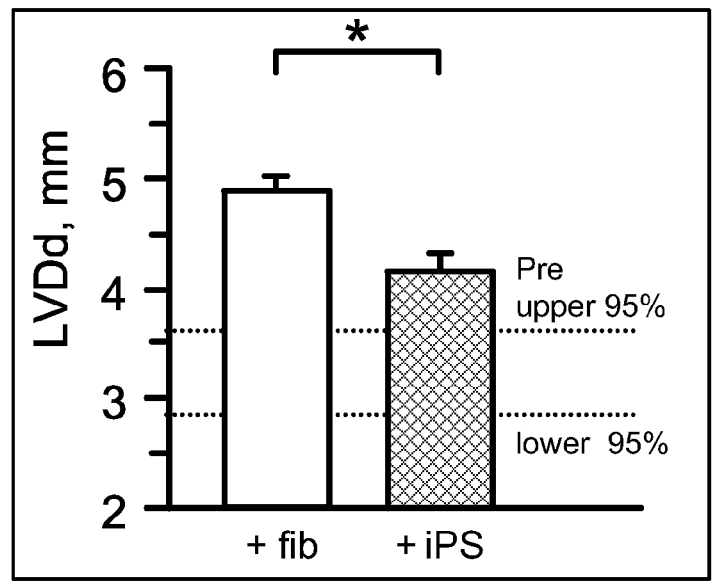
FIG. 21. iPS halt maladaptive remodeling and preserve structure. A, Diastolic parameters revealed a significant decrease in global left ventricular diastolic diameter (LVDd) in hearts treated with iPS (n=6) compared to fibroblasts (n=6) at 4-weeks post-therapy (*p=0.007). B, M-mode echocardiography demonstrated dilated ventricular lumen with reduced anterior and septal wall thickness (SWTd) during systole in fibroblast-treated hearts (upper), which improved with iPS intervention (lower). C, Time required for ventricular repolarization and depolarization, measured by the QT interval, was significantly prolonged in fibroblast (n=6) compared to iPS (n=6) treated hearts. *p=0.004. D, Hearts were pathologically enlarged in the fibroblast-treated group with aneurysmal formation (+) and severe wall thinning (+) visible with translumination compared to structurally preserved iPS-treated hearts with normal apex geometry (−) and opaque thick walls (−) on right anterior-oblique (RAO) view upon transverse sectioning of hearts immediately inferior to the site of surgical ligation (dotted line). Bar=5 mm. Aneurysm delineated by yellow dotted circle. RA: right atrium; LA: left atrium; LV: left ventricle; s: suture; SWTd: septal wall thickness in diastole; SWTs: septal wall thickness in systole; PWTd: posterior wall thickness in diastole; PWTs: posterior wall thickness in systole.
Figure 21B:
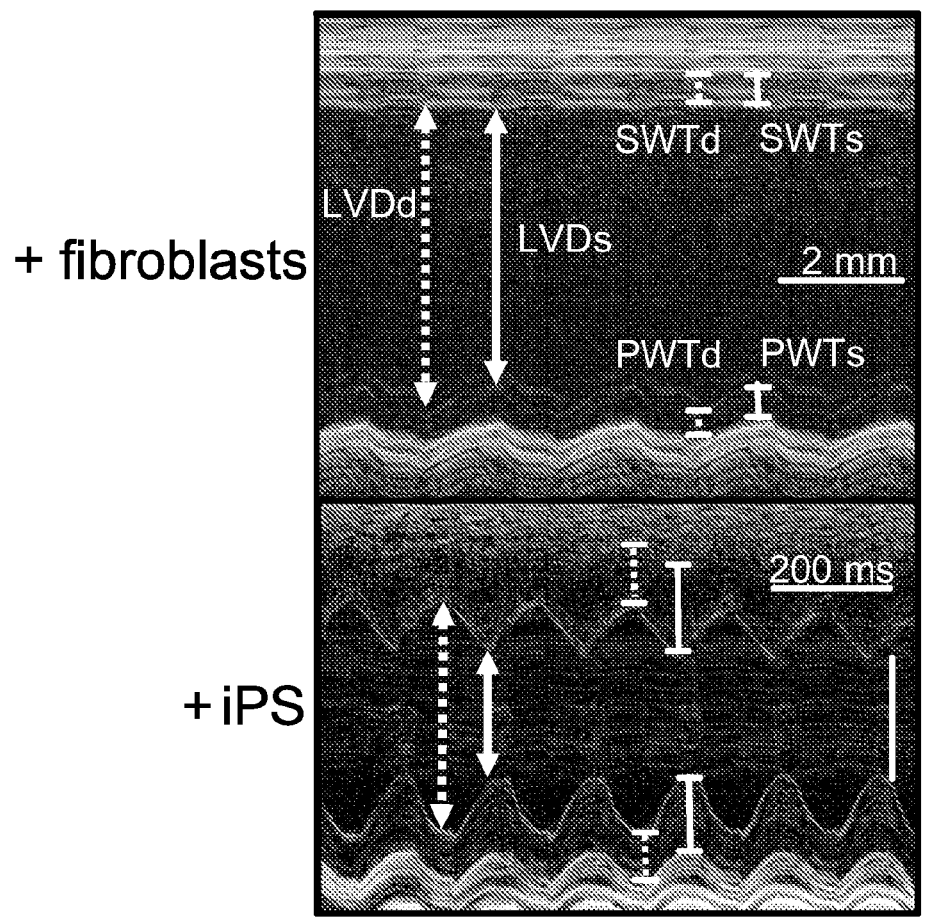
Figure 21C:
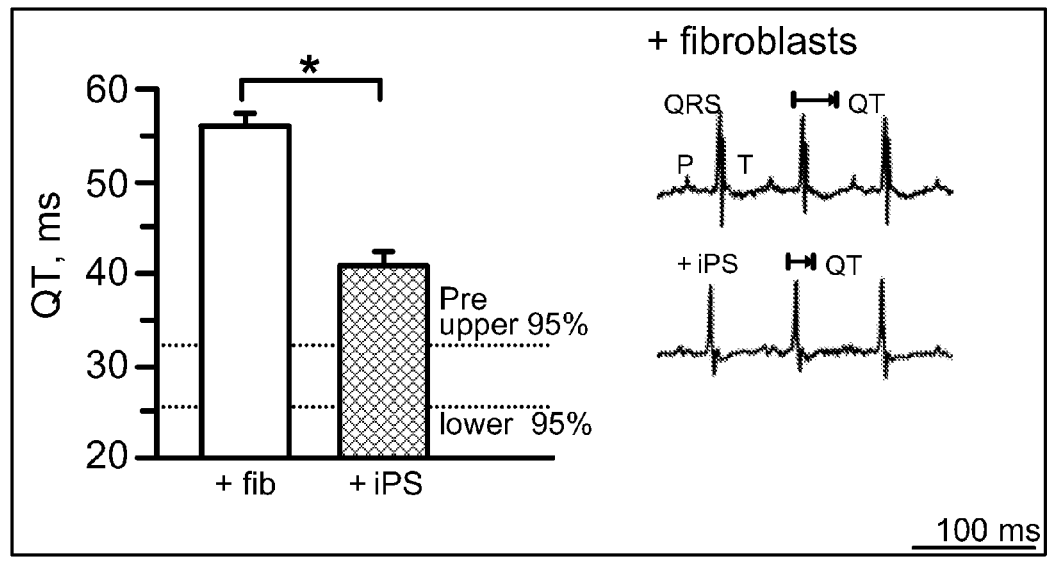
Figure 21D:
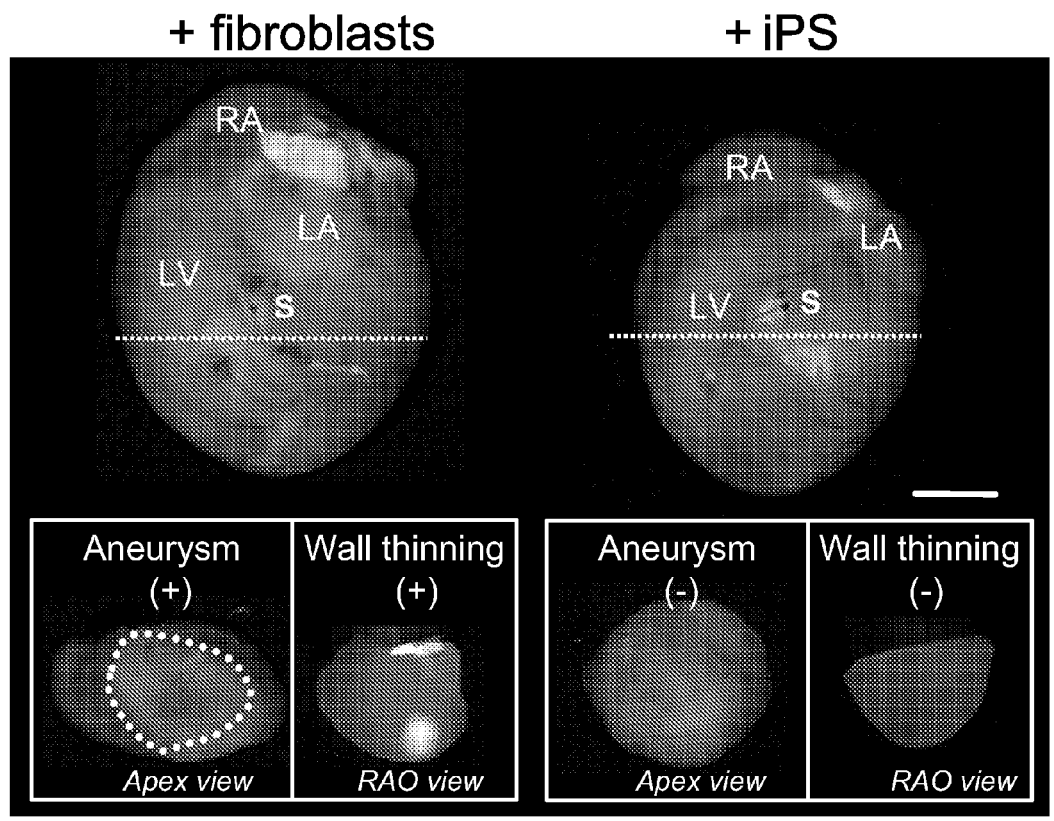

Beyond functional deterioration, maladaptive remodeling with detrimental structural changes prognosticates poor outcome following ischemic injury. Here, iPS-based intervention attenuated global left ventricular diastolic diameter (LVDd). Pre-infarction LVDd measured 3.2±0.1 mm (median 3.1 mm), but increased post-infarction to 4.9±0.1 mm (median 4.9 mm) by 4-weeks of fibroblast treatment (n=6) a value significantly higher (p=0.007) than 4.2±0.2 mm (median 4.2 mm) with iPS treatment (n=6; FIG. 21A). Furthermore, echocardiography demonstrated regional structural deficits with deleterious wall thinning and chamber dilation in fibroblast-treated hearts (n=6), rescued by iPS intervention (n=6; FIG. 21B). Pathologic structural remodeling leads to electrophysiological consequences with prolongation of the QT interval, which increases risk of arrhythmia. Infarction increased QT interval from 28.9±1.4 ms (median 28.1 ms) to 55.9±1.3 ms (median 55.8 ms) in fibroblast-treated hearts (n=6), which was abrogated to 40.8±1.5 ms (median 40.3 ms, n=6) with iPS treatment (p=0.004, FIG. 21C). These real-time surrogates for tissue remodeling were confirmed on autopsy on inspection of gross specimen that demonstrated reduced heart size, lack of aneurysmal formation, and absence of severe wall thinning in iPS compared to fibroblast-treated hearts (FIG. 21D). Collectively, the favorable remodeling at global, regional, and electrical levels demonstrates overall benefit of iPS therapy in the setting of myocardial infarction.

Multi-lineage Cardiac Tissue Regeneration Following iPS Therapy.

Figure 22A:
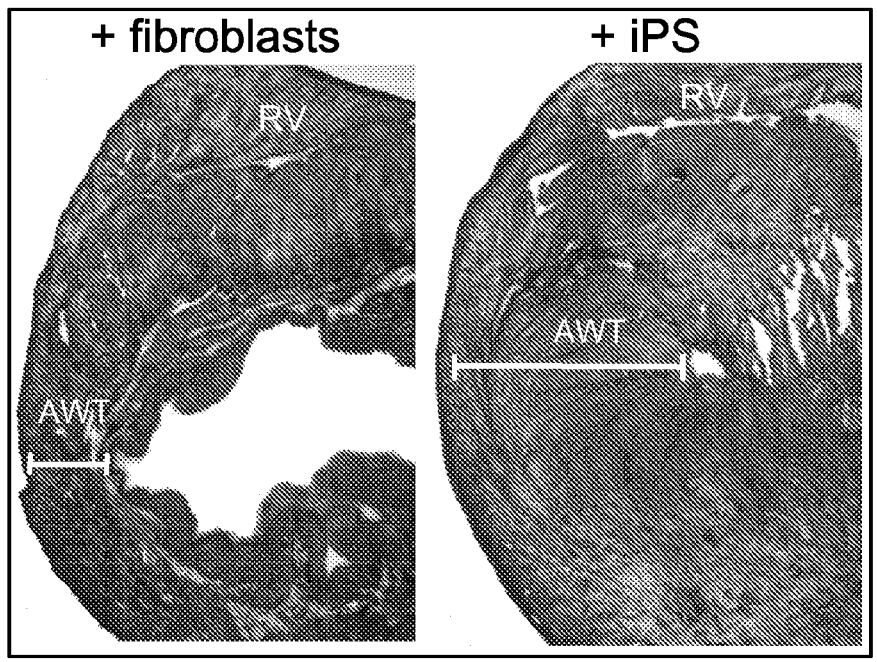
FIG. 22. iPS treatment reduced scar and contributed to multi-lineage reconstruction. A, After 4 week of therapy, Masson's trichrome staining demonstrated reduced anterior wall thickness (AWT) and fibrosis in hearts treated with fibroblasts (left) compared to iPS (right). B, Autopsy demonstrated tumor-free heart, liver, lung, or spleen in the iPS-treated cohort. C, After 4 weeks, integrated iPS progeny expressed markers of remuscularization according to α-actinin (right) and β-gal co-expression (arrow heads), not detectable with fibroblast treatment (left). D, Smooth muscle actin (α-SMA; arrow head), and E, CD31 positive endothelium (arrow heads) were identified in iPS progeny (right) compared to no expression with fibroblast treatment (left). DAPI visualized nuclei. Bar=5 µm.
Figure 22B:
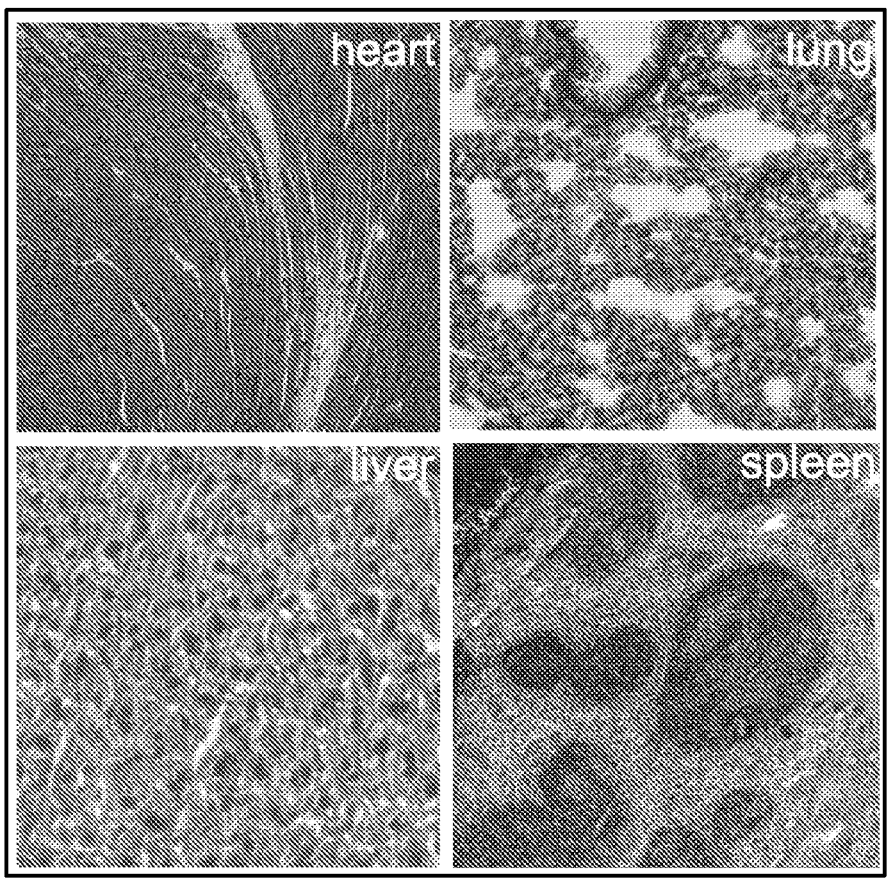
Figure 22C:
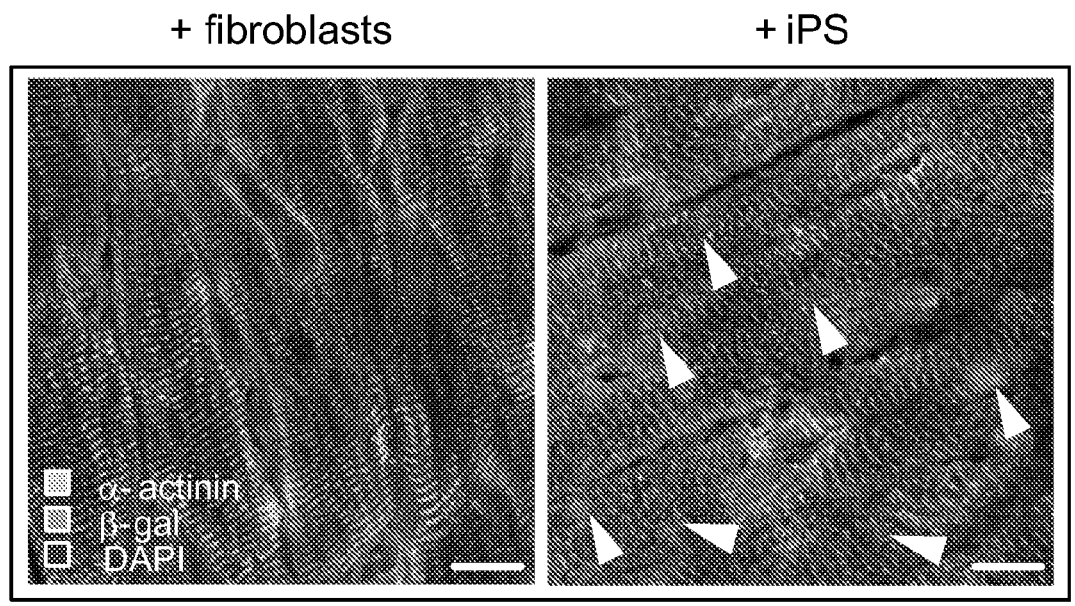
Figure 22D:
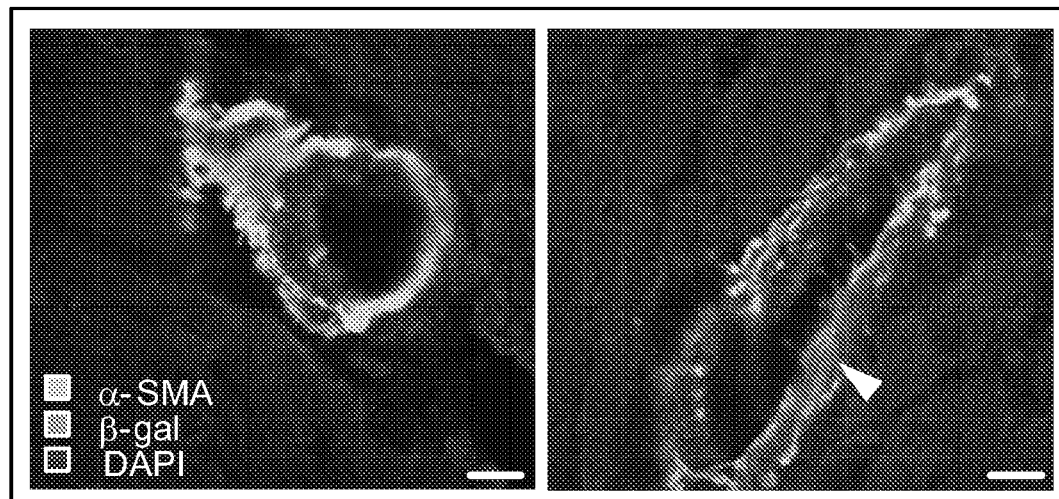
Figure 22E:
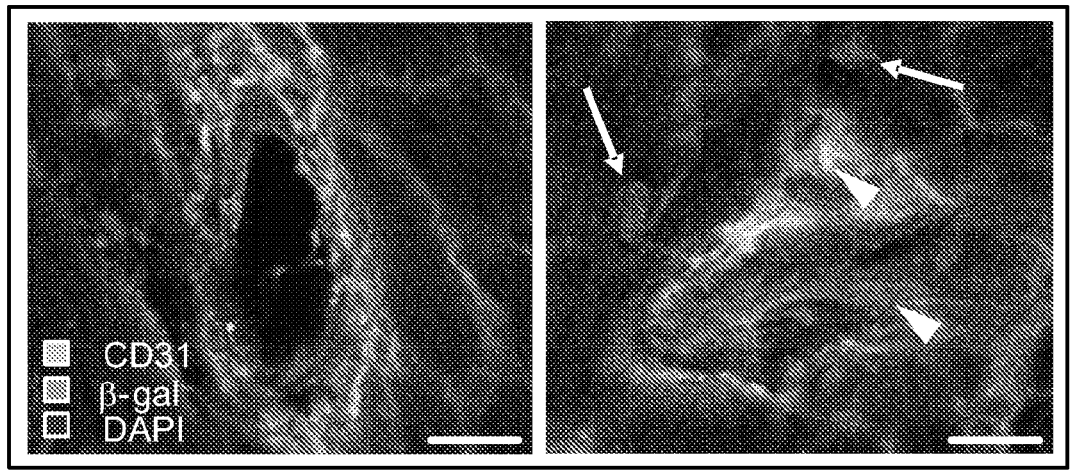

Histological analysis demarcated de-muscularization and extensive scarring within left ventricles distal to coronary ligation in hearts treated with fibroblasts 4 weeks following transplantation (FIG. 22A). In contrast, iPS treatment halted structural deterioration of infarcted tissue with anti-fibrotic benefit and remuscularization within the left ventricular free wall (FIG. 22A). Surgical dissection and post-mortem histopathological analysis verified absence of tumor infiltration or dysregulated cell expansion following iPS transplantation in the myocardium itself, as well as in the liver, lung and spleen—organs with high metastatic risk (n>10 staggered sections throughout respective organs; FIG. 22B). In post-ischemic myocardium, immunohistochemistry confirmed engraftment of iPS-derived progeny that expressed transgene markers luciferase (not illustrated) or β-galactosidase (FIG. 22C-E). Co-localization of transgene expression with cardiac α-actinin was consistent within the damaged territory as documented by microscopy of serial transverse sections (n>10 at 10-20 μm intervals) immediately adjacent to the site of coronary ligation (FIG. 22C). Smooth muscle α-actin (FIG. 22D) and endothelial CD31 (FIG. 22E) were also detectable, albeit at lower frequency, consistent with multi-lineage cardiovascular differentiation of iPS. Thus, in contrast to ineffective parental fibroblasts, targeted delivery of iPS generated de novo cardiovascular tissue in post-ischemic adult myocardium.

Example 8

Induced Pluripotent Reprogramming

Fibroblasts

Mouse embryonic fibroblasts (MEFs) were obtained from embryos at 14.5 days post coitum (dpc). Internal organs and the head were removed prior to digestion with 0.25% trypsin-EDTA (Invitrogen, Carlsbad, Calif., USA). Digestion was performed three times. Obtained suspension was inactivated with equal volume of EmbryoMax Dulbecco's modified Eagle's medium (DMEM; Millipore, Billerica, Mass., USA) supplemented with 10% fetal calf serum (FCS), 1% L-glutamine (Invitrogen), and penicillin/streptomycin (Invitrogen). Resulting fibroblasts were plated and grown to confluence in the same medium for two passages. Transduced MEFs were maintained in DMEM (Millipore) supplemented with pyruvate (Lonza, Basel, Switzerland) and L-glutamine (Invitrogen), nonessential amino acids (Mediatech, Herndon, Va., USA), 2-mercaptoethanol (Sigma-Aldrich, St. Louis, Mo., USA), 15% FCS (Invitrogen), and LIF (Millipore).

HIV Packaging Plasmid

The parental packaging plasmid pCMVR8.9129 was used to engineer modifications in the HIV-1 capsid region for increased vector transduction efficiency (Ikeda et al., *J. Virol.*, 78(21):11816-11822 (2004) and Kootstra et al., *Proc. Natl. Acad. Sci. USA*, 100(3):1298-1303 (2003)). To generate HIV-1 packaging constructs carrying the capsid mutations, the ApaI, BglII, and SpeI sites in the uncoding region of pCMVR8.9129 were deleted (p8.9Ex). Naturally occurring capsid amino acid substitutions, which affect the HIV cyclophilin A (Cyp A) dependency, were introduced into the capsid region of the gag gene, resulting in pEx-HV, pEx-QI, and pEx-QV. Vesicular stomatitis virus glycoprotein G (VSV-G)-expressing plasmid, pMD.G (Zufferey et al., *Nat. Biotechnol.*, 15(9):871-875 (1997)) was used for pseudotyping HIV-1 vector particles. Infectious HIV vectors were generated by packaging a green fluorescent protein (GFP)-carrying HIV vector genome with the modified constructs and VSV-G, and vector amounts were normalized by the levels of endogenous reverse transcriptase (RT) activity in vector particles. Human, simian, and murine cell lines were infected with various amounts of GFP-expressing vectors, and GFP-positive cell populations were analyzed using fluorescence-activated cell sorting (FACScan, BD Biosciences, Franklin Lake, N.J., USA) and automated quantification (CELL QUEST software; Becton Dickinson, Franklin Lake, N.J., USA). Vector infectivity in each target cell line was determined by infectious units per nanogram RT activity. For MEF transduction, GFP-carrying HIV vectors were generated with a conventional HIV packaging construct (p8.9Ex) or a packaging construct with the V83L, H87Q, and 191V capsid substitutions (pEx-QV). To determine transduction efficiencies, $5 \times 10^4$ MEFs were infected with increasing amounts of unconcentrated vectors overnight. The number of infected MEFs was determined by GFP-positive cells using FACScan.

HIV-based Transfer Vectors pSIN-CSGWdlNotI was generated by deleting one of the two NotI sites in the GFP-expressing HIV vector construct, pSIN-SEW (Demaison et al., *Hum. Gene Ther.*, 13(7):803-813 (2002)), which allowed one-step cloning of genes of interest by BamHI and NotI. Transfer vectors were generated with full-length human Oct3/4, Sox2, Klf4, and c-Myc cDNAs (Open Biosystems, Huntsville, Ala., USA) amplified using the primer pairs Oct3/4 (5'-ATAGGATC-CGCCAC-CATGGCGGGACACCTGGCTTCG GAT-3' (SEQ ID NO:1) and 5'-ATAGCGGC-CGCTCAGTTTGAATG-CATGGG AGAGCC-3' (SEQ ID NO:2), BamHI-NotI), Sox2 (5'-ATA-GGATCCACCATGTACAACATGATGGA-GACGAGC-3' (SEQ ID NO:3) and 5'-ATAGCG-GCCG CTCACATGTGTGAGAGGGGCAGTGT-3' (SEQ ID NO:4), BamHI-NotI), Klf4 (5'-GACGAATTCGGATC-CACCATGAGGCAGCCACCTGGC GAGTCTG-3' (SEQ ID NO:5) and 5'-GACCTCGAGCGGCCGCTTAAAAATG CCTCTTCATGTGTAAG-3' (SEQ ID NO:6), BamHI-XhoI), and c-Myc (5'-GC CTGATCAAGGCTCTCCTT-GCAGCTGCTTAGACG-3'(SEQ ID NO:7) and 5'-ATAGCGGCCGCTTACGCACAAGAGTTCCG-TAGCTG-3' (SEQ ID NO:8), BclI-NotI) cloned into the pSIN-CSGWdlNot1, resulting in pSIN-Oct3/4, pSIN-Sox2, pSIN-Klf4, and pSIN-c-Myc. Human sternness-related factors were driven by a spleen focus-forming virus (SFFV) promoter. HIV vectors were produced by transient transfection of 293T cells using FuGene6 (Roche, Indianapolis, Ind., USA) with a weight ratio of 2:1:1 of vector to packaging to VSV-G plasmids (Ikeda et al., *J. Virol.*, 78(21):11816-11822 (2004)). Transfected cells were washed and grown for 48 hours, and supernatants were harvested and passed through a 0.45-μm filter. Vector supernates (10 mL) were concentrated by ultracentrifugation ($10^4$ g, 2 hours at 4° C.), resuspended in 500 μL of serum-free media, aliquoted, and stored at −80° C. For reprogramming, vector titers were determined in MEFs by FACS for GFP-expressing vectors and by immunostaining for stemness factor-encoding vectors.

Western Blot

293T/17 cells (CRL-11268; ATCC, Manassas, Va., USA) were maintained in DMEM (Invitrogen) supplemented with 10% FCS and antibiotics. Western blots were run on 12% SDS-PAGE gels and transferred to PVDF membranes using the semi-dry method. The membranes were then blocked overnight. Anti-Oct4 (no. 2750S) and anti-Sox2 (no. 2748S) antibodies (Cell Signaling, Boston, Mass., USA), anti-c-Myc antibody (Santa Cruz Biotechnology, Santa Cruz, Calif., USA), and anti-KLF4 (ab26648-25) antibody (Abcam, Cambridge, Mass., USA) were used to verify the expression of human stemness factors in vector-infected cells.

Immunofluorescence

To determine the expression levels, native and transduced MEFs were labeled with anti-Oct4, anti-Sox2, anti-c-Myc, and anti-KLF4 antibodies along with the FITC-conjugated donkey anti-mouse IgG secondary antibody for c-Myc (Jackson Immuno Research, West Grove, Pa., USA), and fluorescein isothiocyanate (FITC)-conjugated donkey anti-rabbit IgG for Oct3/4, Sox2, and Klf4 (Jackson Immuno Research). To determine reactivation of pluripotent markers, isolated cell lines were stained with anti-SSEA1 antibody (MAB4301; dilution 1:50; Chemicon International) and anti-Ki67 antibody (1:200; Neomarkers, Fremont, Calif., USA) along with secondary antibodies, goat anti-mouse Alexa Fluor 568 (1:250) and goat anti-rabbit Alexa Fluor 488 (1:250; Invitrogen), to visualize markers of undifferentiation. The nuclei were labeled with 4,6'-diamidino-2-phenylindole (DAPI; Invitrogen).

In Vitro Differentiation

Transduced cells were differentiated into three-layer embryoid bodies (EBs) using the hanging-drop method in differentiation media supplemented with 20% FCS without LIF (Behfar et al., *FASEB J.*, 16(12):1558-1566 (2002); Perez-Terzic et al., *Circ. Res.*, 92(4):444-452 (2003); and Behfar et al., *J. Exp. Med.*, 204(2):405-420 (2007)). Briefly, 25-µL drops from a 25,000 cell/mL suspension were cultured on the lid of a plate for 48 hours. EBs were then flushed and kept in suspension for two days to allow spontaneous differentiation for a total of five days.

Detection of Gastrulation Markers

Expression of pluripotency and gastrulation markers was detected by RT-PCR. Total RNA was extracted with a combination of gDNA Eliminator and RNeasy columns (Qiagen, Valencia, Calif., USA). cDNA was prepared from total RNA samples using Superscript III First Strand (Invitrogen). Mouse GAPDH (4352932E; Applied Biosystems, Foster City, Calif., USA) was used as control. Analyzed genes included Fgf4 (Mm00438917_m1), Gsc (Mm00650681_g1), Sox17 (Mm00488363_m1), Pou5f1 (Mm00658129_gH), Zic1 (Mm01239008_mH), and Sox2 (Mm00488369_s1; Applied Biosystems).

Teratoma Formation

Native and transduced fibroblasts were injected subcutaneously into the flank skin of anesthetized athymic nude mice at a dose of 500,000/50 µL medium. Tumor growth was monitored daily until the tissue was harvested. Tumors were processed by rapid freezing and cut by cryosections at 7-µm thickness to be stained with standard hematoxylin/eosin procedures.

Chimeric Blastocyst Formation

In vivo contribution of transduced cells to embryonic development was assessed through diploid aggregation with preimplantation morula. CD1 females at 3 weeks of age were superovulated using intraperitoneal injection of pregnant mare serum gonadotropin and human chorionic gonadotrophin, followed by pairing with adult CD1 males for timed pregnancy. Embryos at 2.5 days dpc were harvested, washed in EmbryoMax M2 medium (Millipore), and denuded from zona pelucida to produce morula competent for stem cell integration. After washing through M2 and EmbryoMax KSOM (Millipore) solutions, the embryos were plated as pairs in microwells to facilitate aggregation. Engineered stem cells were labeled for in vivo imaging by infection with a GFP-carrying HIV vector generated with a conventional HIV packaging construct (p8.9Ex). Labeled cells cultured for at least two passages after thawing were partially digested using trypsin 0.25%-EDTA (Invitrogen) and preplated for 45 minutes to allow attachment of feeders to the plate. Floating clumps (8-15 cells) were individually picked and washed in M2 medium and KSOM medium before being placed adjacent to the pair of embryos in microwells. The aggregation complex was incubated in a table-top incubator (Thermofisher, Waltham, Mass., USA) with continuous flow of a humidified gas mixture (5% $CO_2$/5% $O_2$/90% $N_2$) for 24 hours until cavitation of the blastocysts (Nelson et al., *Phil. Trans. R. Soc. B.*, 364(1514): 269-276 (2008)).

In Utero Organogenesis

CD1 females in estrus were identified and paired with vasectomized studs two days prior to aggregation to produce pseudopregnant mice. Surrogate mothers were anesthetized (2-3% inhaled isofurane), their uteruses were dissected through a minimal flank incision, and blastocyst-stage chimeric aggregates containing transduced cells were transferred into the distal portion of the uterus. Pregnancy was supported by pseudopregnant females until 9.5 dpc when embryos were harvested and analyzed for transduced cell distribution using an LSM 510 laser scanning confocal microscope (Carl Zeiss, Oberkochen, Germany).

Results

Figure 23A:
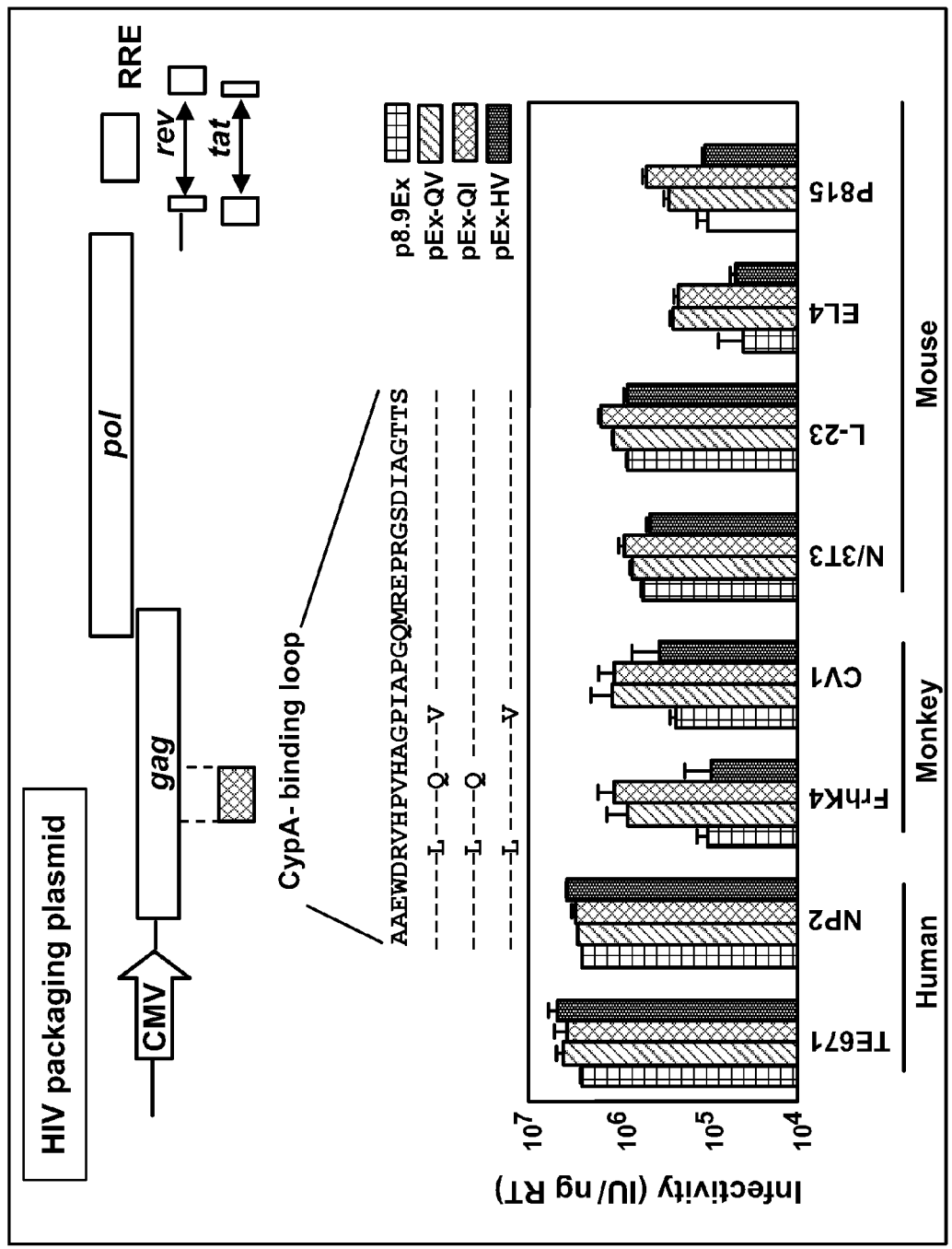
FIG. 23. The H87Q capsid substitution in vector packaging constructs increases HIV vector infectivity across species. (A) Naturally occurring capsid substitutions were introduced into the cyclophilin A-binding region of HIV-1 gag gene of a vector packaging construct, p8.9Ex. Infectious HIV vectors were generated by packaging a GFP-carrying HIV vector genome with the modified constructs, and the amounts of vectors were normalized by the levels of endogenous reverse transcriptase (RT) activity in vector particles. Human, simian, and murine cell lines were infected with various amounts of GFP-expressing vectors, and GFP-positive cell populations were analyzed by flow cytometry. Vector infectivity in each target cell line was determined by infectious units per nanogram RT activity. (B) GFP-carrying HIV vectors were generated with a conventional HIV packaging construct (p8.9Ex) or a packaging construct with the H87Q capsid substitution (pEx-QV). MEFs ($5\times10^4$) were infected with increasing amounts of unconcentrated vectors. The percentage of transfected cells was observed by comparing total cells to GFP-positive cells under UV microscope three days after infection (left panels, with 20 µL of vector input) and analyzed by flow cytometry five days after vector infection (right panel).
Figure 23B:
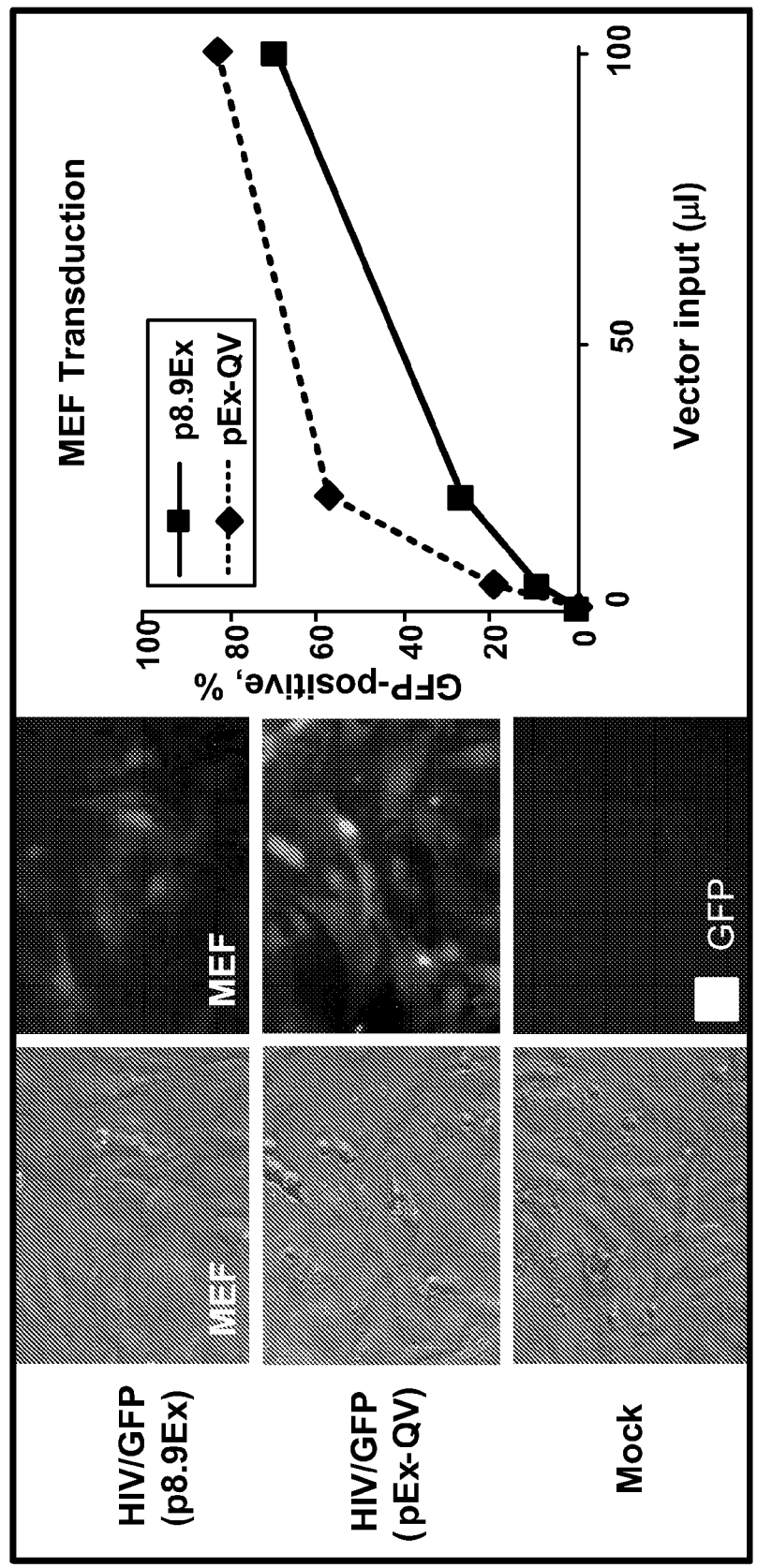

Engineered HIV Vector Packaging Constructs for Improved Transduction Efficiency Across Species Efficient HIV infection requires Cyp A in target human cells, with sequence variations in the Cyp A-binding loop of the capsid protein affecting viral infectivity. Capsid mutations were used here to improve infectivity of HIV-based vectors across species in order to test human sternness-related factors in nonhuman cell types (FIG. 23A). By generating GFP-expressing HIV vectors containing specific mutations in the Cyp A-binding loop region, the efficiency of infectivity was quantified in multiple cell lines. When the vector particle numbers were adjusted to the virion reverse transcriptase activities, the engineered packaging constructs pEx-QV and pEx-QI exhibited improved infectivity when screened in simian FrhK4 or CV1 cells as well as in murine P815 or EL4 cells compared with the parental p8.9-Ex vector without affecting vector infectivity in human cells (FIG. 23A). The absolute infectious vector yields were 2- to 3-fold higher with pEx-QV over p8.9-Ex or modified pEx-QI. Furthermore, the pEx-QV packaged HIV vector transduced MEFs more efficiently than the parental p8.9-Ex (FIG. 23B). The validated packaging construct pEx-QV was therefore selected to deliver sternness-related factors.

Efficient Expression of Human Sternness Factors in Non-human Recipients

Figure 24D:
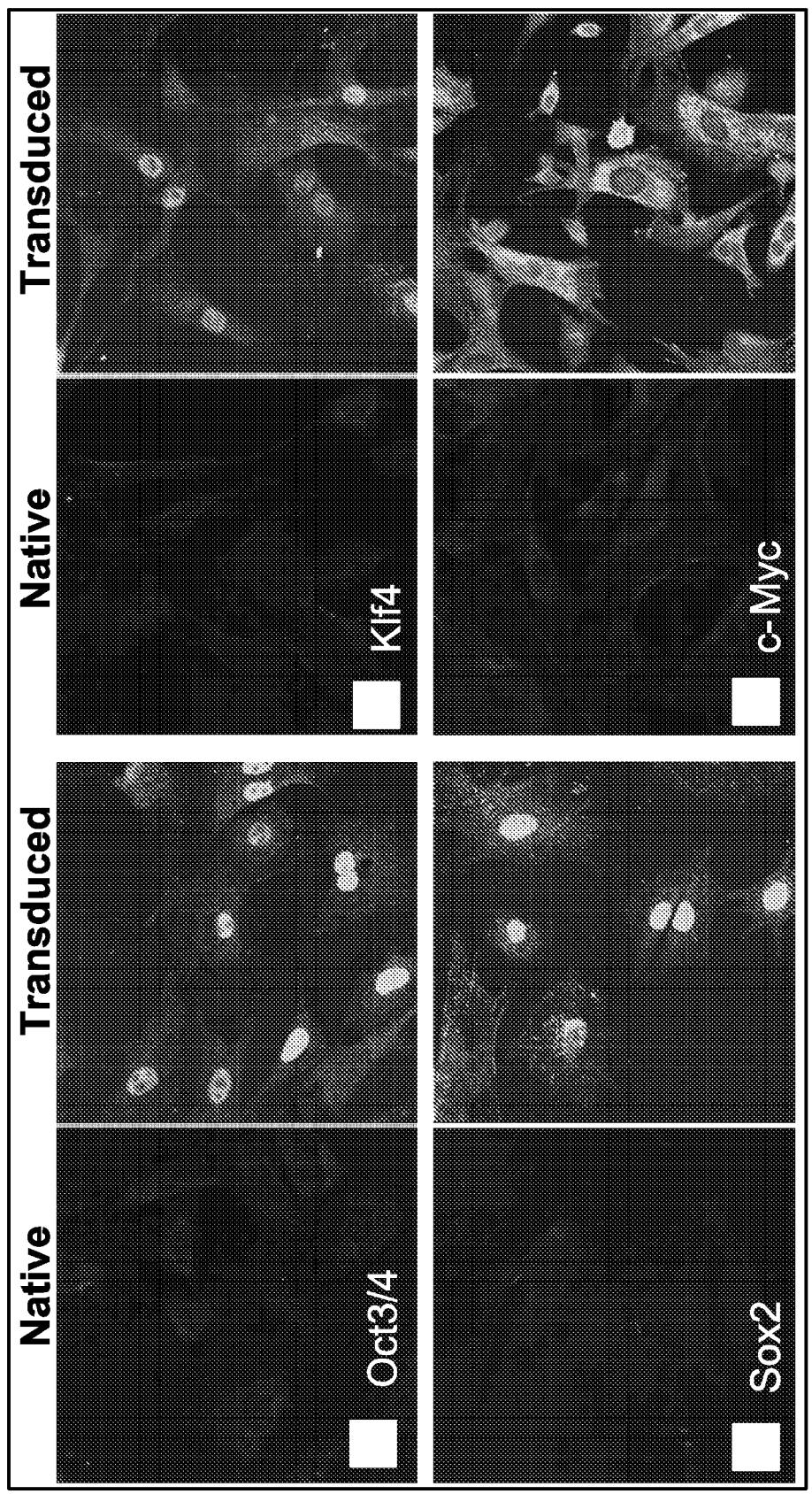
FIG. 24. Efficient expression of stemness-associated factors in human and murine cell types. (A) Percent amino acid homology among orthologous stemness-related factors. Homology for LIF served as benchmark. Homology was determined by LALIGN program (EMBNet). NA=protein sequence not available. (B) Scheme of the HIV-1 vector genome construct used to generate stemness factor-expressing vectors. Ψ=packaging signal; LTR=long terminal repeat; RRE=Rev-responsive element; cPPT=central polypurine tract; SFFV=spleen focus-forming virus promoter; WPRE=Woodchuck hepatitis virus posttranscriptional regulatory element. OCT-3/4, SOX2, KLF4, and c-MYC cDNAs were driven by an internal SFFV promoter. The KLF4-encoding vector lacks WPRE. (C) 293T cells ($2\times10^5$) were infected with 50 μL of the stemness factor-expressing vectors. Three days after infection, expression of full-length stemness factors was verified by Western blotting with respective antibodies. (D) MEFs ($5\times10^4$) were infected with 100 μL of unconcentrated vectors. Expression levels of transgene products were visualized by immunostaining four days following infection.

Human sequences were used to generate reprogramming vector sets to be tested in evolutionary distant somatic cell types. Gene sequences demonstrated a high degree of conservation, with the lowest percentage of homologies noted between Oct3/4 orthologs at 84%. This degree of homology is similar to the sequence for LIF, which does not conserve maintenance of pluripotency in human (Daheron et al., *Stem Cells.*, 22(5):770-778 (2004)) as required for mouse stem cells (FIG. 24A). Human cDNAs for sternness-related factors were amplified by PCR, cloned into self-inactivating vector plasmid, and packaged into the selected pEx-QV HIV packaging construct to produce expression vectors encoding human OCT-3/4, SOX2, KLF4, and c-MYC (FIG. 24B). Proper expression was verified in human 293T cells with predicted molecular weight transgene products detected by immunoblotting with OCT-3/4, SOX2, KLF4, and c-MYC antibodies (FIG. 24C). Robust transgene expression of the four human sternness-related factors was also detected in >90% of MEFs (FIG. 24D). Thus, the pEx-QV HIV-based lentiviral platform demonstrated cross-species tropism and consistently delivered interspecies transduction of human pluripotent genes.

Virus-transduced Human Sternness Factors Reprogram Mouse Fibroblasts

Figures 25A, 25B:
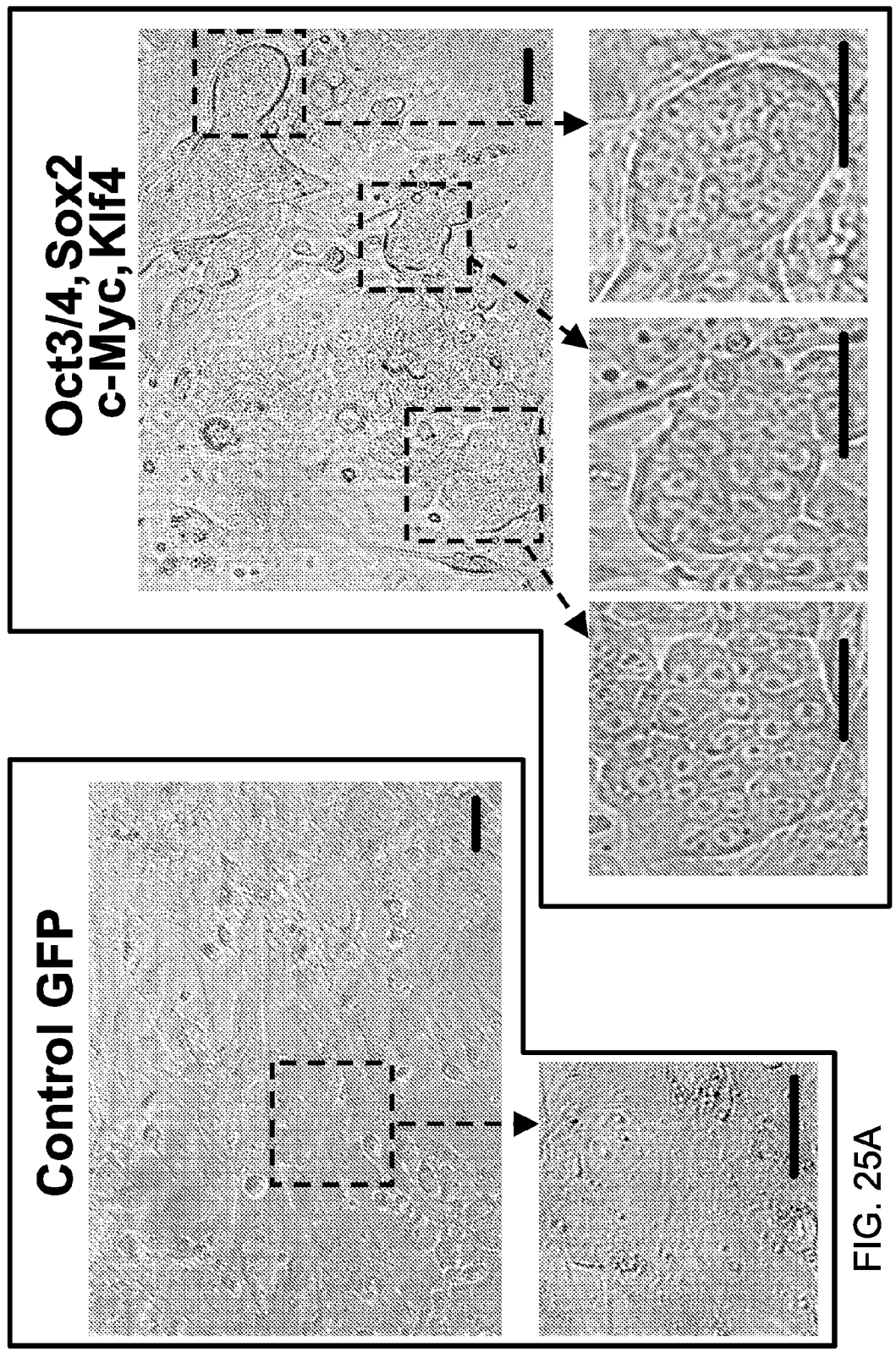

To determine whether human sternness-related factors can reprogram mouse somatic cells, ectopic gene expression was achieved in MEFs. A GFP-expressing vector was infected into MEFs at a multiplicity of infection (MOI) of 20 as the control to determine any spontaneous cellular changes (FIG. 25A). Human pluripotent genes for OCT3/4, SOX2, c-MYC, and KLF4 were transduced together in parallel experiments at an MOI of 5 each (FIG. 25B). Two days post infection, transduced cells were passaged and monitored for the formation of embryonic stem cell-like colonies, according to morphology, consisting of compact cell clusters. In contrast to monomorphic single-cell layered fibroblasts in GFP control groups, MEFs treated with the combination of four human factors produced numerous colonies after 7 days (FIG. 25B, inserts) and were of sufficient size to isolate individual clones after 10 days. Compared with native MEFs (FIG. 25C), clonal expansion of isolated colonies produced rapidly dividing cell lines without contact inhibition and with maintained embryonic stem cell morphology through a minimum of 10 passages (FIG. 25D). Transduced MEFs demonstrated ongoing cell divisions according to Ki67 expression (FIGS. 25E and 25F). In contrast to parental fibroblasts that lack pluripotent markers, transduced cells uniquely expressed the early stage-specific mouse embryonic antigen (SSEA-1; Solter et al., *Proc. Natl. Acad. Sci. USA*, 75(11):5565-5569 (1978)) as a characteristic of stemness (FIGS. 25G and 25H). Thus, the engineered platform based on human stemness factors induced efficient metamorphosis of murine fibroblasts into clonal populations, recapitulating growth kinetics and a cellular expression profile consistent with an embryonic stem cell phenotype.

Figure 26A:
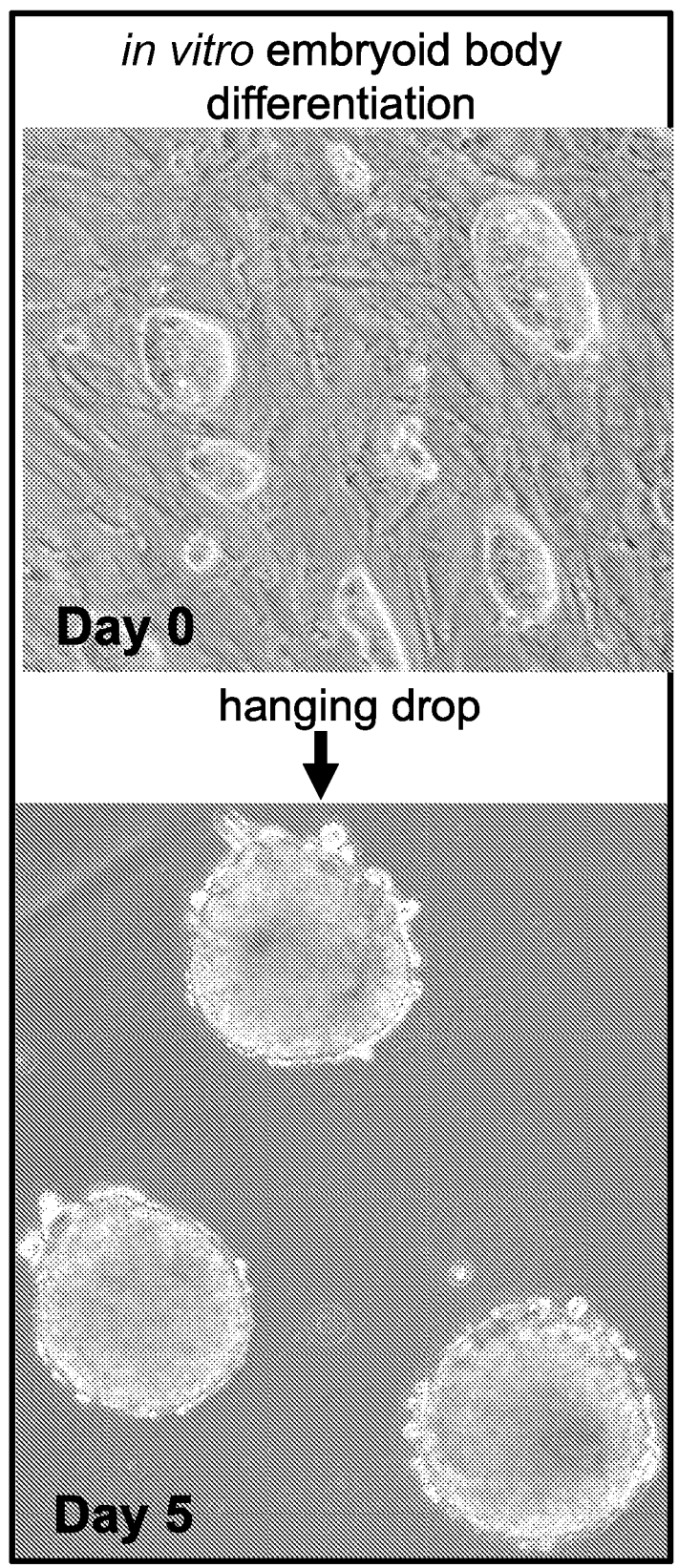
FIG. 26. Gene expression following in vitro differentiation recapitulates gastrulation. (A) Differentiation of transduced cells was facilitated by three-dimensional clustering in a hanging drop to allow spontaneous maturation over a 5-day time course. (B) Pluripotency markers, OCT4, SOX2, and FGF4, were highest in transduced cells at day 0 of differentiation, compared with either native MEFs or transduced counterparts at day 5 post initiation of differentiation. (C) The markers of mesoderm (Gsc), endoderm (Sox17), and ectoderm (Zic1) were higher after five days of differentiation compared with day 0 of differentiation.
Figure 26B:
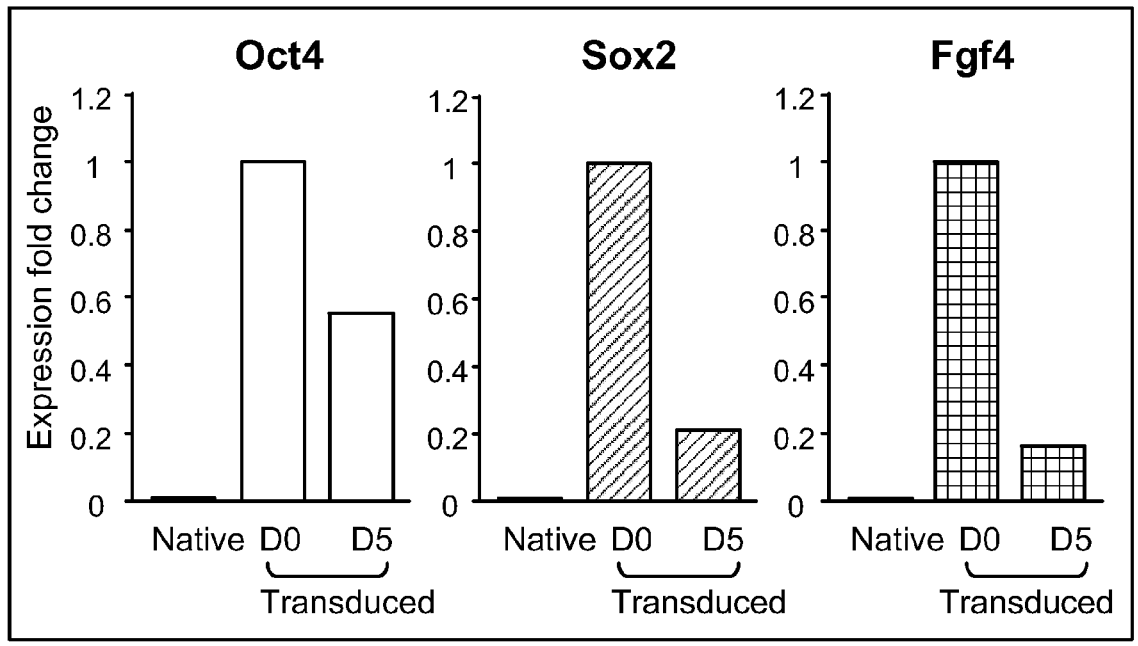
Figure 26C:
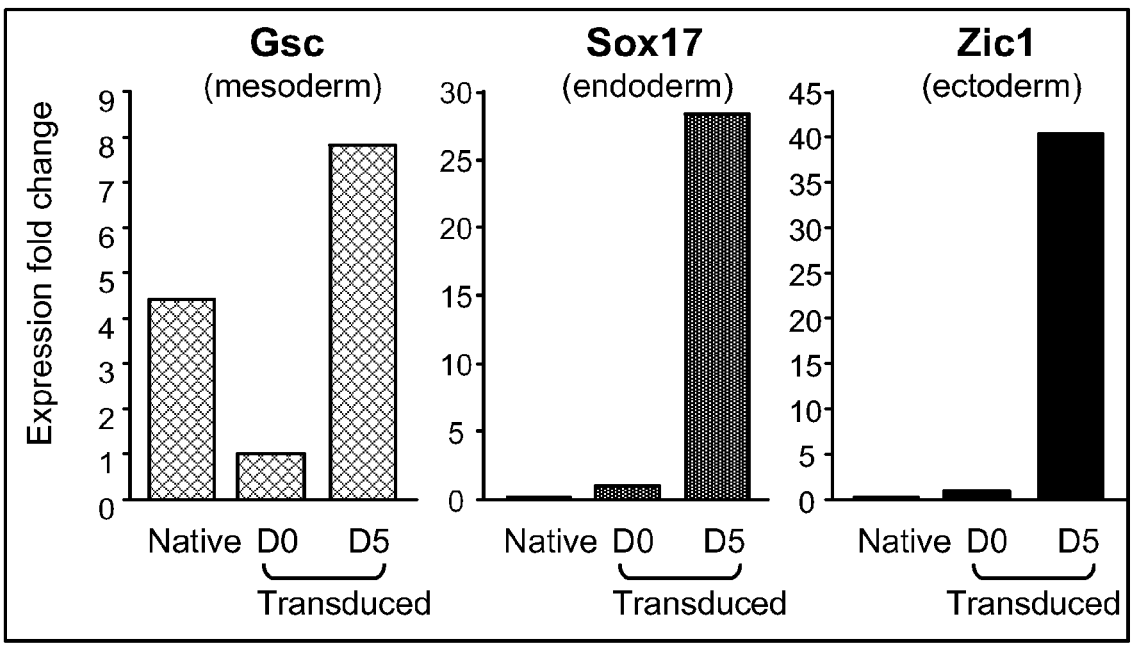

In Vitro Differentiated Transduced Fibroblasts Display a Genetic Pedigree Characteristic of Gastrulating Tissues To identify the diversity of lineage differentiation, gene expression analysis was performed according to protocols established for embryonic stem cells (Behfar et al., *J. Exp. Med.*, 204(2):405-420 (2007); Faustino et al., *Genome Biol.*, 9:R6 (2008); and Nelson et al., *Stem Cells.*, 26(6):1464-1473 (2008)). Parental MEFs provided the baseline for gene expression comparison. Following viral transduction, derived progenitors were differentiated in three-dimensional cultures to allow spontaneous germ layer formation. Sequential differentiation produced EBs at day 5 with dense compaction of cells within a sphere of tissue (FIG. 26A). Gene expression analysis demonstrated a downregulation of pluripotent markers Oct4, Sox2, and Fgf4 by day 5 of differentiation (FIG. 26B). Concomitantly, transduced progenitors gained the expression of mesoderm lineage marker Gsc, endoderm marker Sox17, and ectoderm marker Zic1 after 5 days of differentiation (FIG. 26C). Thus, early lineage marker induction fulfilled in vitro criteria for xenogenic nuclear reprogramming with human stemness-related genes.

In Vivo Lineage Differentiation of Transduced Fibroblasts

Pluripotent cells form spontaneous teratomas following transplantation into immunodeficient mice, an established assay to demonstrate multilineage developmental capacity. Here, immunodeficient mice were subcutaneously injected with native MEFs or transduced counterparts. Only transduced cells gave rise to tumors, following injection at a dose of 500,000 cells, that enlarged to 1 cm in diameter within 4 weeks, in contrast to undetectable growth for native MEFs injected on the contralateral side (FIG. 27A). Tumors derived from transduced MEFs were encapsulated and demonstrated a heterogenous appearance consisting of vascular networks and nonvascularized tissues on gross inspection (FIG. 27B). Tissue histology revealed cellular architecture consisting of mesoderm lineages indicated by muscle (FIG. 27C), ectoderm lineages denoted by keratinized tissues (FIG. 27D), endoderm lineages composed of specialized epithelium (FIG. 27E), and persistence of poorly differentiated cytotypes (FIG. 27F). Together, these data documented the multiple tissues derived from in vivo differentiation and spontaneous formation of complex cytoarchitecture derived from mouse fibroblasts reprogrammed by human sternness-related factors.

Contribution of Transduced Progeny into Ex Utero Blastocysts

A hallmark characteristic of pluripotent stem cells is the ability to incorporate into 8-cell embryos and form morula capable of developing into chimera blastocysts (Wood et al., *Nature*, 365(6441):87-89 (1993)). Primitive stem cell populations engraft within host 8-cell embryos to form mosaic blastocysts, but are universally excluded upon the loss of functional pluripotency Stewart, *J. Embryol. Exp. Morphol.*, 58:289-302 (1980) and Fujii and Martin, *Dev. Biol.*, 74(1): 239-244 (1980)) despite persistent expression of stem cell markers (Nagy et al., *Development*, 110(3):815-821 (1990)). In order to determine the ability of reprogrammed MEFs to incorporate into early-stage morula, the cells were lentivirally labeled with GFP, expanded in vitro, and prepared for diploid aggregation with unlabeled embryos (FIGS. 28A and 28B). GFP-tagged transduced progeny retained the ability to engraft into 8-cell embryos (FIG. 28C) and contribute to chimeric embryos capable of spontaneous formation of blastocysts with appropriate cavitating morphology (FIG. 28D). Diploid aggregation thus provided an efficient ex utero methodology to characterize functional properties of transduced MEFs within a permissive embryonic niche. Specifically, reprogrammed progenitors containing human sternness-related factors revealed the primordial characteristic of pluripotency in embryos with morula integration and blastocyst development, expanding the stringency of pluripotency functional criteria.

High-Fidelity Organogenesis from Transduced Progeny

Figure 29:
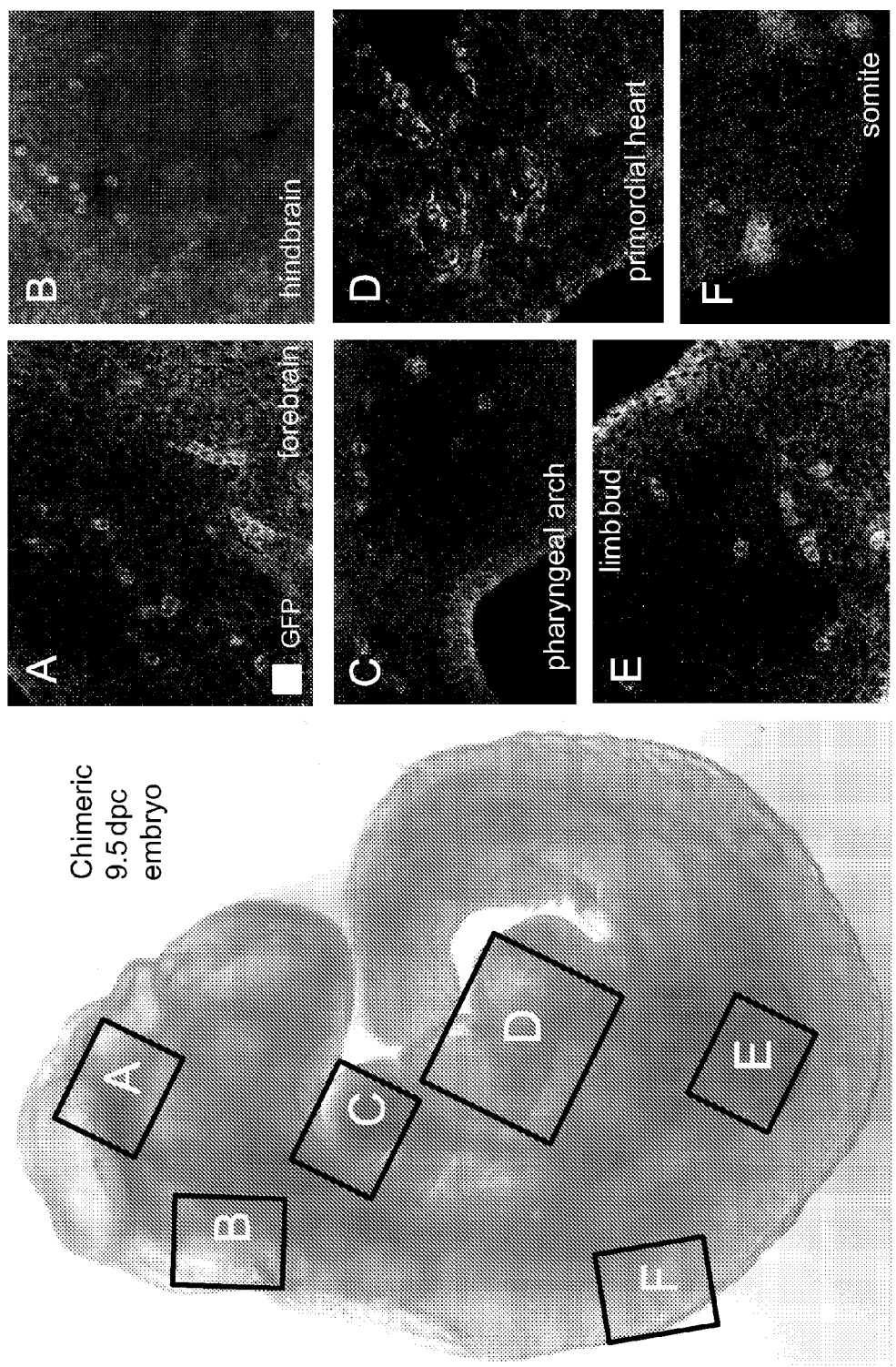
FIG. 29. Organogenesis derived from transduced cells. (A-F) Chimeric embryos were transferred into a surrogate mother for in utero differentiation and were harvested at 9.5 dpc for tissue analysis. Confocal microscopy revealed transduced progeny throughout the embryo including neuronal tissues of the forebrain (A) and hindbrain (B), along with the multilineage phaiyngeal arches that contained endoderm derivatives (C). Mesoderm-derived lineages were present in the heart (D), limb bud (E), and somites (F).

Beyond ex vivo characterization, chimeric embryos establish in situ competency of transduced progeny during natural embryogenesis. Pluripotent stem cells contain the capacity to give rise to all lineages of the developing embryo upon blastocyst integration in a stochastic pattern, depending on the location of blastomere integration during early stage of preimplantation development (Nagy et al., *Development*, 110(3):815-821 (1990)). Mosaic embryos produced by diploid aggregation using GFP-labeled progenitors were transferred to the uterus of a pseudopregnant surrogate for in utero implantation and differentiation. Chimeric embryos were harvested at 9.5 dpc and analyzed for engraftment and differentiation of normative progeny. Embryos that demonstrated normal morphology and appropriate developmental stages of organogenesis were visualized for GFP expression. Transduced progenitors were identified throughout the embryo in multiple developing organs that included central nervous tissue (FIGS. 29A and 29B), pharyngeal arch (FIG. 29C), the heart (FIG. 29D), emerging limb buds (FIG. 29E), and somites (FIG. 29F). Thus, stochastic integration and widespread tissue contribution of reprogrammed cells demonstrated unrestricted differentiation potential and competitive fitness equal to that of native blastomeres, achieving a rigorous criterion to define pluripotency with competent in utero orchestrated organogenesis.

Example 9

Generation of iPS Cells from a Hemophiliac Mouse through Human Factor-mediated Interspecies Reprogramming Induced pluripotent stem (iPS) cells represent the newest platform for gene and cell therapy. HIV-1 vectors carrying human pluripotency genes, OCT3/4, SOX2, KLF4 and c-MYC, were used to reprogram primary human fibroblasts and keratinocytes into iPS cells. The resulting iPS cell clones were positive for human embryonic stem (ES) cell markers (alkaline phosphatase, SSEA4, TRA-1-60, and TRA-1-81) and expressed other pluripotency-related genes, such as hTERT, Nanog, and GDF3. Use of human feeder cells and serum-free media allowed for the generation of xeno-free human iPS cells. To determine whether human sternness-related factors can reprogram mouse somatic cells, murine fibroblast cells were infected with these HIV-1 vectors. Despite the variations in primary amino acid sequences between human and mouse factors, expression of human OCT3/4, SOX2, KLF4, and c-MYC efficiently reprogrammed mouse cells into iPS cells. The resulting iPS cells expressed stem cell markers, differentiated in vitro into all three germ layers according to gastrulation gene expression profiles, and formed in vivo teratoma with multilineage potential. Moreover, the iPS cells were incorporated into a mouse morula to produce blastomeres capable of developing into chimeric embryos with competent organogenesis. The interspecies nuclear reprogramming suggests the evolutionary conserved process of induced pluripotency. This system was applied to generate iPS cells from a factor VIII (FVIII) knockout mouse for hemophilia A gene and cell therapy applications. The tail fibroblast-derived iPS cells exhibited ES-like phenotypes and could be differentiated into beating cardiomyocytes. Since liver sinusoidal endothelial cells produce FVIII in vivo, different in vitro endothelial differentiation protocols using wildtype and FVIII knockout iPS cells can be examined.

Example 10 iPS Programmed without c-MYC Yield Proficient Cardiogenesis for Functional Heart Chimerism Fibroblast Transduction Mouse embryonic fibroblasts (MEF), plated in Dulbecco's modified Eagle's medium with 10% FCS, 1% L-glutamine and penicillin/streptomycin (Invitrogen) at $10^5$ per 24-well plate, were infected for 12 hours with full-length human OCT3/4, SOX2 and KLF4 cDNAs (Open Biosystems) using a lentivirus system. The rationale for using human genes for reprogramming was to determine whether human cDNA is phylogenetically conserved to produce iPS with cardiogenic potential. MEF were maintained in Dulbecco's modified Eagle's medium supplemented with pyruvate (Lonza) and L-glutamine, non-essential amino acids (Mediatech), 2-mercaptoethanol (Sigma-Aldrich), 15% FCS and LIF (Millipore). Within three weeks, iPS clones were isolated and labeled with LacZ and luciferase using pLenti6/UbCN5-GW/LacZ (Invitrogen) and a pSIN-Luc luciferase-expressing vector. Vector integration was PCR confirmed from genomic DNA (Sigma-Aldrich, XNAT2) using primers for OCT4-R AGC-CGCCTTGGGGCACTAGCCC (SEQ ID NO:9), KLF4-R CGCAAGCCGCACCGGCTCCGCC (SEQ ID NO:10), SOX2-R AGCCTCGTCGATGAACG-GCCGC (SEQ ID NO:11), and SFFVprom-F CTCACTCG-GCGCGCCAGTCCTC (SEQ ID NO:12). PCR products were resolved on 1% agarose gel electrophoresis.

Cell Sorting and Electron Microscopy

LacZ labeled clonal populations were trypsinized, incubated with Fluorescein di[β-D-galactopyranoside] (Sigma-Aldrich, F2756), and sorted using a FACS Aria SE flow cytometer (BD Biosciences). On fixation with 1% glutaraldehyde and 4% formaldehyde in 0.1 M phosphate buffered saline (pH 7.2), cells were examined on a Hitachi 4700 field emission scanning microscope. For ultrastructural evaluation, fixed cells were ultramicrotome cut, and stained with lead citrate prior to examination on a JEOL 1200 EXII electron microscope.

Immunostaining and Confocal Microscopy

Cells were stained with anti-SSEA1 antibody (MAB4301; dilution 1:50; Millipore) along with secondary goat anti-mouse IgG Alexa Fluor 568 (Sigma A11031; 1:250) or alkaline phosphatase detection kit (Millipore, SCR004). Immunostaining of derivatives was performed using monoclonal mouse anti-alpha-actinin (Sigma A7811, 1:200), rabbit anti-connexin 43 (Zymed 483000, 1:200), rabbit anti-Mef2c (proteintech 10056-1-AP, 1:50), monoclonal mouse anti-myosin light chain 2a (MLC2a, Synaptic Systems 311011, 1:250), and anti-cardiac troponin I (Abcam 47003, 1:500). Secondary antibodies (Invitrogen) were used at a 1:250 dilution (i.e., goat anti-mouse IgG Alexa Fluor 568, donkey anti-mouse IgG Alexa Fluor 488, and goat anti-rabbit IgG Alexa Fluor 488). Nuclei were labeled with 4,6'-diamidino-2-phenylindole (DAPI; Invitrogen). Images were taken using laser confocal microscopy (Zeiss LSM 510 Axiovert). For LacZ staining, samples were fixed with 0.25% gluteraldehyde for 15 minutes at room temperature prior to 13-galactosidase staining In Vivo and In Vitro Differentiation Transduced fibroblasts were injected subcutaneously into the flank skin of anesthetized athymic nude mice or immunocompetent C57BL/6 strain of mice at 500,000/50 µL medium. Local growth was monitored daily until tissue was harvested and processed by rapid freezing and cryosectioned for hematoxylin/eosin procedures. Separately, iPS were differentiated into three-layer embryoid bodies (EB) using the hanging-drop method. Digital serial images were analyzed with Metamorph (Visitron Universal Imaging).

Gene Expression

Expression of pluripotent, gastrulation, and cardiac markers was detected by RT-PCR. Mouse Gapdh (4352932E; Applied Biosystems) was used as control. Analyzed genes included Sox2 (Mm00488369_s1), Oct4 (Mm00658129_gH), Fgf4 (Mm00438917_m1), Gsc (Mm00650681_g1), Sox17 (Mm00488363_m1), Mesp2 (Mm00655937_m1), Tbx5 (Mm00803521_m1), Nkx2.5 (Mm00657783_m1), and Mef2c (Mm01340839_m1; Applied Biosystems).

Patch Clamp and Calcium Imaging

Derived cardiomyocytes, enriched by dual interface Percoll gradient (Invitrogen) (Hodgson et al., Am. J. Physiol. Heart Circ. Physiol., 287:H471-479 (2004)), were plated on laminin coated coverglass for >24 hours. Membrane electrical activity was determined by patch-clamp recording in the whole cell configuration using current- or voltage-clamp mode (Axopatch 1C, Axon Instruments). Action potential profiles and voltage-current relations were acquired and analyzed with the Bioquest software. Cells were superfused with Tyrode solution containing (in mM) 137 NaCl, 5.4 KCl, 2 CaCl$_2$, 1 MgCl$_2$, 10 HEPES, and 10 glucose (with pH adjusted to 7.3 with NaOH) or calcium-free Tyrode in which CaCl$_2$ was replaced by EGTA 5 mM. Patch pipettes (5-10 MΩ) containing (in mM) 140 KCl, 1 MgCl$_2$, 10 HEPES, 5 EGTA, and supplemented with 5 mM ATP (with pH adjusted to 7.3 with KOH) were used for electrophysiological measurements performed at 34±1° C. set by a Peltier thermocouple temperature controller. To assess intracellular Ca$^{2+}$ dynamics, cells were loaded with the Ca$^{2+}$-fluorescent probe Fluo 4-AM (Invitrogen), imaged with a Zeiss LSM live 5 laser confocal microscope, and analyzed using LSM software.

Chimeric Blastocyst Formation and In Utero Organogenesis

CD1 embryos were harvested at 2.5 days post coitum (dpc) and plated as pairs in microwells for diploid aggregation. LacZ-labelled cells cultured for at least two passages after thawing were partially digested using trypsin 0.25%-EDTA and pre-plated for 45 minutes to allow attachment of feeders. Floating clumps (8-15 cells) were co-incubated with embryo pairs in microwells. The aggregation complex was incubated for 24 hours until cavitation of blastocysts. Surrogate mothers were anesthetized (2-3% inhaled isoflurane), uterus dissected through a minimal flank incision, and blastocyst-stage chimeric aggregates transferred into the uterus. Pseudopregnant females supported pregnancy until days 8.0-9.5 dpc, when embryos were harvested and analyzed for LacZ-labelled progenitors using a ProgRes C3 camera-equipped Zeiss stereo Discovery V20 microscope. Embryos were fixed with 0.25% gluteraldehyde for 15 minutes at room temperature prior to 13-galactosidase staining Molecular Imaging Luciferase-transfected iPS were cultured for multiple passages including a freeze/thaw cycle prior to expansion and transplantation into recipients. Cells were tracked with the IVIS 200 Bioluminescence Imaging System (Xenogen) following intra-peritoneal injection of 150 mg/kg D-luciferin (Xenogen), and signals analyzed with the Living Image Software (Xenogen).

Electrocardiography and Echocardiography

In age-matched control and iPS-chimera mice under anesthesia (1.5% isoflurane), heart rate and rhythm were measured using 4-limb lead electrocardiography (MP150, Biopac). Cardiac structure and left ventricular contractility were quantified by trans-thoracic echocardiography using a 30 MHz MS400 transducer (Vevo2100, Visual Sonics).

Statistics

Data were presented as mean±SEM. Student's t test was used to evaluate significance of PCR data. Wilcoxon test was used to evaluate physiological parameters between chimeric and non-chimeric cohorts. A p value<0.05 was predetermined.

Results

Figure 30A:
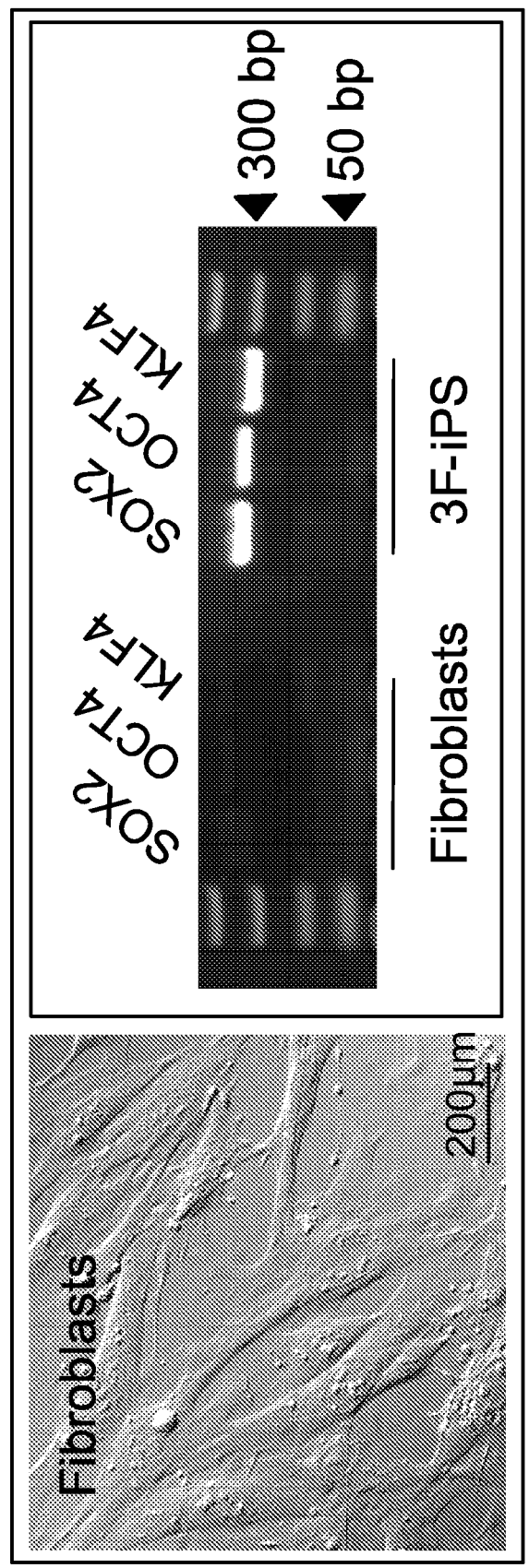
FIG. 30. Bioengineered pluripotency in the absence of c-MYC transgene. A, Mouse embryonic fibroblasts (left) were transduced with three HIV-derived lentiviruses containing human genes SOX2, OCT4, and KLF4. Genomic integration of viral constructs was detected in transduced progeny, but not in parental fibroblast (right). B, Within three weeks, expression of the gene triad (3F) induced a dramatic change from flat fusiform fibroblasts to a round and compact embryonic-stem-cell-like morphology (left) with reduced cytoplasm (right). C, Reprogrammed cells acquired pluripotency markers alkaline phosphatase (AP; left) and SSEA-1 (right), absent from parental fibroblasts (inset).
Figure 30B:
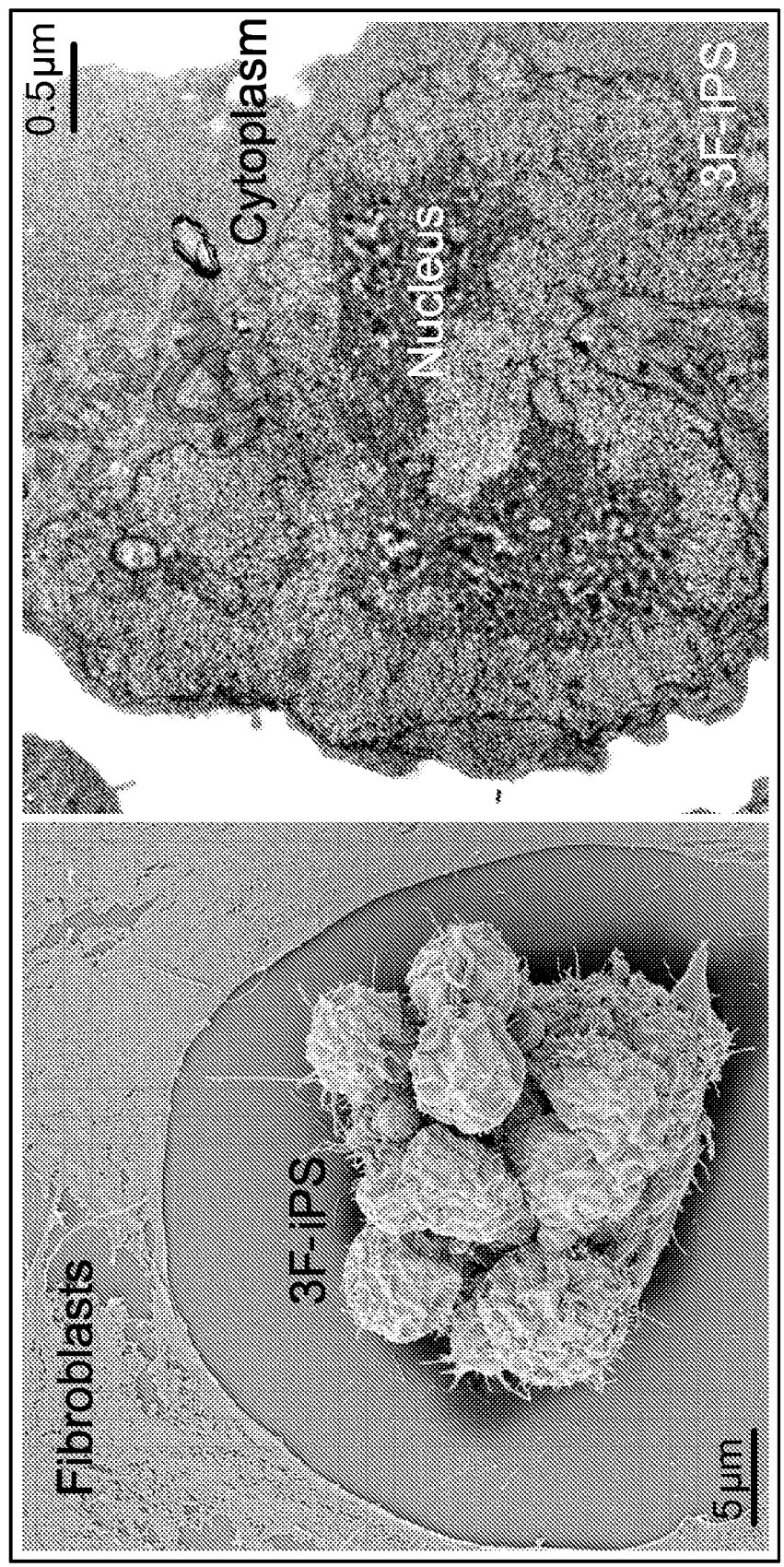
Figure 30C:
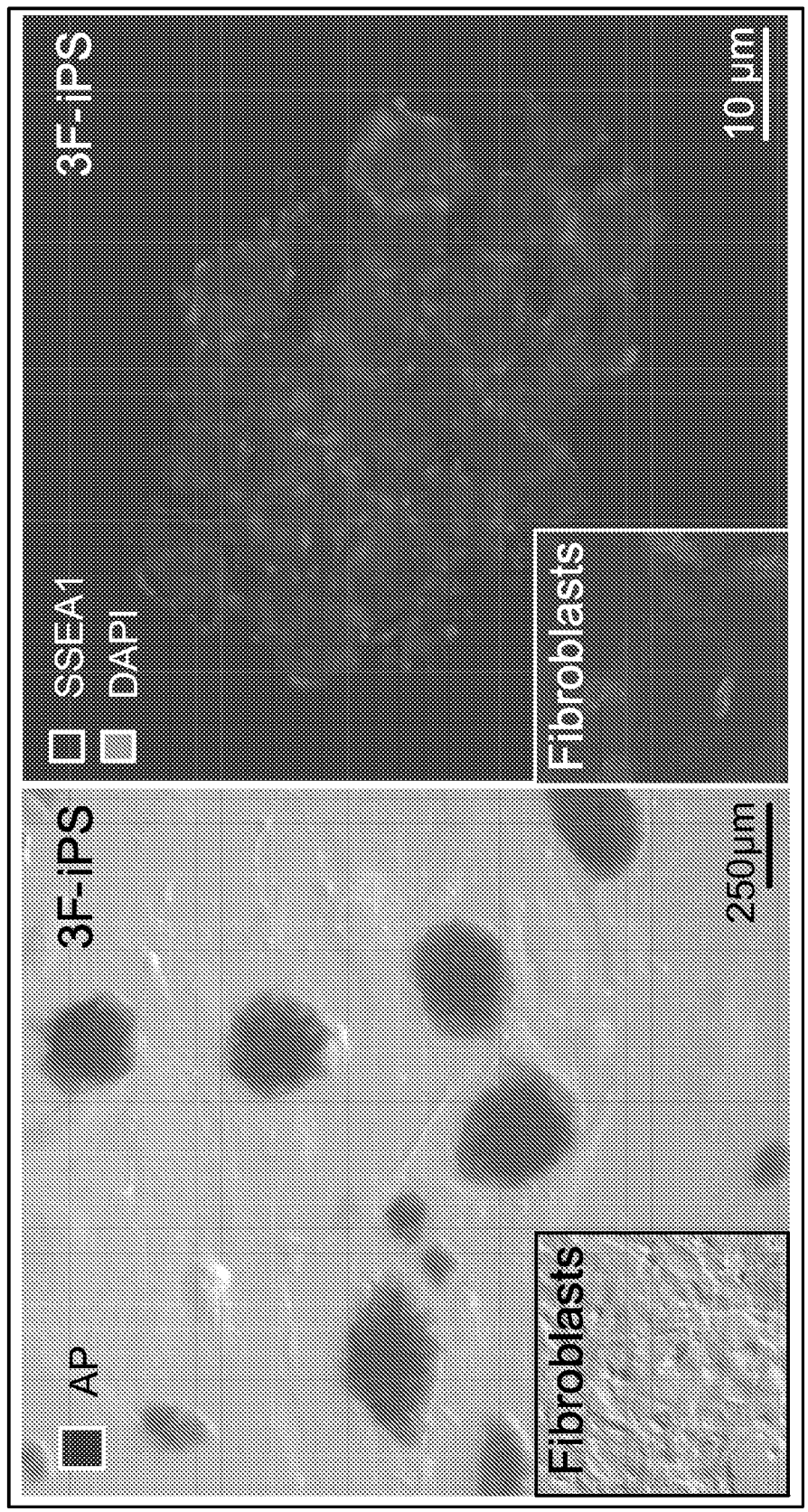

Phylogenetically Conserved Nuclear Reprogramming with Human Stemness Factor Independent of c-MYC MEFs grown in monolayers demonstrated contact inhibition upon culture confluency. Elongated flat cells typical of fibroblasts provided a homogenous population of starting somatic tissue (FIG. 30A). Upon cross-species transduction with three human stemness-related factors, SOX2, OCT4, and KLF4 vector-derived transgenes were stably integrated in engineered progeny, absent from the untransduced parental source (FIG. 30A). Scanning electron microscopy documented structural metamorphosis, revealing isolated colonies that exhibited a condensed morphology in contrast to the flat untransduced neighboring fibroblasts (FIG. 30B, left side). Transmission electron microscopy imaged a reduced cytosol-to-nuclear ratio in transduced progeny, indicating acquisition of primitive cell phenotype (FIG. 30B, right side). Tightly packed colonies, which represent clonal clusters of reprogrammed cells, robustly expressed markers of pluripotency, alkaline phosphatase (AP; left side) and SSEA-1 (right side), negligible in parental fibroblasts (FIG. 30C). To validate acquired pluripotency in vivo, cells transduced with three human stemness factors (3F-iPS) were injected subcutaneously into immunodeficient mice. Within weeks following delivery of 500,000 3F-iPS, three germ layers were detected on histology, including glandular epithelium (endoderm), keratinized epidermal ectoderm (ectoderm), and mesenchymal derived connective tissue (mesoderm; FIG. 31A). Molecular analysis identified cardiac tissue that demonstrated sarcomeric striations (FIG. 31B, left), and typical markers such as alpha-actinin (FIG. 31B, middle), cardiac troponin I and sarcolemmal connexin 43 (FIG. 31B, right). Thus, human transcription factors SOX2, OCT4, and KLF4, in the absence of c-MYC, induced phylogenetic nuclear reprogramming from murine fibroblasts to achieve functional pluripotency across species.

Figure 32A:
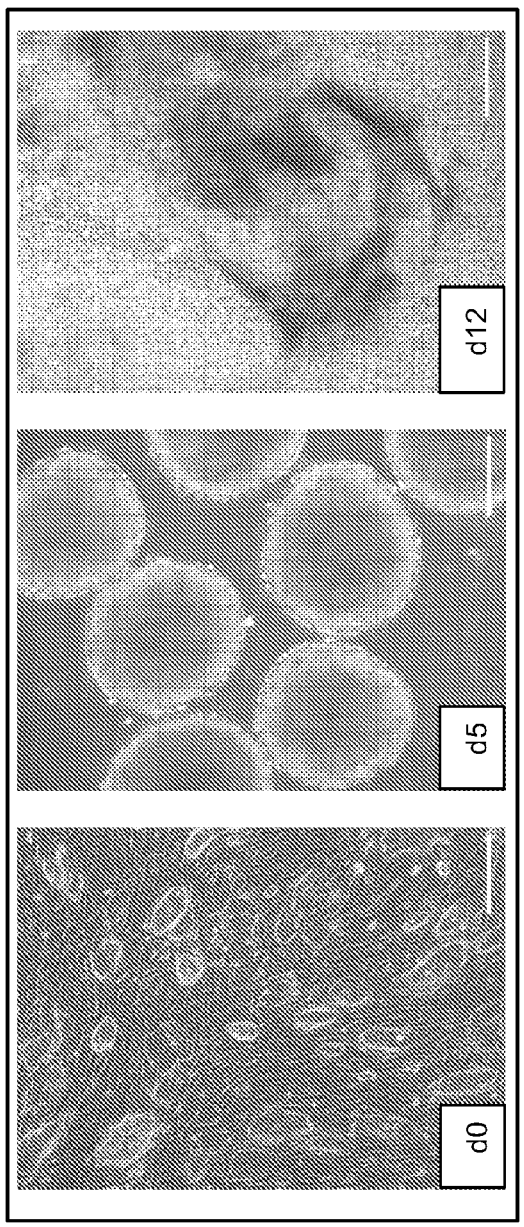
FIG. 32. Kinetics of in vitro lineage derivation from iPS. 3F-iPS were differentiated using the hanging drop method followed by expansion of progeny on gelatinized plates. A, Cells were sampled from undifferentiated cultures at day 0 (top), floating embryoid bodies at day 5 (middle), and differentiating cultures at day 12 (bottom) for gene expression analysis. B, Pluripotency genes Sox2, Oct4, and Fgf4 immediately downregulated with initiation of differentiation. C, Gastrulation markers peaked at day 5, coinciding with three germ layer formation in embryoid bodies. D, Upregulation of cardiac transcription factors Tbx5, Nkx2.5, and Mef2c was observed at day 12 indicating that 3F-iPS are able to produce cardiac progenitors. *$p<0.05$.
Figure 32B:
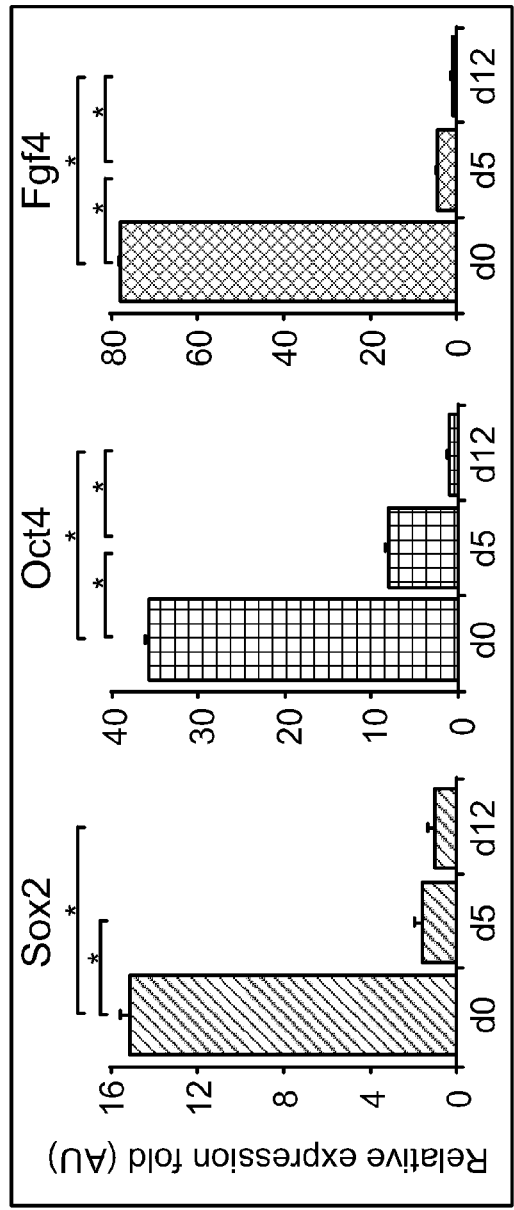
Figure 32C:
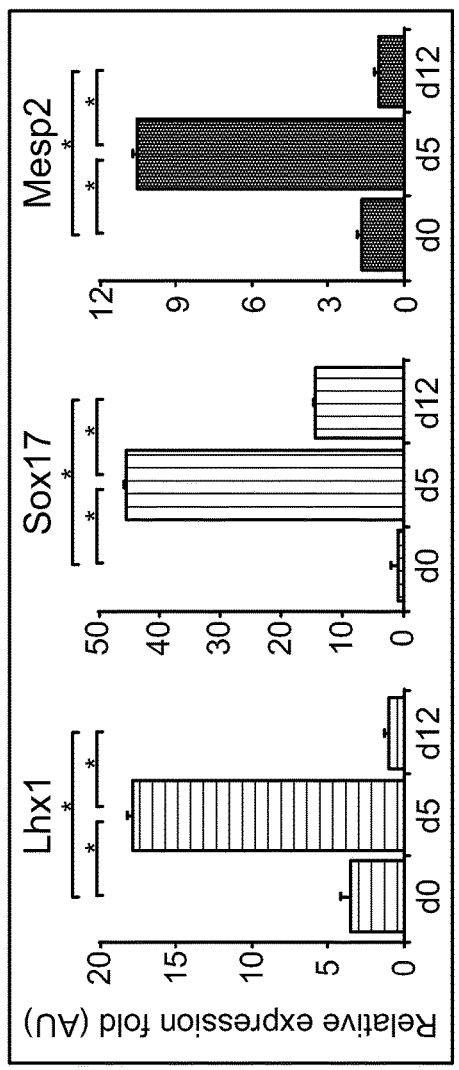
Figure 32D:
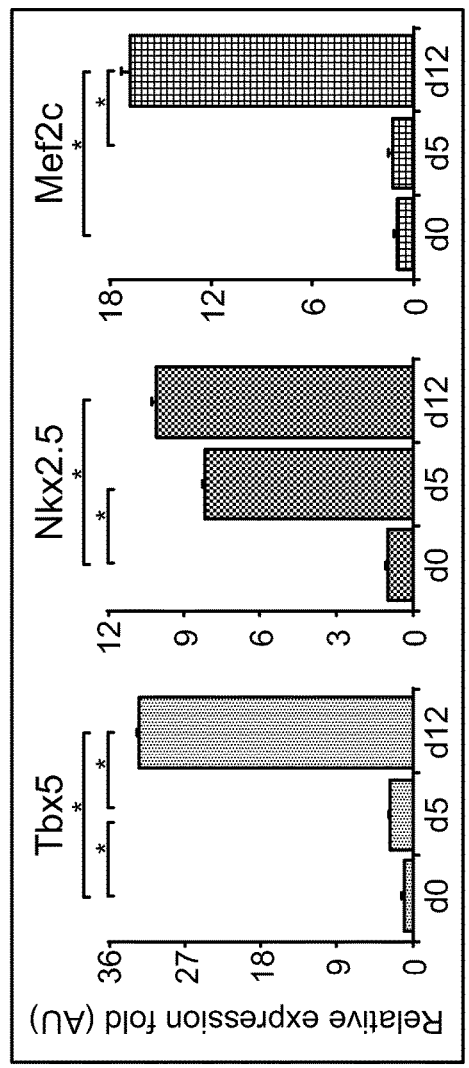

Three Factor iPS-derived Embryoid Bodies Unmask Reproducible Cardiogenic Potential Distinct 3F-iPS clones consistently yielded clusters of undifferentiated cells capable of generating embryoid spheroids at day 5 following a hanging-drop protocol, and differentiated in three-dimensional cultures throughout a 12-day period (FIG. 32A). iPS progeny were sampled sequentially starting at day 0 monolayers (FIG. 32A, top), day 5 floating embryoid spheres (FIG. 32A, middle), and day 12 plated embryoid bodies (FIG. 32A, bottom). Gene expression analysis from two independent clones, sampled throughout the continuum of differentiation, demonstrated immediate, sustained, and reproducible downregulation of pluripotent markers Oct4, Sox2, and Fgf4 (FIG. 32B; $p<0.05$). Recapitulating gastrulation in the embryo, induction of mesoderm (Goosecoid, Gsc) and endoderm (Sox17) peaked by day 5 in iPS-derived embryoid bodies, giving rise to the pre-cardiac mesoderm identified by Mesp2 expression (FIG. 32C; $p<0.05$). Cardiac differentiation was further indicated by a 20-30 fold upregulation in cardiac transcription factors Tbx5, Nkx2.5, and Mef2c by day 12, compared to undifferentiated day 0 iPS (FIG. 32D; $p<0.05$). Thus, the pattern of gene expression in 3F-iPS, verified across all tested clones, revealed exchange of genes with pluripotent potential for the acquired proficiency of lineage specification, ensuring reproducible cardiogenic outcome.

Figure 33A:
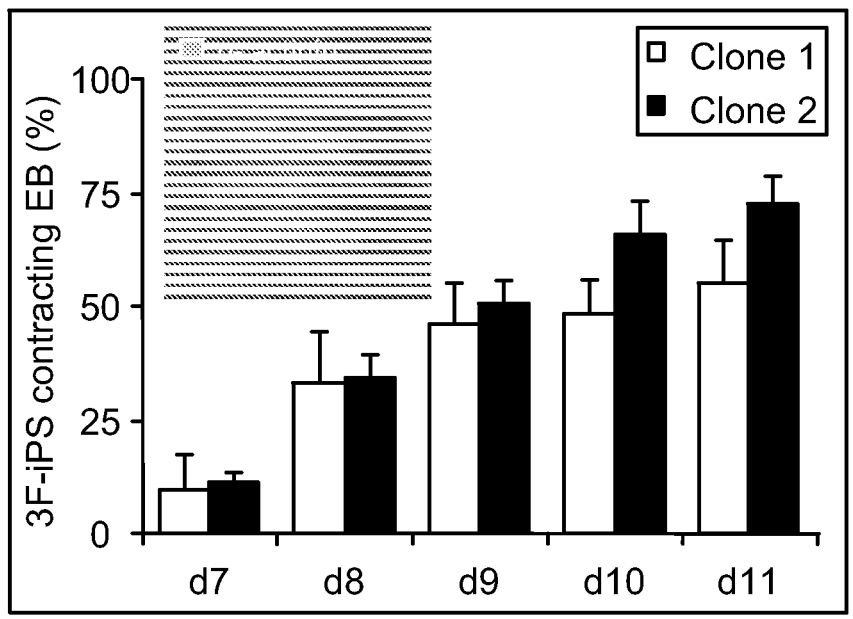
FIG. 33. Functional cardiogenesis derived from 3F-iPS. A, Derived from two independently isolated clones, embryoid bodies (EB) increasingly demonstrated beating areas between day 7 and 11 of differentiation. The presence of area actively contracting coincided with positive immunostaining for cardiac protein α-actinin (inset, bar 10 μm). B, Synchronized contractile activity (rectangles; top) was detected within adjacent EB (bottom). C, Electron microscopy of 3F-iPS derived cardiomyocytes (CM) revealed morphological changes from compacted colonies to rod-shaped cardiomyocyte-like cells (top). High density contractile proteins were found in organizing sarcomeres (middle) as well as gap junction structures between adjacent cells (bottom). D, Immunostaining demonstrated presence of contractile protein alpha actinin in combination with cardiac transcription factor Mef2c (top), and gap junction-protein connexin 43 (bottom). E, Action potentials were recorded in beating cells using patch clamp in the current clamp mode. DAPI: 4,6'-diamidino-2-phenylindole.
Figure 33B:
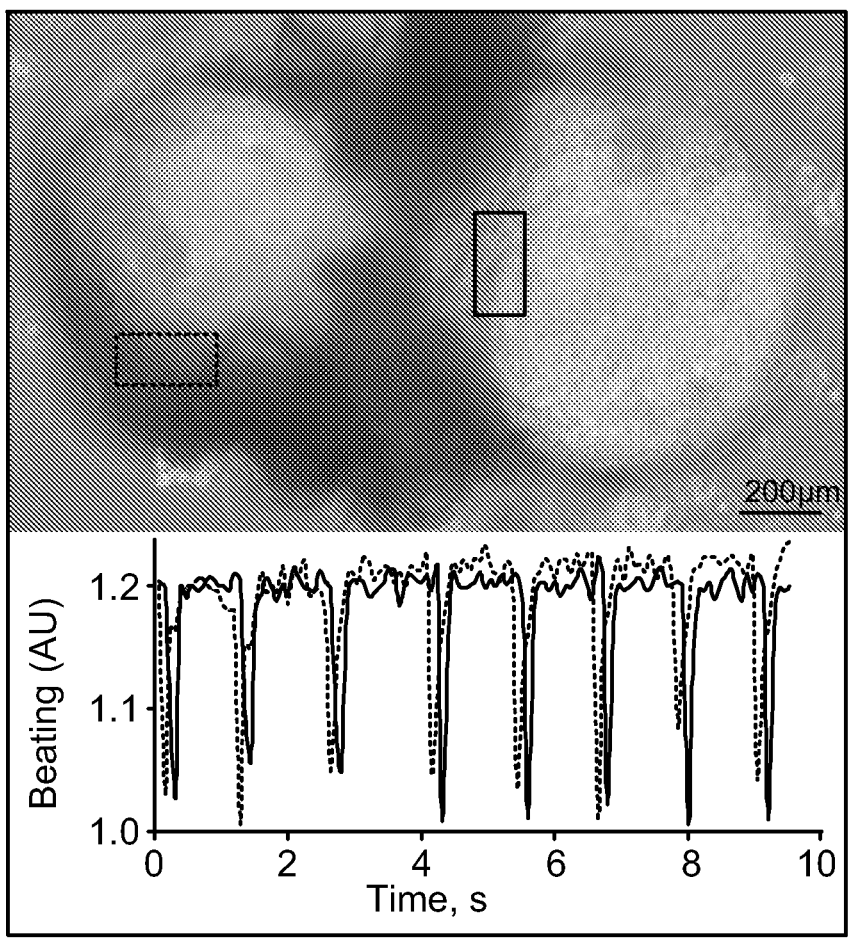
Figure 33E:
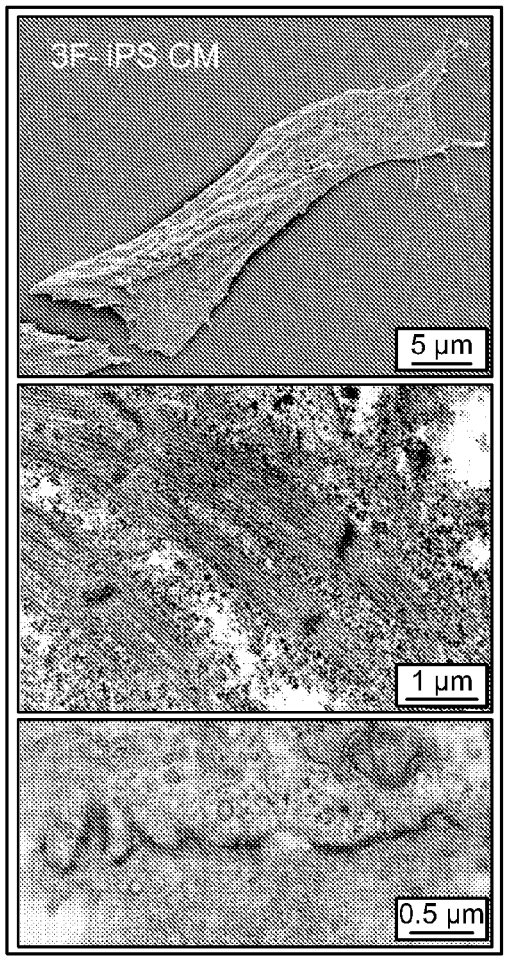
Figure 33E:
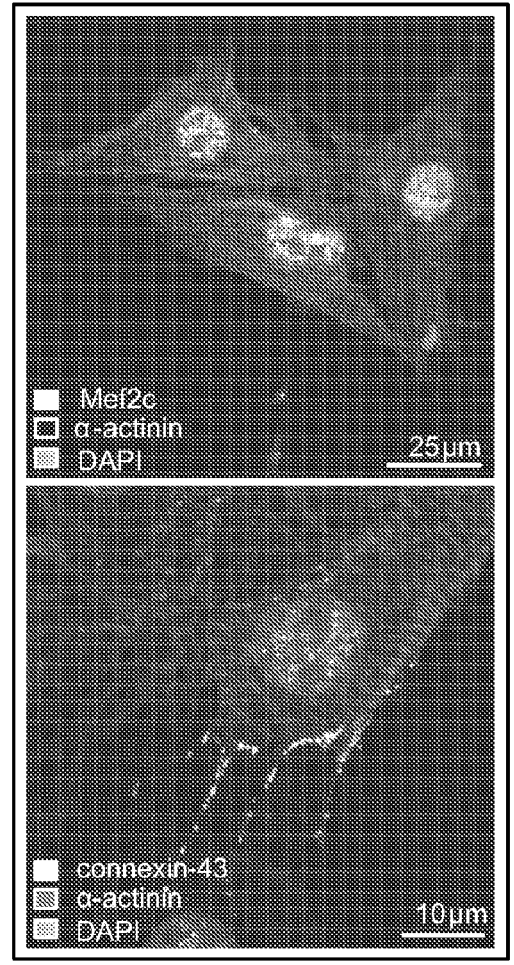
Figure 33E:
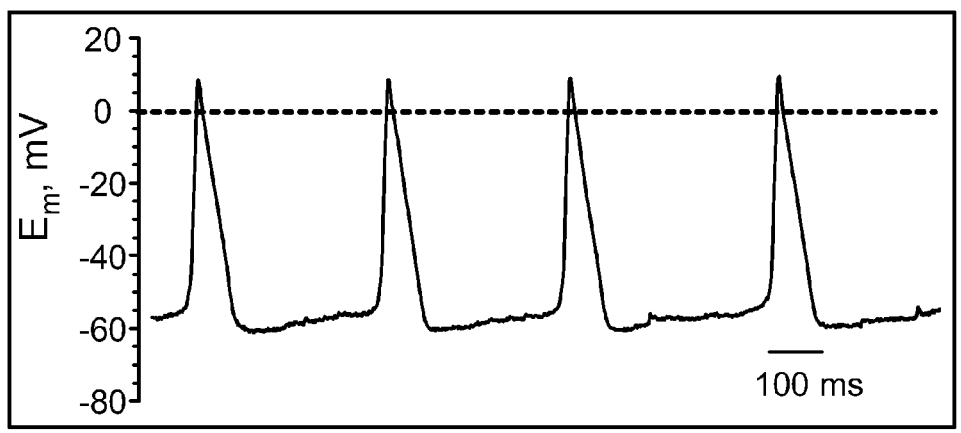

Functional Cardiogenesis Derived from 3F-iPS iPS differentiating within embryoid bodies (EB) were examined daily to quantify the percentage of EB that acquired cardiac phenotype tracked by spontaneous beating activity. Independent clones derived by three-factor reprogramming revealed consistent progression of beating activity as early as seven days following progeny differentiation (FIG. 33A) that corresponded to expression of cardiac contractile proteins (FIG. 33A, inset). From ~10% of contracting EB within independent clones starting two days after plating EB at day 5, the percentage of beating areas progressively increased through day 11 with 54-72% of all colonies containing at least one area of spontaneous contractions (FIG. 33A). Notably, EB that demonstrated multiple beating areas (FIG. 33B top, rectangles) developed synchronized contractile rhythm underlying coordinated electrical activity that propagated through the syncytium of nascent cardiac tissue (FIG. 33B bottom). Isolation of cardiomyocytes from beating EB was achieved using a selective density gradient. Structural changes consistent with cardiac differentiation were observed at day 12 as 3F-iPS progeny developed rod-shaped morphology (FIG. 33C, top), a mature myofibrillar organization (FIG. 33C, middle), and gap junctions that bridged adjacent progeny (FIG. 33C, bottom). Similarly, iPS-derived cells demonstrated presence of the cardiac transcription factor Mef2c, contractile protein alpha actinin, and gap junction-protein connexin 43 (FIG. 33D). Moreover, spontaneous action potential activity was recorded in isolated cells under whole cell current-clamp mode (FIG. 33E).

Figure 34A:
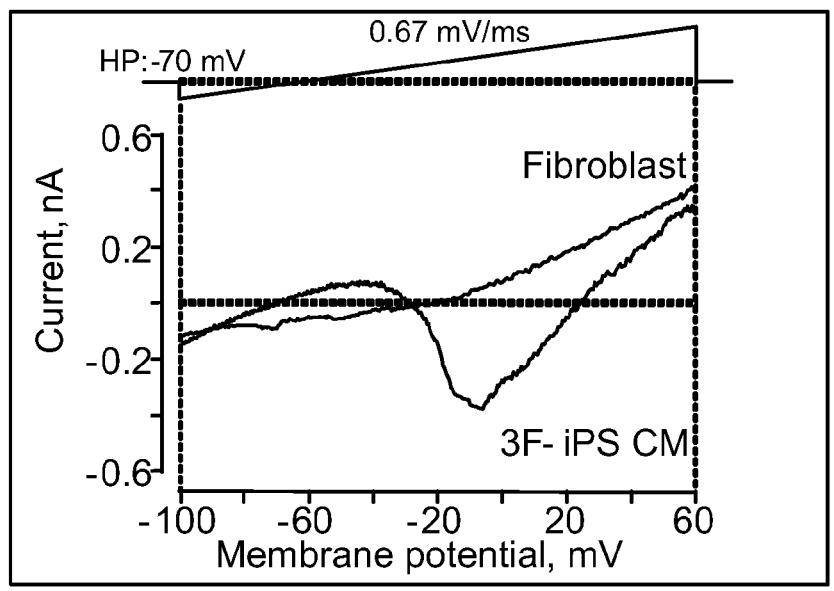
FIG. 34. Calcium-dependent excitation-contraction coupling in 3F-iPS-derived cardiomyocytes. A, An inward current was detected in iPS-derived cardiomyocytes (3F-iPS CM) absent from parental fibroblasts (Fibroblast). B, Reversal of extracellular calcium suppressed inward current. C, Spontaneous action potentials were reversibly arrested in zero calcium milieu. D, Fluo-4AM labeled iPS-derived cells demonstrated fluorescent dynamics consistent with calcium transients. E, Rhythmic calcium transients coincided with cell contractions.
Figure 34B:
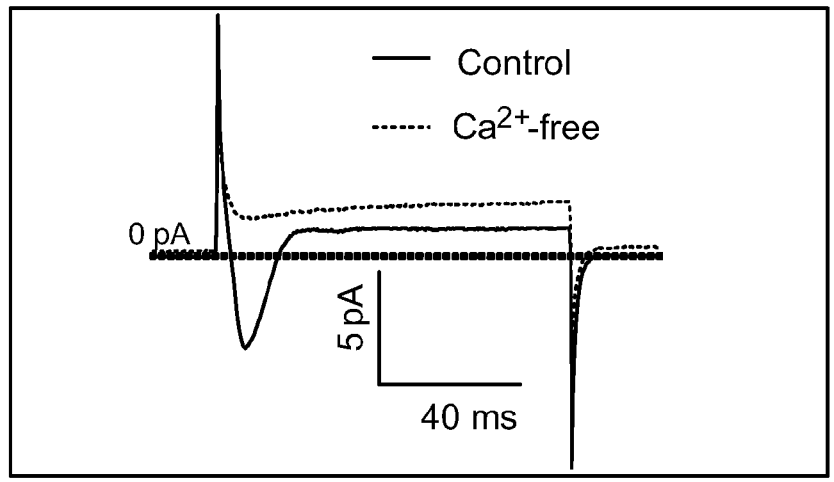
Figure 34C:
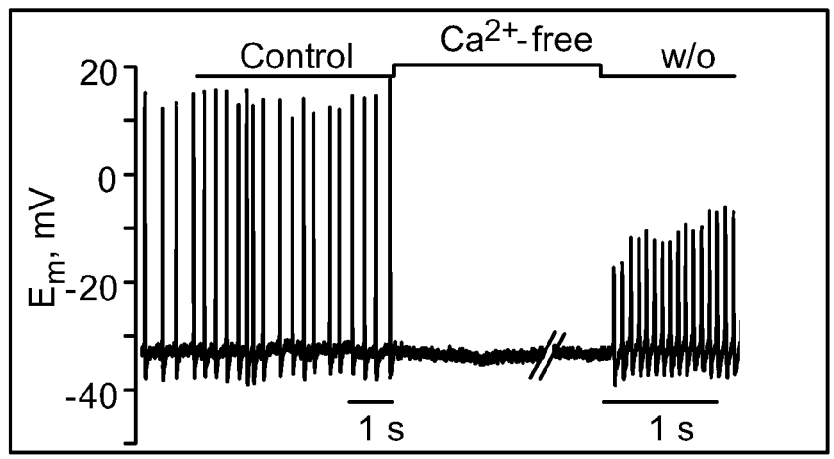

Under voltage-clamp, depolarization of 3F-iPS progeny by membrane potentials imposed ramp pulses from −100 to +60 mV revealed prominent inward and outward current components, not present in non-excitable parental fibroblasts (FIG. 34A). The inward current component was eliminated in the absence of external $Ca^{2+}$ (FIG. 34B). Furthermore, removal of $Ca^{2+}$ reversibly abolished action potential activity in 3F-iPS derived cardiac cells (FIG. 34C). Loaded with the calcium selective Fluoro-4AM probe, 3F-iPS derived cardiomyocytes demonstrated rhythmic transients consistent with calcium dynamics in diastole versus systole (FIG. 34D), in synchrony with force-generating mechanical contractions (FIG. 34E). These data indicated reproducible derivation of 3F-iPS progeny that progressively acquired authentic cardiogenic machinery required for excitation-contraction coupling, and generation of functional cardiomyocytes.

Figure 35A:
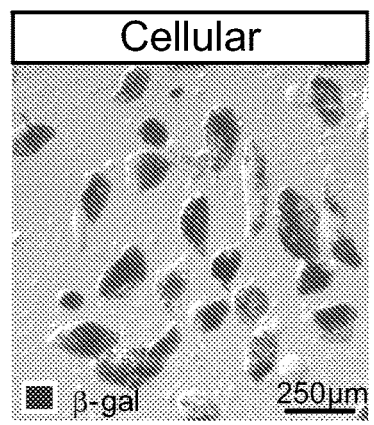
FIGS. 35A-35J. iPS bioengineered cardiac chimerism contributes to sustained heart function throughout development and lifespan. (A-B) LacZ labeled-iPS coincubated with diploid embryos. (C-D) Chimeras revealed the ability of 3F-iPS to integrate into host morulae. (E-G) Presence of iPS was sustained throughout embryonic development as shown for 8.0 through 9.5 dpc contributing to cardiac inflow and outflow tracts (G, inset). H, Other than mosaic coat color, adult chimeras were physically indistinguishable from non-chimeric littermates. I, Increasing levels of chimeric expressed luciferase distributed within tissues were detected according to molecular imaging with iPS-derived progeny. J, Cardiac electrocardiography was equivalent between non-chimera and chimera. K, Cardiac echocardiography demonstrated normal structure of heart, valves, and great-vessels with equivalent systolic and diastolic function between non-chimera and chimera. Ao: aorta, LV: left ventricle; LVDd: left ventricular diastolic diameter, LVDs: left ventricular systolic diameter, RV: right ventricle. bar 2 mm.
Figure 35E:
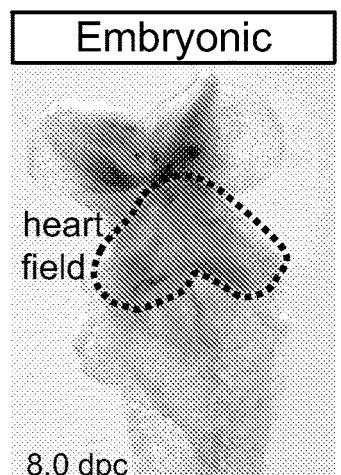
Figure 35B:
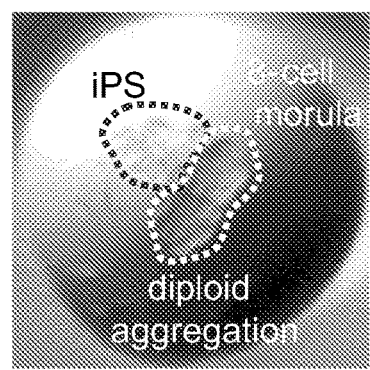
Figure 35F:
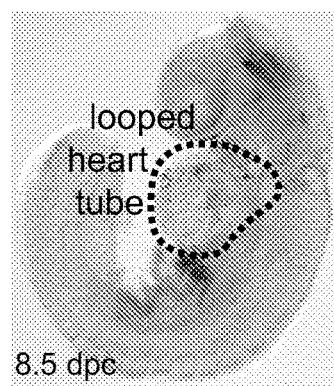
Figure 35C:
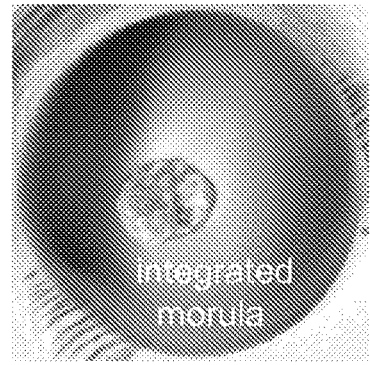
Figure 35D:
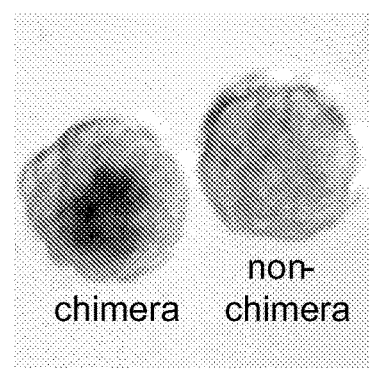
Figure 35G:
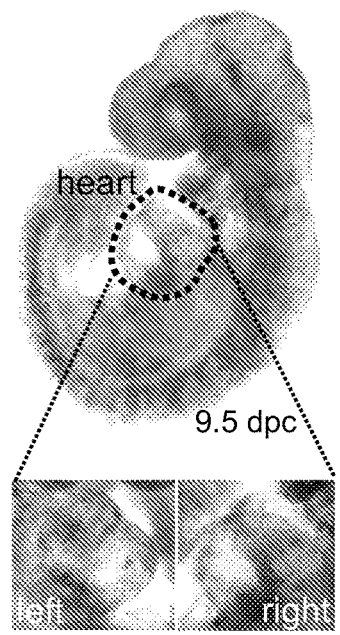
Figure 35H:
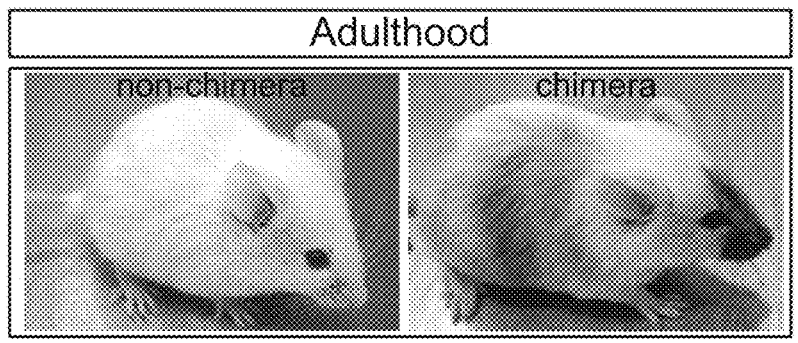
Figure 35I:
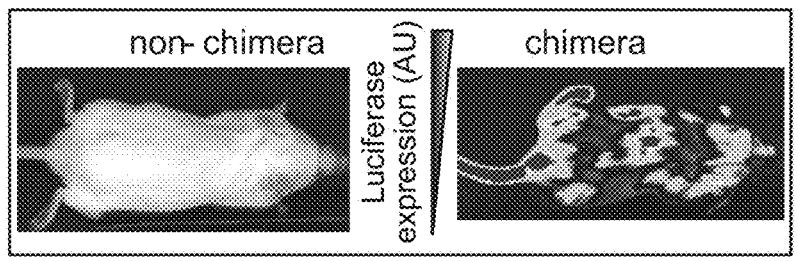
Figure 35J:
Figure 35K:
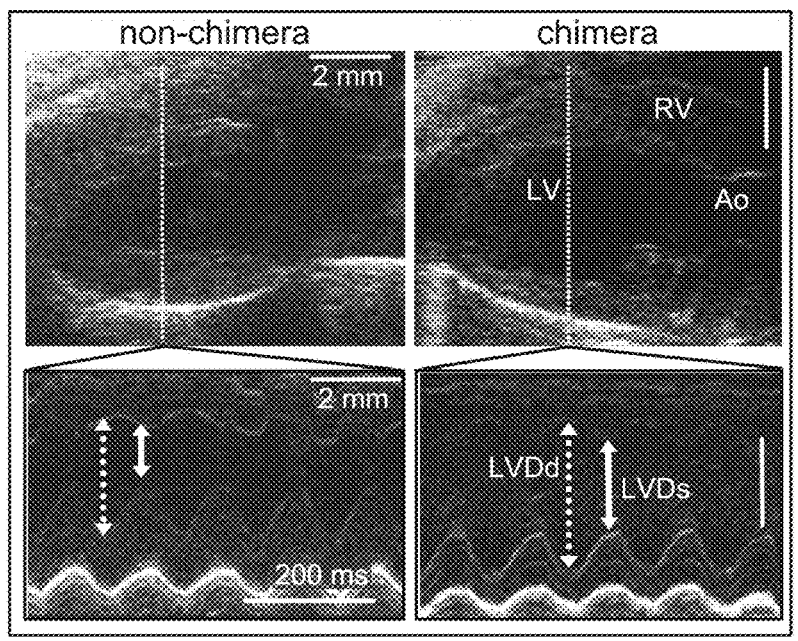

3F-iPS Chimerism Contributes to De Novo Heart Tissue Formation in the Embryo and Sustains Cardiac Function in the Adult Heart Non-coerced diploid aggregation at the morula stage allows competent pluripotent stem cells to assimilate within a developing embryo and contribute to chimeric organogenesis. 3F-iPS labeled with LacZ and luciferase expression cassettes were clonally expanded and allowed aggregation with two, 8-cell morula embryos (FIGS. 35A and 35B). The process of diploid aggregation, that engages equivalent progenitors into a chimeric blastocyst, exploited the ability of 3F-iPS to integrate into host embryos and function as a blastomere, demonstrated by mosaic distribution of positive lacZ-expressing iPS progeny (FIGS. 35C and 35D). iPS-derived tissue populated the embryo (n=7) during development and contributed to all stages of cardiogenesis from primitive heart fields to looped heart tubes corresponding to 8.0 to 9.5 dpc, respectively (FIGS. 35E-6G). By 9.5 dpc when the heart tube has fully looped to form distinct inflow and outflow tracts, iPS progeny was detected throughout nascent heart parenchyma (FIG. 35G, inset). Live born 3F-iPS demonstrated iPS contribution and engraftment throughout adult tissues with dark coat color visible on the white background (n=5; FIG. 35H). Transgenic luciferase expression emanating from labeled iPS progeny upon in vivo imaging ranged from undetectable levels to a high degree of achieved chimerism. Chimeric offspring (n=5), including those with the highest contribution of iPS progeny (FIG. 35I), demonstrated tumor-free assimilation throughout the three months of follow-up. This profile was independently verified by lack of tumor formation during 7.5 months of prospective follow-up upon subcutaneous injection of 500,000 3F-iPS into the flank of immunocompent hosts (n=6). In line with non-disruptive integration, iPS chimera (n=5) exhibited vital signs, including average body weight, core temperature, heart and respiratory rates, that were indistinguishable from non-chimera counterparts (n=5; Table 3). Based on continuous electrocardiography, the chimeric cohort was devoid of ectopy, arrhythmias, or conduction blocks (FIG. 35J). Comprehensive echocardiography analysis further demonstrated consistent cardiac structure between 3F-iPS chimera and non-chimera cohorts with similar measured values for aortic, pulmonary, and right outflow tract diameters, along with equivalent left atrium and left ventricular volumes (Table 3). Synchronized four-chamber function throughout systolic and diastolic cardiac cycles, indicating functional integration of 3F-iPS progeny into the adult organ, was also equivalent to non-chimera counterparts (n=5, FIG. 35K and Table 3). Left ventricular functional performance of all 3F-iPS chimeras was essentially identical, according to measured fractional shortening and ejection fraction, compared to age and sex-matched normal controls (Table 3). Together, this evidence indicates a high proficiency for 3F-iPS progeny to contribute to normal heart formation, and sustain chimeric tissue without disruption to myocardial structure or function throughout prenatal to postnatal development.

TABLE 3

Cardiovascular comparison between non-chimera and 3F-iPS chimeric cohorts.

|  | Non-chimera | Chimera | p |
|---|---|---|---|
| Cohort, n | 5 | 5 | |
| Vital signs | | | |
| Body weight, g | 33.8 ± 1.0 | 36.2 ± 2.1 | 0.25 |
| Body core temperature, ° C. | 35.2 ± 0.8 | 35.8 ± 0.6 | 0.46 |
| Respiration rate, /min | 117 ± 3 | 112 ± 2 | 0.34 |
| Heart rate, beats/min | 469 ± 10 | 455 ± 9 | 0.29 |
| Cardiovascular structure | | | |
| Ascending aorta, mm | 1.68 ± 1.09 | 1.58 ± 0.04 | 0.35 |
| Main pulmonary artery, mm | 1.80 ± 0.14 | 1.81 ± 0.14 | 0.75 |
| Right ventricular outflow tract, mm | 1.32 ± 0.18 | 1.31 ± 0.19 | 0.99 |
| Left atrium, mm | 1.79 ± 0.13 | 2.04 ± 0.19 | 0.35 |
| LVDd/BW, mm/g | 0.106 ± 0.01 | 0.113 ± 0.01 | 0.60 |
| Left ventricular end-diastolic volume, µL | 59.2 ± 3.3 | 61.5 ± 6.3 | 0.92 |
| Left wall thickness (septum plus posterior wall), mm | 1.43 ± 0.05 | 1.56 ± 0.08 | 0.25 |
| Left ventricle/body weight, mg/g | 2.52 ± 0.24 | 3.22 ± 0.30 | 0.12 |
| Cardiac function | | | |
| Fractional shortening, % | 46.6 ± 2.8 | 45.4 ± 3.1 | 0.75 |
| Ejection fraction, % | 61.7 ± 3.9 | 63.6 ± 1.8 | 0.92 |

LVDd, left ventricular diastolic diameter.
BW, body weight.

Figure 36:
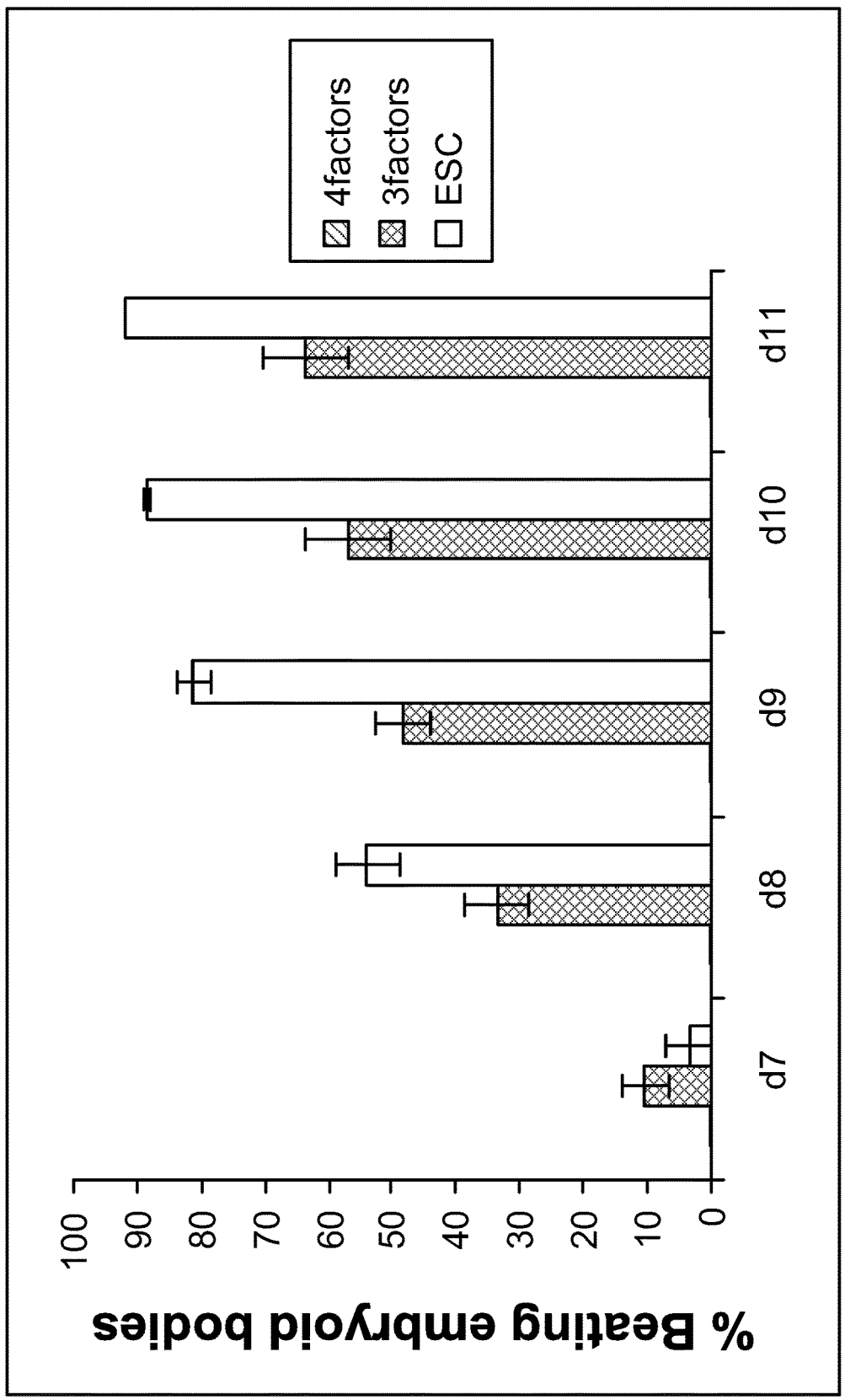
FIG. 36 is a bar graph plotting the percent of beating embryoid bodies observed in iPS reprogrammed with four factors (n=2), iPS reprogrammed with three factors (n=2), or embryonic stem cell line (ESC) during day 7 to 11 of differentiation.

In one experiment, the beating activity observed in iPS reprogrammed with four factors (SOX2, OCT4, KLF4, and cMYC; n=2) was compared to the beating activity observed in iPS reprogrammed with three factors (SOX2, OCT4, and KLF4; n=2) and in an embryonic stem cell line (ESC) during day 7 to 11 of differentiation. The three factor iPS exhibited a similar trend as reference ESC (FIG. 36). No beating activity was observed in four factor iPS during the differentiation period.

In summary, these results demonstrate that transgenic expression of three human sternness factors, SOX2, OCT4, and KLF4, can reset fibroblasts (e.g., murine fibroblasts) to the pluripotent ground state. Transduction without c-MYC reversed cellular ultrastructure into a primitive archetype and induced stem cell markers generating three-germ layers, all qualifiers of acquired pluripotency. Three-factor induced iPS (3F-iPS) clones reproducibly demonstrated cardiac differentiation properties characterized by vigorous beating activity of embryoid bodies and robust expression of cardiac Mef2c, alpha-actinin, connexin43, MLC2a, and troponin I. In vitro isolated iPS-derived cardiomyocytes demonstrated functional excitation-contraction coupling. Chimerism with 3F-iPS derived by morula-stage diploid aggregation was sustained during prenatal heart organogenesis, and contributed in vivo to normal cardiac structure and overall performance in adult tumor-free offspring. Thus, 3F-iPS bioengineered without c-MYC achieve highest stringency criteria for bona fide cardiogenesis enabling reprogrammed fibroblasts to yield de novo heart tissue compatible with native counterpart throughout embryologic development and into adulthood.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for treating myocardial infarction of a heart in a mammal, wherein said method comprises:
    administering induced pluripotent stem (iPS) cells into a site of said myocardial infarction in said mammal such that (a) said site of myocardial infarction in said mammal is repaired without tumor formation in said mammal from said iPS cells, (b) ejection fraction of said heart is increased, (c) fractional shortening of said heart is increased, and (d) regional septal wall thickness in systole of said heart is increased,
    wherein said iPS cells are of the same species as said mammal,
    wherein said iPS cells were obtained using:
        i) a human Oct3/4 polypeptide, a human Sox2 polypeptide, a human Klf4polypeptide, and a human c-Myc polypeptide; or
        ii) one or more non-integrating vectors comprising nucleic acid sequences encoding said human Oct3/4 polypeptide, said human Sox2 polypeptide, said human Klf4polypeptide, and said human c-Myc polypeptide.

2. The method of claim 1, wherein said iPS cells were obtained using said one or more non-integrating vectors, and wherein said one or more non-integrating vectors further comprise nucleic acid encoding a human Nanog polypeptide.

3. The method of claim 1, wherein said iPS cells were obtained using said one or more non-integrating vectors, and wherein said one or more non-integrating vectors are non-integrating viral vectors.

4. A method for treating myocardial infarction in a mammal, wherein said method comprises:
    administering induced pluripotent stem (iPS) cells into a site of said myocardial infarction in said mammal such that (a) progeny of said iPS cells become engrafted with said site of said myocardial infarction of said mammal without tumor formation in said mammal from said iPS cells, (b) ejection fraction of said heart is increased, (c) fractional shortening of said heart is increased, and (d) regional septal wall thickness in systole of said heart is increased,
    wherein said iPS cells are of the same species as said mammal,
    wherein said iPS cells were obtained using:
        i) a human Oct3/4 polypeptide, a human Sox2 polypeptide, a human Klf4polypeptide, and a human c-Myc polypeptide; or ii) one or more non-integrating vectors comprising nucleic acid sequences encoding said human Oct3/4 polypeptide, said human Sox2 polypeptide, said human Klf4 polypeptide, and said human c-Myc polypeptide.

5. The method of claim 4, wherein said iPS cells were obtained using said one or more non-integrating vectors, and wherein said one or more non-integrating vectors further comprise nucleic acid encoding a human Nanog polypeptide.

6. The method of claim 4, wherein said iPS cells were obtained using said one or more non-integrating vectors, and wherein said one or more non-integrating vectors are non-integrating viral vectors.

* * * * *

UNITED STATES PATENT AND TRADEMARK OFFICE
CERTIFICATE OF CORRECTION

PATENT NO. : 10,047,346 B2
APPLICATION NO. : 13/058154
DATED : August 14, 2018
INVENTOR(S) : Yasuhiro Ikeda et al.

It is certified that error appears in the above-identified patent and that said Letters Patent is hereby corrected as shown below:

In the Specification

Column 1, Line 17, after "claims" delete "the".

In the Claims

In Claim 1, Column 43, Line 59, delete "Klf4polypeptide," and insert -- Klf4 polypeptide, --, therefor.

In Claim 1, Column 43, Line 64, delete "Klf4polypeptide," and insert -- Klf4 polypeptide, --, therefor.

In Claim 4, Column 44, Line 66, delete "Klf4polypeptide," and insert -- Klf4 polypeptide, --, therefor.

In Claim 4, Column 45, Line 4, delete "Klf4polypeptide," and insert -- Klf4 polypeptide, --, therefor.

Signed and Sealed this
Thirtieth Day of April, 2019

Andrei Iancu
*Director of the United States Patent and Trademark Office*

```
                             SEQUENCE LISTING

<160> NUMBER OF SEQ ID NOS: 12

<210> SEQ ID NO 1
<211> LENGTH: 39
<212> TYPE: DNA
<213> ORGANISM: Homo sapiens

<400> SEQUENCE: 1
ataggatccg ccaccatggc gggacacctg gcttcggat                              39

<210> SEQ ID NO 2
<211> LENGTH: 35
<212> TYPE: DNA
<213> ORGANISM: Homo sapiens

<400> SEQUENCE: 2
atagcggccg ctcagtttga atgcatggga gagcc                                 35

<210> SEQ ID NO 3
<211> LENGTH: 36
<212> TYPE: DNA
<213> ORGANISM: Homo sapiens

<400> SEQUENCE: 3
ataggatcca ccatgtacaa catgatggag acggag                                36

<210> SEQ ID NO 4
<211> LENGTH: 35
<212> TYPE: DNA
<213> ORGANISM: Homo sapiens

<400> SEQUENCE: 4
atagcggccg ctcacatgtg tgagaggggc agtgt                                 35

<210> SEQ ID NO 5
<211> LENGTH: 43
<212> TYPE: DNA
<213> ORGANISM: Homo sapiens

<400> SEQUENCE: 5
gacgaattcg gatccaccat gaggcagcca cctggcgagt ctg                        43

<210> SEQ ID NO 6
<211> LENGTH: 41
<212> TYPE: DNA
<213> ORGANISM: Homo sapiens

<400> SEQUENCE: 6
gacctcgagc ggccgcttaa aaatgcctct tcatgtgtaa g                          41

<210> SEQ ID NO 7
<211> LENGTH: 33
<212> TYPE: DNA
<213> ORGANISM: Homo sapiens

<400> SEQUENCE: 7
ctgatcaagg ctctccttgc agctgcttag acg                                   33
```

```
<210> SEQ ID NO 8
<211> LENGTH: 35
<212> TYPE: DNA
<213> ORGANISM: Homo sapiens

<400> SEQUENCE: 8
atagcggccg cttacgcaca agagttccgt agctg                          35

<210> SEQ ID NO 9
<211> LENGTH: 22
<212> TYPE: DNA
<213> ORGANISM: Homo sapiens

<400> SEQUENCE: 9
agccgccttg gggcactagc cc                                        22

<210> SEQ ID NO 10
<211> LENGTH: 22
<212> TYPE: DNA
<213> ORGANISM: Homo sapiens

<400> SEQUENCE: 10
cgcaagccgc accggctccg cc                                        22

<210> SEQ ID NO 11
<211> LENGTH: 22
<212> TYPE: DNA
<213> ORGANISM: Homo sapiens

<400> SEQUENCE: 11
agcctcgtcg atgaacggcc gc                                        22

<210> SEQ ID NO 12
<211> LENGTH: 22
<212> TYPE: DNA
<213> ORGANISM: Homo sapiens

<400> SEQUENCE: 12
ctcactcggc gcgccagtcc tc                                        22
```